US008394125B2

(12) United States Patent
Assell et al.

(10) Patent No.: US 8,394,125 B2
(45) Date of Patent: Mar. 12, 2013

(54) SYSTEMS AND METHODS FOR FACET JOINT TREATMENT

(75) Inventors: Robert Assell, St. Paul, MN (US); Brian P. Beaubien, St. Paul, MN (US); Eugene A. Dickhudt, Lino Lakes, MN (US)

(73) Assignee: Zyga Technology, Inc., Minneapolis, MN (US)

( * ) Notice: Subject to any disclaimer, the term of this patent is extended or adjusted under 35 U.S.C. 154(b) by 271 days.

(21) Appl. No.: 12/509,260

(22) Filed: Jul. 24, 2009

(65) Prior Publication Data
US 2011/0022089 A1 Jan. 27, 2011

(51) Int. Cl.
*A61B 17/70* (2006.01)
(52) U.S. Cl. ........................................................ 606/247
(58) Field of Classification Search ............... 606/60, 606/246–247; 623/17.15–17.16, 14.12
See application file for complete search history.

(56) References Cited

U.S. PATENT DOCUMENTS

| | | | |
|---|---|---|---|
| 2,677,369 A | 5/1954 | Knowles | |
| 3,426,364 A | 2/1969 | Lumb | |
| 3,879,767 A | 4/1975 | Stubstad | |
| 4,052,753 A | 10/1977 | Dedo | |
| 4,349,921 A | 9/1982 | Kuntz | |
| 4,502,161 A | 3/1985 | Wall | |
| 4,553,273 A | 11/1985 | Wu | |
| 4,554,914 A | 11/1985 | Kapp | |
| 4,599,086 A | 7/1986 | Doty | |
| 4,636,217 A | 1/1987 | Ogilvie | |
| 4,743,256 A | 5/1988 | Brantigan | |
| 4,834,757 A | 5/1989 | Brantigan | |
| 5,092,866 A | 3/1992 | Breard | |
| 5,147,404 A | 9/1992 | Downey | |
| 5,156,616 A | 10/1992 | Meadows | |
| 5,306,308 A * | 4/1994 | Gross et al. | 623/17.16 |
| 5,415,659 A | 5/1995 | Lee et al. | |

(Continued)

FOREIGN PATENT DOCUMENTS

| | | |
|---|---|---|
| DE | 9304368 | 5/1995 |
| DE | 201 12 123 U1 | 10/2001 |

(Continued)

OTHER PUBLICATIONS http://dictionary.reference.com/browse/orient?s=t, pp. 2-4.*

(Continued)

*Primary Examiner* — Ellen C Hammond
*Assistant Examiner* — Jacqueline Johanas
(74) *Attorney, Agent, or Firm* — Dicke, Billig & Czaja, PLLC

(57) ABSTRACT

A system for treating a facet joint of a patient including superior and inferior resurfacing devices. The superior device includes a resurfacing body configured to conform to a shape of a superior facet articular face, and the inferior device includes a resurfacing body configured to conform to a shape of an inferior facet articular face. Each resurfacing body exhibits sufficient flexibility to transition from a relatively flat state to an inserted state in which the resurfacing body substantially matches any multi-planar concavities of the corresponding facet articular face in the presence of compressive forces. With this construction, the system is capable of establishing a new sliding interface within the facet joint, and can be inserted on a minimally-invasive basis. The resurfacing bodies can be formed of PEEK, and can include teeth that engage the corresponding facet articular face.

18 Claims, 36 Drawing Sheets

U.S. PATENT DOCUMENTS

| | | |
|---|---|---|
| 5,415,661 A | 5/1995 | Holmes |
| 5,496,318 A | 3/1996 | Howland et al. |
| 5,507,823 A | 4/1996 | Walston |
| 5,527,312 A | 6/1996 | Ray |
| 5,571,191 A | 11/1996 | Fitz |
| 5,609,634 A | 3/1997 | Voydeville |
| 5,665,122 A | 9/1997 | Kambin |
| 5,681,310 A | 10/1997 | Yuan |
| 5,683,464 A * | 11/1997 | Wagner et al. ............ 623/17.16 |
| 5,697,889 A | 12/1997 | Slotman |
| 5,968,098 A | 10/1999 | Winslow |
| 6,019,792 A | 2/2000 | Cauthen |
| RE36,758 E | 6/2000 | Fitz |
| 6,102,948 A | 8/2000 | Brosnahan |
| 6,123,464 A | 9/2000 | Murata et al. |
| 6,126,688 A | 10/2000 | McDonnell |
| 6,132,464 A | 10/2000 | Martin |
| 6,132,468 A | 10/2000 | Mansmann |
| 6,156,067 A | 12/2000 | Bryan et al. |
| 6,179,874 B1 | 1/2001 | Cauthen |
| 6,287,313 B1 | 9/2001 | Sasso |
| 6,290,724 B1 | 9/2001 | Marino |
| 6,368,350 B1 | 4/2002 | Erickson et al. |
| 6,440,168 B1 | 8/2002 | Cauthen |
| 6,443,988 B2 | 9/2002 | Felt |
| 6,458,159 B1 * | 10/2002 | Thalgott ..................... 623/17.11 |
| 6,485,518 B1 | 11/2002 | Cornwall et al. |
| 6,540,747 B1 | 4/2003 | Marino |
| 6,544,265 B2 | 4/2003 | Lieberman |
| 6,562,046 B2 | 5/2003 | Sasso |
| 6,610,093 B1 | 8/2003 | Pisharodi |
| 6,652,585 B2 | 11/2003 | Lange |
| 6,652,587 B2 | 11/2003 | Felt |
| 6,679,915 B1 | 1/2004 | Cauthen |
| 6,733,531 B1 | 5/2004 | Trieu |
| 6,846,328 B2 | 1/2005 | Cauthen |
| 6,893,463 B2 | 5/2005 | Fell |
| 6,932,842 B1 | 8/2005 | Litschko |
| 6,966,930 B2 | 11/2005 | Arnin et al. |
| 6,974,478 B2 | 12/2005 | Reiley et al. |
| 6,986,771 B2 | 1/2006 | Paul |
| 6,989,011 B2 | 1/2006 | Paul |
| 7,001,431 B2 | 2/2006 | Bao |
| 7,041,136 B2 | 5/2006 | Goble et al. |
| 7,087,084 B2 | 8/2006 | Reiley |
| 7,101,398 B2 | 9/2006 | Dooris |
| 7,115,131 B2 | 10/2006 | Engh |
| 7,115,132 B2 * | 10/2006 | Errico et al. ................ 606/86 R |
| 7,115,142 B2 | 10/2006 | Muhanna |
| 7,146,665 B1 | 12/2006 | Moorin |
| 7,270,681 B2 | 9/2007 | Cauthen |
| 7,291,169 B2 | 11/2007 | Hodorek |
| 7,371,238 B2 | 5/2008 | Soboleski |
| 7,377,942 B2 | 5/2008 | Berry |
| 7,468,075 B2 | 12/2008 | Lang |
| 7,476,252 B2 | 1/2009 | Foley |
| 7,591,851 B2 | 9/2009 | Winslow et al. |
| 7,615,077 B2 * | 11/2009 | Melkent et al. ............ 623/17.11 |
| 7,618,451 B2 | 11/2009 | Berez |
| 7,708,761 B2 * | 5/2010 | Petersen ....................... 606/247 |
| 7,744,612 B2 | 6/2010 | Blain |
| 7,776,090 B2 | 8/2010 | Winslow |
| 7,846,183 B2 | 12/2010 | Blain |
| 7,922,766 B2 | 4/2011 | Grob |
| 7,927,374 B2 * | 4/2011 | Duggal et al. ............. 623/17.14 |
| 7,935,134 B2 | 5/2011 | Reglos |
| 7,938,836 B2 | 5/2011 | Ainsworth |
| 7,938,857 B2 | 5/2011 | Garcia |
| 7,955,355 B2 | 6/2011 | Chin |
| 7,998,172 B2 | 8/2011 | Blain |
| 8,100,955 B2 | 1/2012 | Blain |
| 2001/0051807 A1 | 12/2001 | Grafton |
| 2002/0026244 A1 | 2/2002 | Trieu |
| 2002/0055737 A1 | 5/2002 | Lieberman |
| 2002/0120270 A1 | 8/2002 | Trieu |
| 2002/0143329 A1 | 10/2002 | Serhan |
| 2002/0151895 A1 | 10/2002 | Soboleski |
| 2003/0028250 A1 | 2/2003 | Reiley |
| 2003/0176871 A1 | 9/2003 | Pavlov et al. |
| 2003/0208202 A1 | 11/2003 | Falahee |
| 2003/0220643 A1 | 11/2003 | Ferree |
| 2004/0010312 A1 | 1/2004 | Enayati |
| 2004/0049280 A1 | 3/2004 | Cauthen |
| 2004/0087954 A1 | 5/2004 | Allen et al. |
| 2004/0143332 A1 * | 7/2004 | Krueger et al. ............ 623/17.14 |
| 2004/0153159 A1 | 8/2004 | Cauthen |
| 2004/0225360 A1 | 11/2004 | Malone |
| 2004/0236328 A1 | 11/2004 | Paul |
| 2004/0260287 A1 | 12/2004 | Ferree |
| 2005/0021029 A1 | 1/2005 | Trieu |
| 2005/0027361 A1 | 2/2005 | Reiley |
| 2005/0049705 A1 | 3/2005 | Hale et al. |
| 2005/0076974 A1 | 4/2005 | Honkura et al. |
| 2005/0080486 A1 | 4/2005 | Fallin et al. |
| 2005/0085912 A1 | 4/2005 | Arnin et al. |
| 2005/0119748 A1 | 6/2005 | Reiley et al. |
| 2005/0125062 A1 | 6/2005 | Biedermann |
| 2005/0143818 A1 | 6/2005 | Yuan et al. |
| 2005/0143825 A1 | 6/2005 | Enayati |
| 2005/0159746 A1 | 7/2005 | Grob et al. |
| 2005/0177240 A1 | 8/2005 | Blain |
| 2005/0197700 A1 * | 9/2005 | Boehm et al. ............. 623/17.11 |
| 2005/0197706 A1 * | 9/2005 | Hovorka et al. ........... 623/17.15 |
| 2005/0251256 A1 | 11/2005 | Reiley |
| 2005/0273100 A1 | 12/2005 | Taylor |
| 2006/0009847 A1 | 1/2006 | Reiley |
| 2006/0036243 A1 | 2/2006 | Sasso |
| 2006/0036323 A1 | 2/2006 | Carl et al. |
| 2006/0041311 A1 | 2/2006 | McLeer |
| 2006/0064099 A1 | 3/2006 | Pavlov et al. |
| 2006/0084977 A1 | 4/2006 | Lieberman |
| 2006/0085068 A1 | 4/2006 | Barry |
| 2006/0111779 A1 | 5/2006 | Petersen |
| 2006/0111780 A1 | 5/2006 | Peterson |
| 2006/0111781 A1 | 5/2006 | Petersen |
| 2006/0111782 A1 | 5/2006 | Petersen |
| 2006/0116768 A1 * | 6/2006 | Krueger et al. ............ 623/17.14 |
| 2006/0122701 A1 * | 6/2006 | Kiester ....................... 623/17.11 |
| 2006/0149374 A1 | 7/2006 | Winslow |
| 2006/0155297 A1 | 7/2006 | Ainsworth |
| 2006/0190081 A1 | 8/2006 | Kraus et al. |
| 2006/0235391 A1 | 10/2006 | Sutterlin |
| 2006/0235403 A1 | 10/2006 | Blain |
| 2006/0235409 A1 | 10/2006 | Blain |
| 2006/0235412 A1 | 10/2006 | Blain |
| 2006/0235518 A1 | 10/2006 | Blain |
| 2006/0235533 A1 | 10/2006 | Blain |
| 2006/0241758 A1 | 10/2006 | Peterman et al. |
| 2006/0247632 A1 | 11/2006 | Winslow |
| 2006/0247633 A1 | 11/2006 | Winslow et al. |
| 2006/0276790 A1 | 12/2006 | Dawson et al. |
| 2006/0276907 A1 | 12/2006 | Boyer |
| 2007/0032790 A1 | 2/2007 | Aschmann et al. |
| 2007/0055236 A1 | 3/2007 | Hudgins |
| 2007/0055252 A1 | 3/2007 | Blain |
| 2007/0055373 A1 | 3/2007 | Hudgins et al. |
| 2007/0067032 A1 | 3/2007 | Felt et al. |
| 2007/0083265 A1 | 4/2007 | Malone |
| 2007/0083266 A1 | 4/2007 | Lang |
| 2007/0088358 A1 | 4/2007 | Yuan et al. |
| 2007/0100450 A1 | 5/2007 | Hodorek |
| 2007/0118218 A1 * | 5/2007 | Hooper ....................... 623/14.12 |
| 2007/0123863 A1 | 5/2007 | Winslow et al. |
| 2007/0135814 A1 | 6/2007 | Farris |
| 2007/0135919 A1 | 6/2007 | Aebi et al. |
| 2007/0149976 A1 | 6/2007 | Hale et al. |
| 2007/0161991 A1 | 7/2007 | Altarac |
| 2007/0167946 A1 | 7/2007 | Triplett |
| 2007/0179608 A1 | 8/2007 | Ek et al. |
| 2007/0225813 A1 | 9/2007 | Haines |
| 2007/0276370 A1 | 11/2007 | Altarac |
| 2007/0276498 A1 | 11/2007 | Aebi et al. |
| 2007/0276499 A1 | 11/2007 | Paul |
| 2008/0009875 A1 | 1/2008 | Sankaran |
| 2008/0027543 A1 * | 1/2008 | Eisermann et al. ........ 623/17.11 |
| 2008/0027547 A1 * | 1/2008 | Yu et al. .................... 623/17.13 |
| 2008/0045954 A1 | 2/2008 | Reiley et al. |

| | | | |
|---|---|---|---|
| 2008/0051901 A1* | 2/2008 | de Villiers et al. | 623/17.16 |
| 2008/0091199 A1 | 4/2008 | Cragg | |
| 2008/0097613 A1 | 4/2008 | Reiley et al. | |
| 2008/0119933 A1 | 5/2008 | Aebi et al. | |
| 2008/0125814 A1 | 5/2008 | Yuan et al. | |
| 2008/0132951 A1 | 6/2008 | Reiley et al. | |
| 2008/0140121 A1 | 6/2008 | McLeer | |
| 2008/0143818 A1 | 6/2008 | Ferren | |
| 2008/0154305 A1 | 6/2008 | Foley et al. | |
| 2008/0208249 A1 | 8/2008 | Blain | |
| 2008/0262555 A1 | 10/2008 | Assell | |
| 2009/0062920 A1* | 3/2009 | Tauber | 623/17.16 |
| 2009/0088846 A1 | 4/2009 | Myung | |
| 2009/0138053 A1 | 5/2009 | Assell | |
| 2009/0177205 A1 | 7/2009 | McCormack | |
| 2009/0234458 A1* | 9/2009 | de Villiers et al. | 623/17.16 |
| 2009/0264928 A1 | 10/2009 | Blain | |
| 2010/0131008 A1 | 5/2010 | Overes | |
| 2010/0228288 A1 | 9/2010 | Blain | |
| 2010/0249937 A1 | 9/2010 | Blain | |
| 2010/0274286 A1 | 10/2010 | Blain | |
| 2010/0286778 A1 | 11/2010 | Eisermann | |
| 2010/0292797 A1* | 11/2010 | Lindner et al. | 623/17.11 |
| 2011/0022089 A1 | 1/2011 | Assell | |
| 2011/0040301 A1 | 2/2011 | Blain | |
| 2011/0060366 A1 | 3/2011 | Heim | |
| 2011/0082503 A1 | 4/2011 | Blain | |
| 2011/0313456 A1 | 12/2011 | Blain | |

FOREIGN PATENT DOCUMENTS

| | | |
|---|---|---|
| DE | 20 2007 015 081 U1 | 2/2008 |
| DE | 20 2009 006 906 U1 | 8/2009 |
| EP | 381588 | 8/1990 |
| FR | 2681525 | 3/1993 |
| FR | 2717675 | 9/1995 |
| WO | 9310725 | 6/1993 |
| WO | 9405235 | 3/1994 |
| WO | 0234147 | 2/2002 |
| WO | 0245765 | 6/2002 |
| WO | 02065954 | 8/2002 |
| WO | 2005/072661 A1 | 8/2005 |
| WO | 2005/076974 A2 | 8/2005 |
| WO | 2006020464 | 2/2006 |
| WO | 2006/065774 A1 | 6/2006 |
| WO | 2006096803 | 9/2006 |
| WO | 2007/019215 A2 | 2/2007 |
| WO | 2009143496 | 11/2009 |
| WO | 2011011621 | 1/2011 |

OTHER PUBLICATIONS http://dictionary.reference.com/browse/end?s=t, pp. 2-6.*
http://dictionary.reference.com/browse/orient?s=t, pp. 2-4. Retrieved on Jun. 18, 2012.*
http://dictionary.reference.com/browse/end?s=t, pp. 2-6. Retrieved on Jun. 18, 2012.*
PCT Search Report (mailed Dec. 20, 2010); 12 pgs.

* cited by examiner

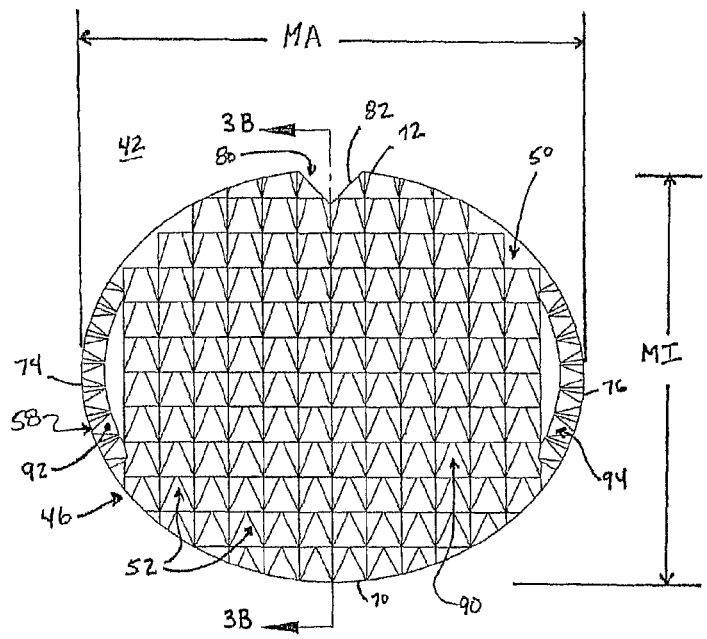
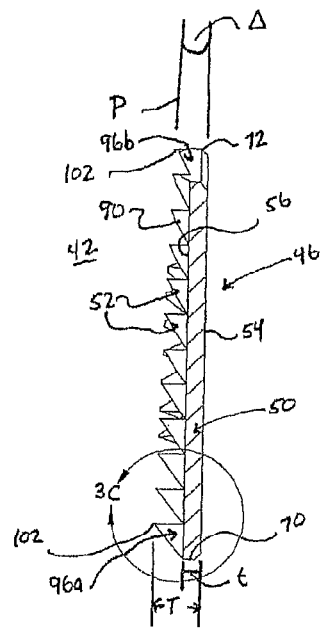
Fig. 3A
FIG. 3B
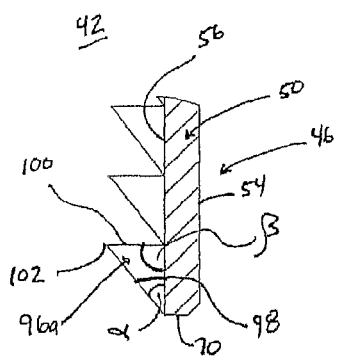
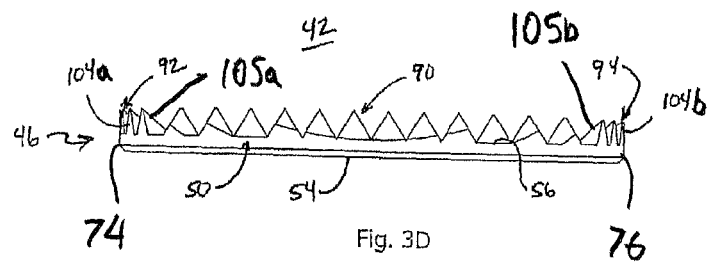
FIG. 3C
Fig. 3D

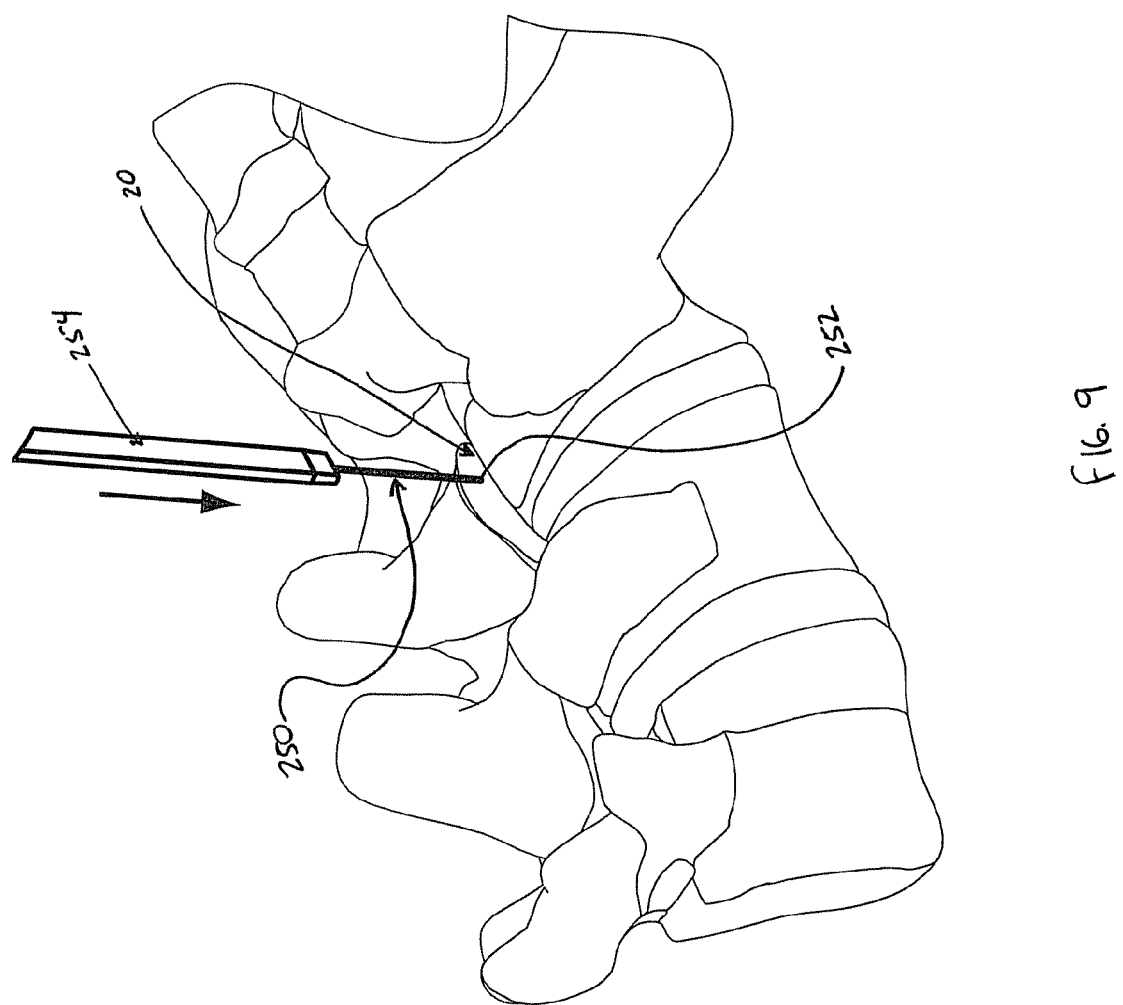

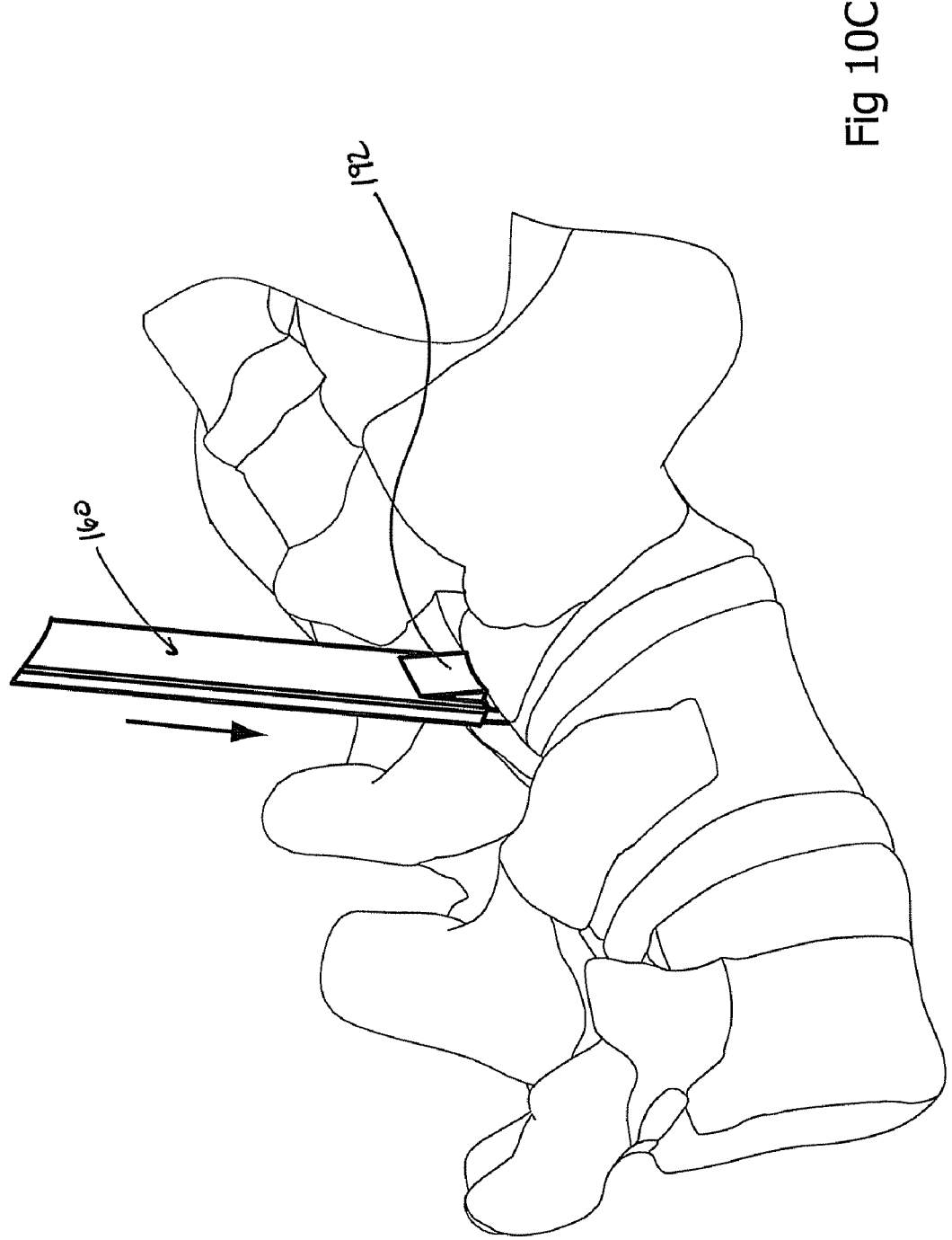

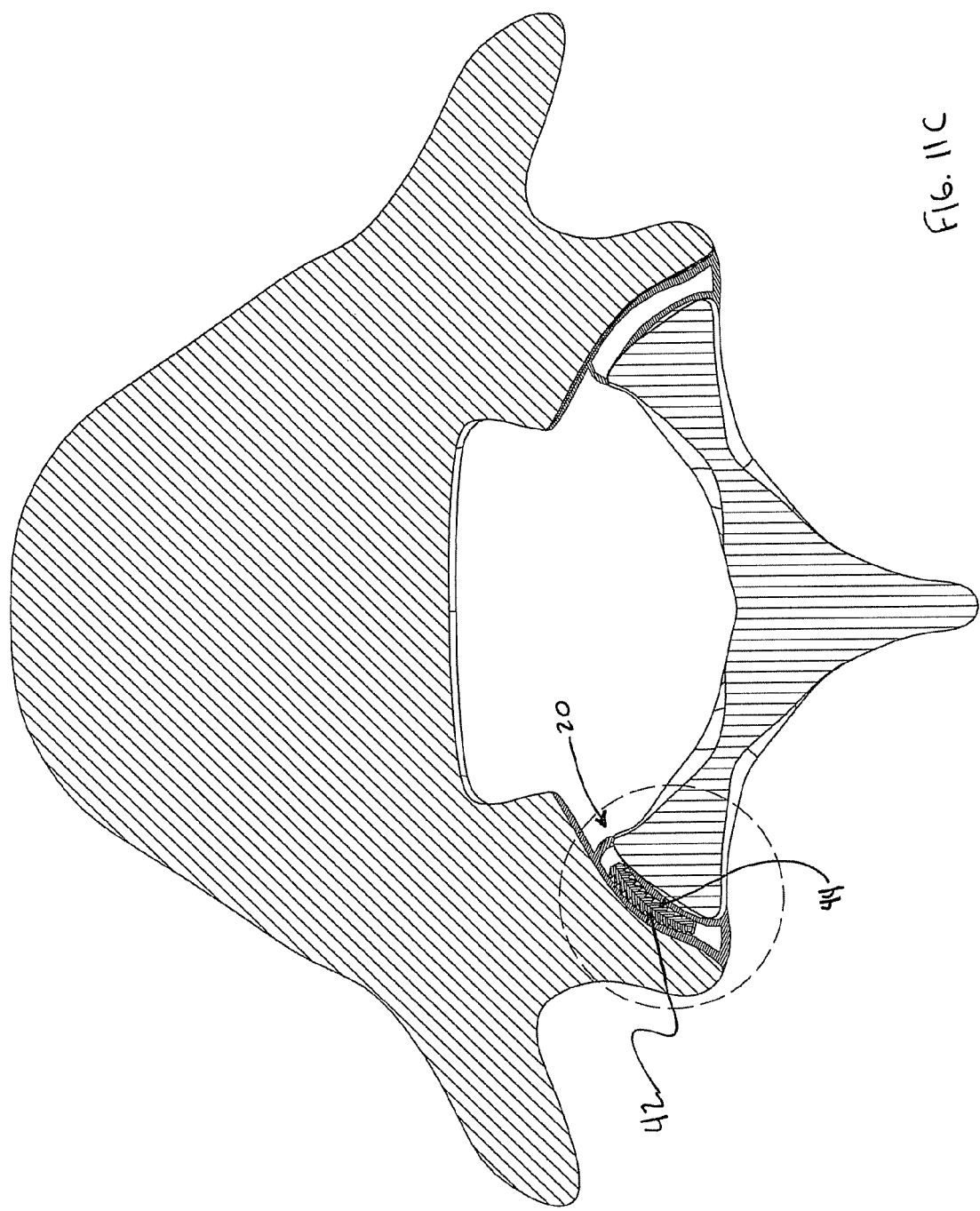

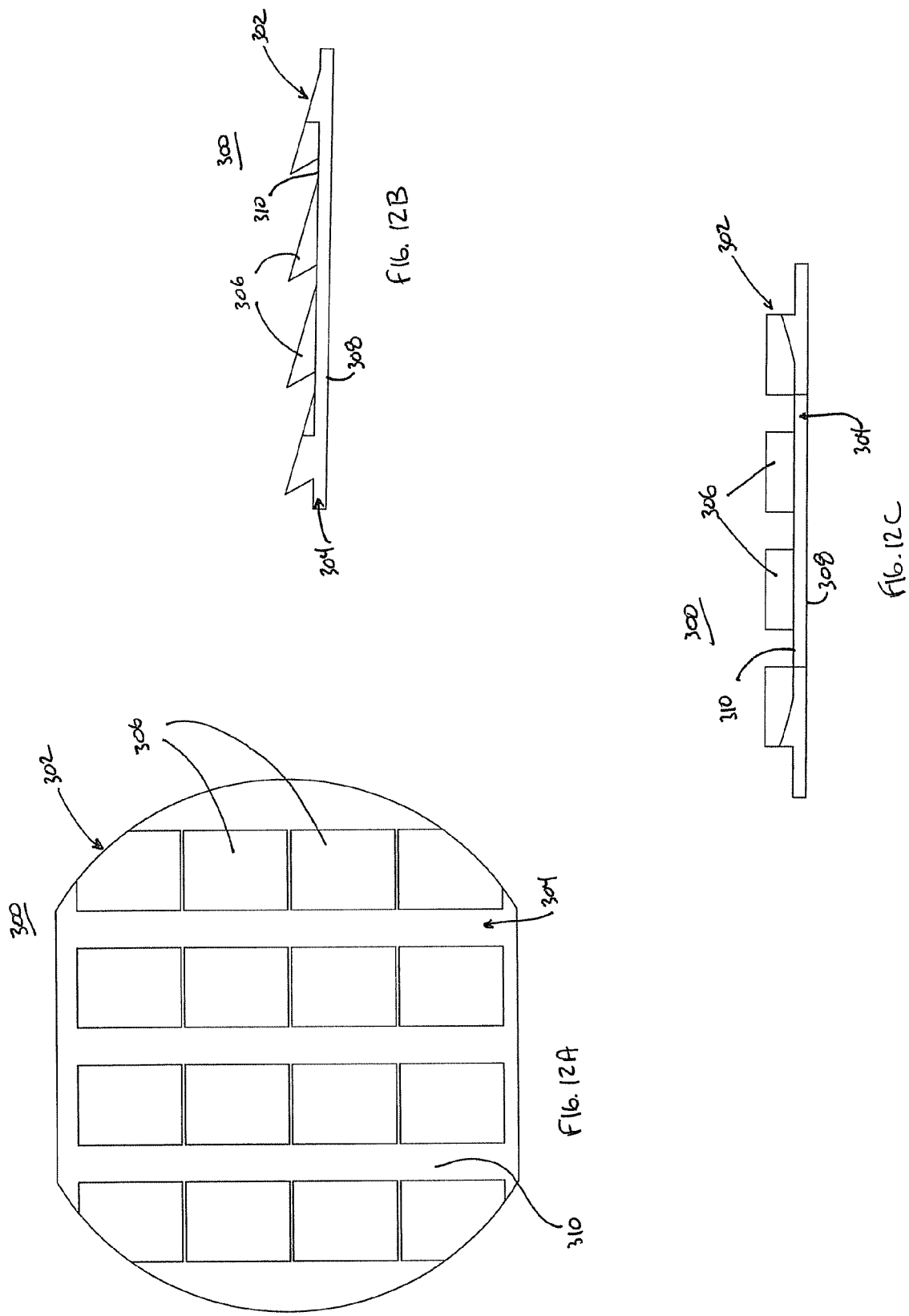

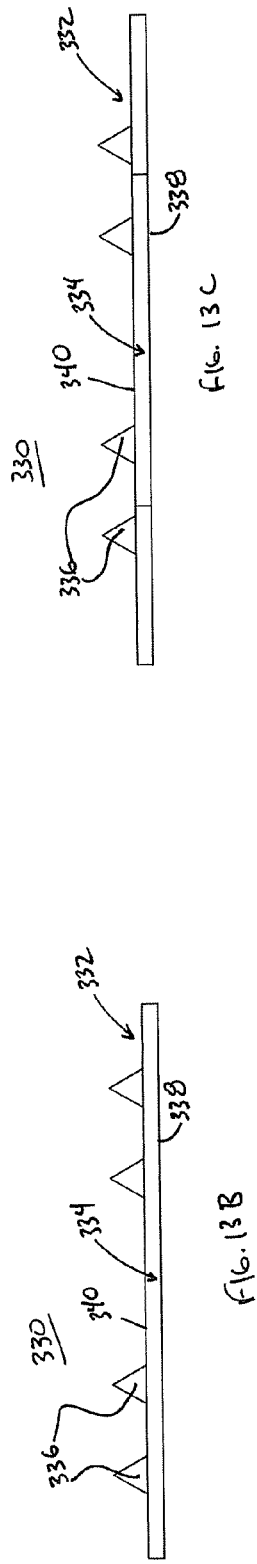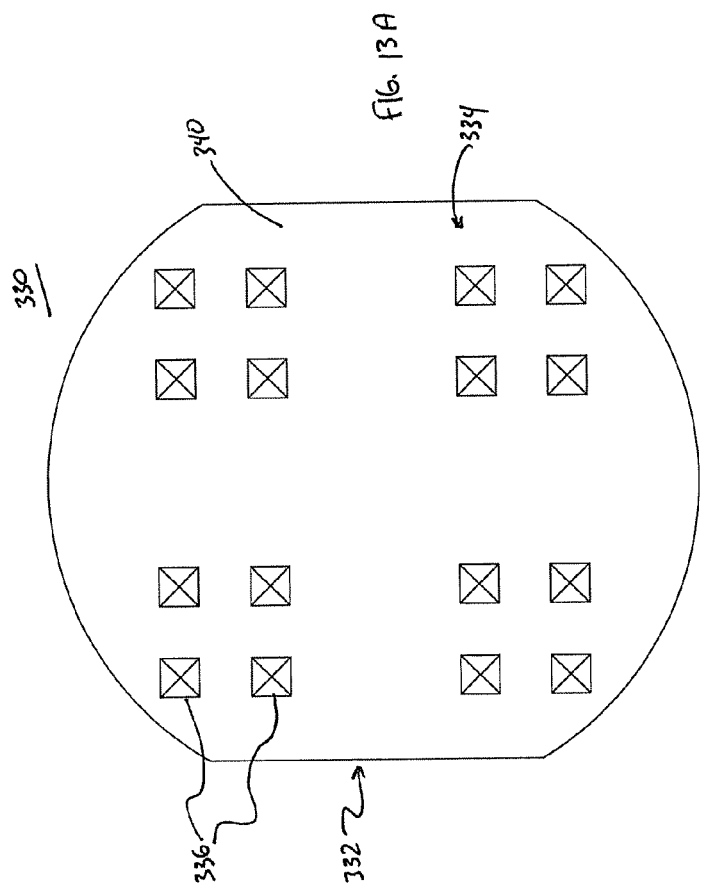

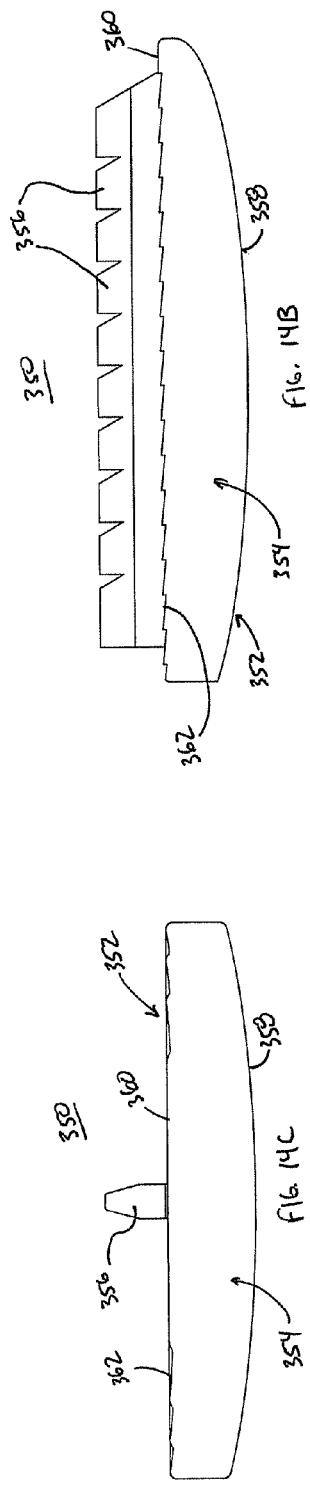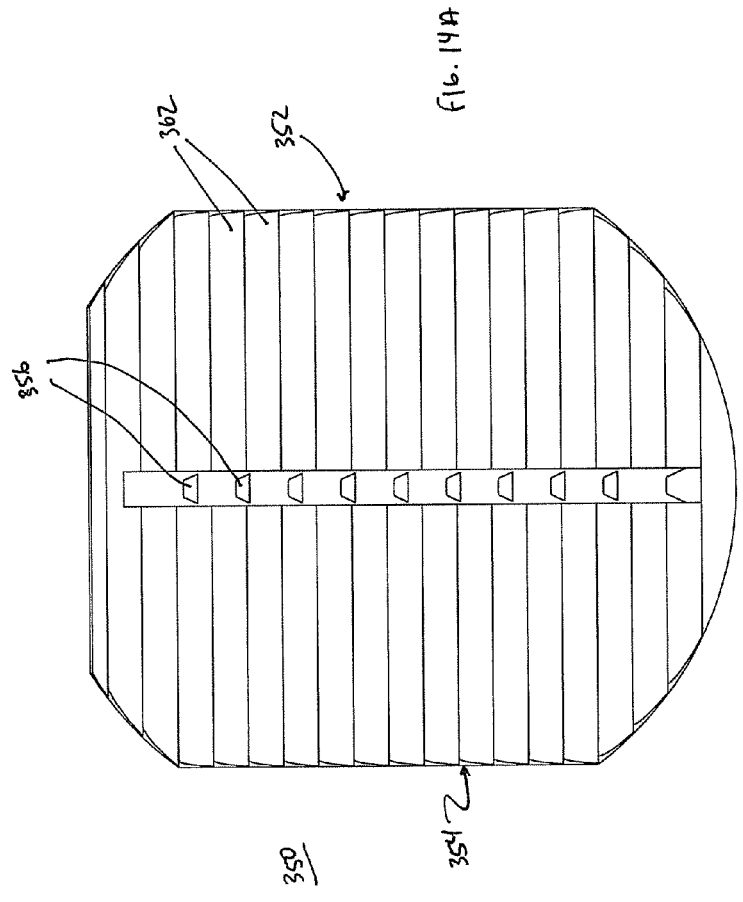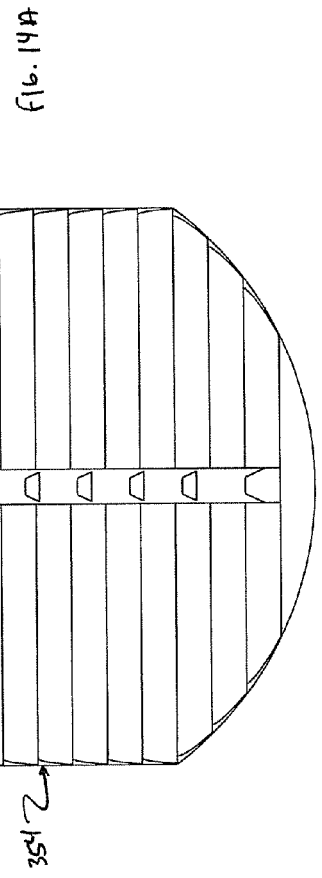

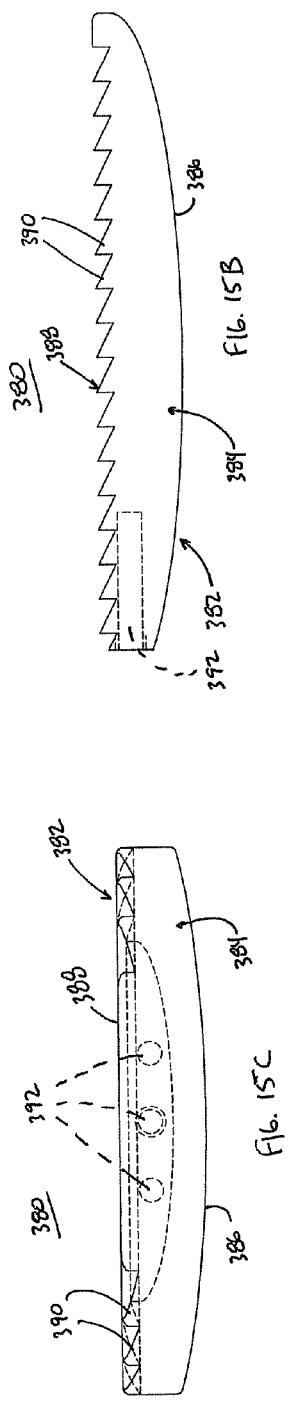
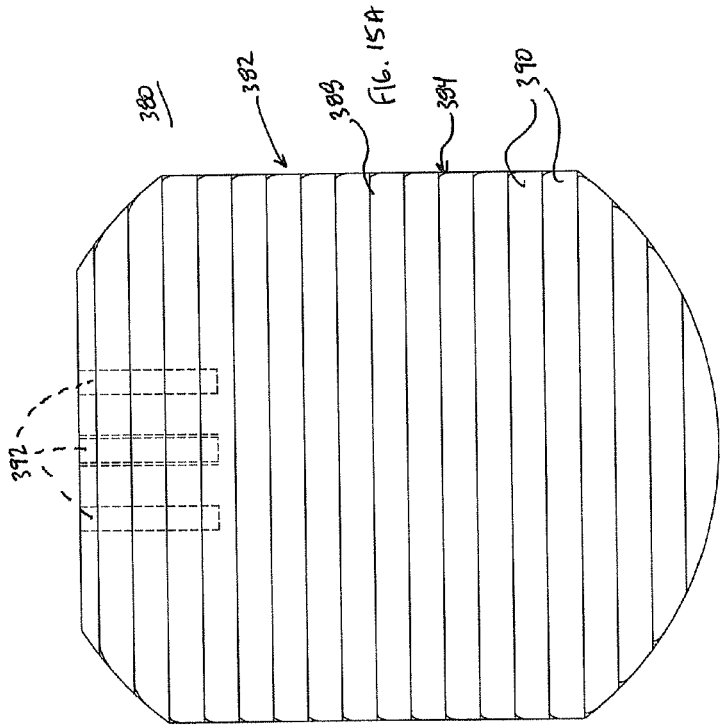

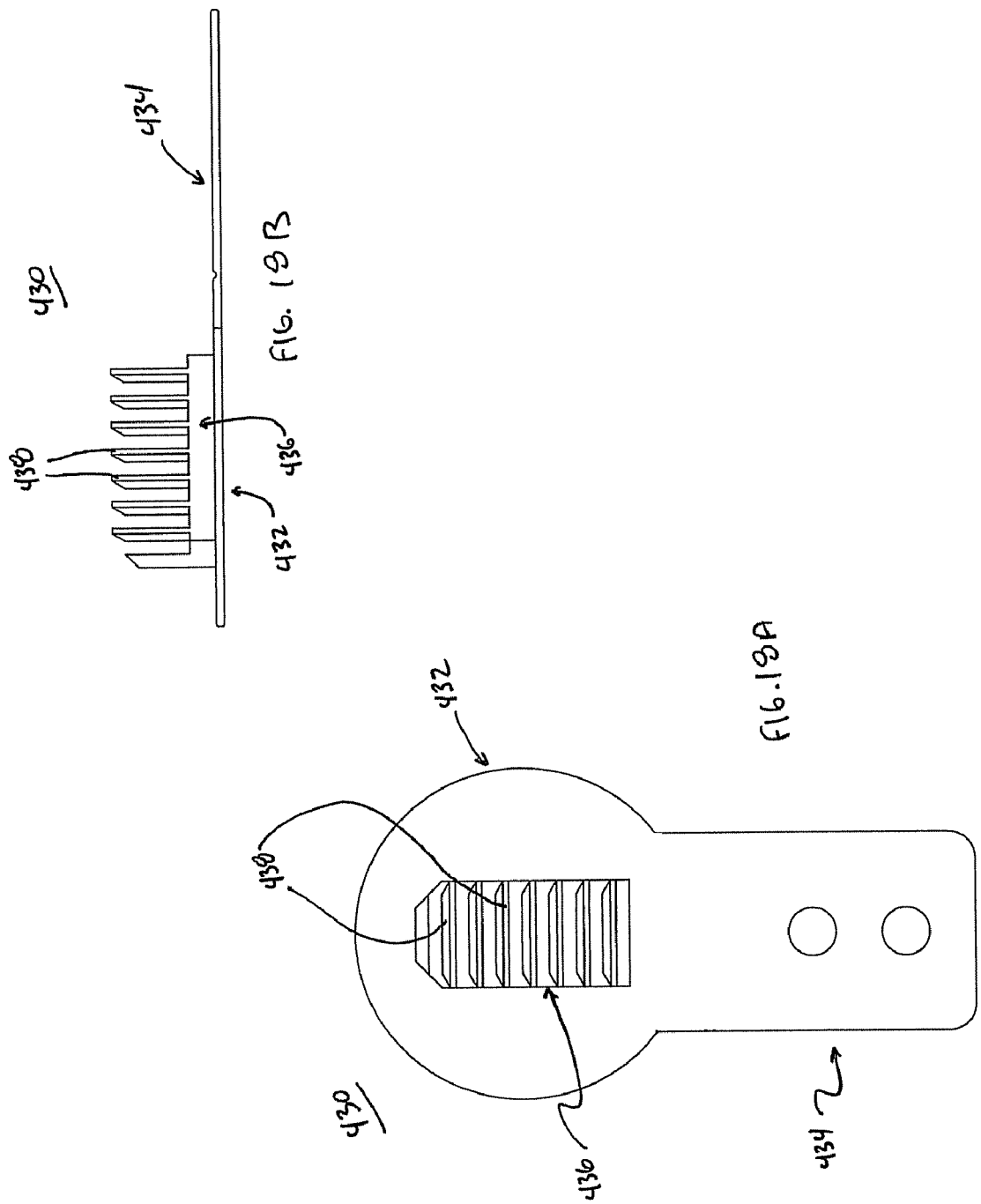

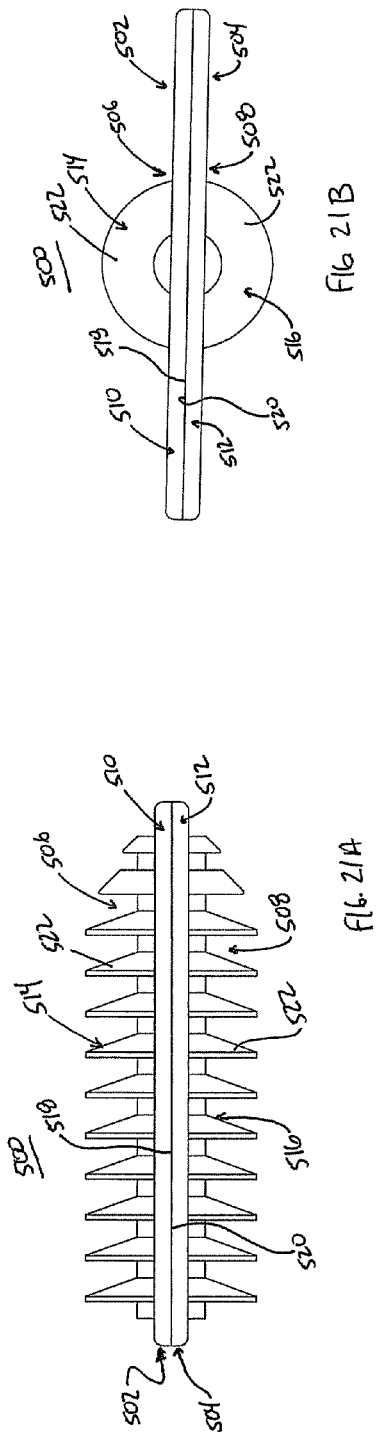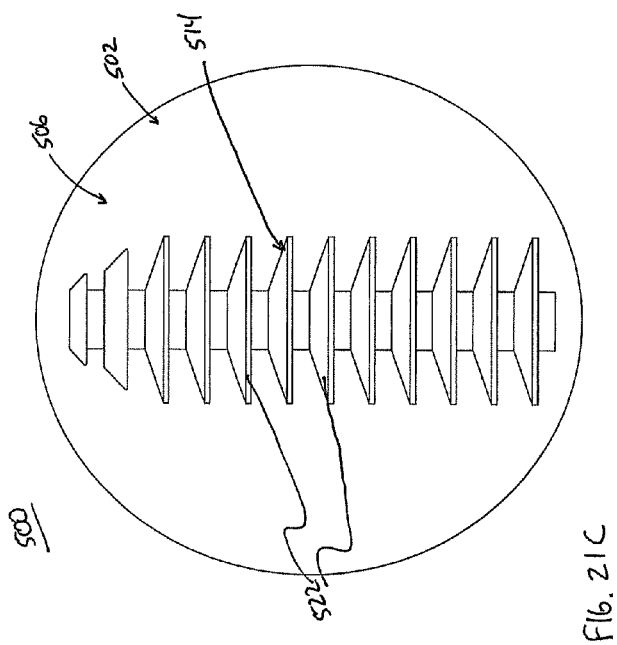
FIG. 21A
FIG. 21B
FIG. 21C

SYSTEMS AND METHODS FOR FACET JOINT TREATMENT

BACKGROUND

The present disclosure relates to systems and methods for treating patients experiencing zygapophyseal (facet) joint-related pain. More particularly, it relates to implantable systems, and corresponding insertion methods and procedures, that effectuate resurfacing of the facet joint anatomy on a minimally-invasive basis to minimize pain and reestablish or maintain normal or near-normal facet joint stabilization and motion.

Within the next ten years, more than seventy million people will join the ranks of seniors. In an aging population, the articular cartilage that allows bones to smoothly move over each other wears down with time and disease, and like many tissues in the body, articular cartilage has a limited ability to heal itself At this time, options that help to relieve severe degenerative joint pain, or osteoarthritis, include joint replacement or fusion. As examples, approximately 200,000 total knee joint and over 300,000 hip joint replacement operations are performed annually, and typically these artificial joints last about 10-15 years. Chronic lower back pain also affects both work force productivity and healthcare expense, and there are currently over 500,000 surgical procedures performed annually in the United States in an attempt to alleviate lower back pain that persists following failure of more conservative therapy (e.g., bed rest, pain and muscle relaxant medication, physical therapy or steroid injection). The source of this pain may originate from dysfunction among a plurality of anatomical structures (as described below) that are comprised in the spine, including facet joints.

To understand spinal biomechanics, and the impacts of dysfunction in therapy, it is perhaps useful to first consider the spinal anatomy. The vertebrae of the spine are conventionally subdivided into several sections. Moving from the head (cephalad) to the tailbone (caudal), the sections are cervical, thoracic, lumbar, sacral, and coccygeal. Regardless of location, each vertebra forms two pedicles and two laminae that combine to define a spinal foramen in which the spinal cord is protected. Extending laterally from the pedicles are two transverse processes. Extending from the mid-line of the vertebra where the two laminae meet is a spinous process. These three processes serve as a connection point for ligaments and muscles. Adjacent vertebrae are separated by an intervertebral disc and surfaces of the adjacent vertebrae form portions of two facet joints by and between the two vertebrae (it being understood that relative to a spinal segment consisting of an intermediate vertebra, an immediately adjacent cephalad vertebra, and an immediately adjacent caudal vertebra, the intermediate vertebra forms portions of four facet joints; namely, two facet joints with the cephalad vertebra, and two facet joints with the caudal vertebra).

With the above background in mind, FIGS. 1A and 1B illustrate a facet joint 20 composed of a superior articular facet 22 and an inferior articular facet 24. The superior articular facet 22 is formed by the vertebral level below the intervertebral disc (i.e., a superior articular facet projects upward from the junction of the lamina and the pedicle), whereas the inferior articular facet 24 is formed by the vertebral level above the intervertebral disc (i.e., an inferior articular facet projects downward). On the superior articular facet 22 is a superior articular face 26, and on the inferior articular facet 24 is an inferior articular face 28. Facet joints are oriented obliquely to the sagittal plane, and the joint space itself is curved from front to back. The more posteriorly located inferior face 28 is convex, whereas the more interiorly located superior face 26 is concave. The facet joint 20 is a synovial joint; effectively defined by the two opposing bony faces 26, 28 with cartilage 30 between them and a capsule 32 around the joint 20. More specifically, synovial fluid 34 is contained inside the joint 20 by the capsule 32, that is otherwise a water-tight sac of soft tissue and ligaments that fully surrounds and encloses the joint 20, and keeps the joint faces 26, 28 lubricated. The ends of the bone articular facets 22, 24 that make up the synovial facet joint 20 are normally covered with the articular, hyaline cartilage 30 that allows the bony faces 26, 28 to glide against one another, providing the flexibility that allows the movement of vertebral bodies relative to one another.

As indicated above, there are two facet joints between each pair of vertebrae, one on each side (located posterior and lateral of the vertebral centerline), from the top and bottom of each vertebra. The joints combine with the disc space to create a three joint complex at each vertebral level, and each joint extends and overlaps neighboring vertebral facet joints, linking each other and hence the vertebra together. The assembly of two vertebral bodies, the interposed spinal disc and the attached ligaments, muscles, and facet joints (inferior articulating processes that articulate with the superior articular processes of the next succeeding vertebra in the caudal direction) is referred to as a "spinal motion segment". Each motion segment contributes the overall flexibility of the spine and contributes to the overall ability of the spine to provide support for the movement of the trunk and head, and in particular, the facet joints limit torsional (twisting) motion. When the facets of one or more vertebral bodies degenerate or otherwise become damaged such that the vertebrae no long articulate or properly align with each other, there is a resulting loss of mobility and pain or discomfort. The functional role of the facet joints in a spinal motion segment is thus relevant to an understanding of the operative and functional advantages of the facet joint systems and methods disclosed herein, which achieve dynamic stabilization and mobility preservation without constraining motion in any plane.

As indicated above, facet joints are located on the posterior column of the spine. The context of this discussion: "anterior" refers to in front of the spinal column, and "posterior" refers to behind the column; "cephalad" means towards a patient's head (sometimes referred to as "superior"); and "caudal" (sometimes referred to as "inferior") refers to the direction or location that is closer to the patient's feet. As the present disclosure contemplates accessing various vertebral elements and joints through a preferred approach that comes in from a percutaneous posterior approach, "proximal" and "distal" are defined in context of this channel of approach. Consequently, "proximal" is closer to the beginning of the channel and thus closer to the clinician, and "distal" is further from the beginning of the channel and thus more distant from the clinician. When referencing access or delivery tools, "distal" would be the end intended for insertion into the access channel, and "proximal" refers to the opposing end, generally the end closer to the handle of the delivery tool. When referencing implants, generally "distal" would be the leading end first inserted into the joint and "proximal" refers to the trailing end, generally in an engagement with a deployment tool.

Facet joints can be arthritic due to degeneration with aging, trauma, or disease (e.g., pathologies that include inflammatory, metabolic, or synovial, disorders). In addition, fractures, torn ligaments, and disc problems (e.g., dehydration or herniation) can all cause abnormal movement and alignment, putting extra stress on the surfaces of the facet joint.

The physiological response to this extra pressure is the development of osteophites, i.e., bone spurs. As the spurs form around the edges of the facet joint, the joint becomes enlarged, a condition called hypertrophy, and eventually the joint surfaces become arthritic. When the articular cartilage degenerates or wears away, the bone underneath is uncovered and rubs against bone. The joint thus becomes inflamed, swollen, and painful.

Facet joint arthritis is a significant source of neck and back pain, and is attributable to about 15-30% of persistent lower back pain complaints. Upon failure of conservative treatment for facet joint pain such as intra-articular steroids/local anesthetic injections administered under fluoroscopic guidance, some patients with chronic pain may eventually require surgical intervention for facet joint arthritis including, for example, facet rhizotomy; facet ectomony to remove the facet joint to reduce pressure on the exiting nerve root; total joint replacement or facet arthrodesis (i.e., fixation leading to fusion, where the two articulating surfaces of the joint remain immobile or grow solidly together and form a single, solid piece of bone); etc. While these surgical procedures may alleviate back pain, many joint replacements and all fusions do not restore the normal physiological function and motion attributable to healthy anatomical form. Rather, they often significantly alter spinal biomechanics that can in turn cause or exacerbate co-existing spinal instabilities and degeneration at other spinal levels or in other joints associated with spinal motion.

There is a cause-and-effect relationship among intervertebral disc integrity, facet loads, and spinal degeneration. Specifically, the progressive loss of disc height with disc degeneration often also alters the facet joint's mechanical ability as the facet joints degenerate or dislocate, and ligaments lose elasticity and their load-carrying ability. More specifically, with disc-space narrowing, as frequently occurs with degenerative disc disease, there is an increased load in the facet joints, especially in extension, and concomitant degeneration of the facet joints and capsules. Since the facet joint capsules are primarily loaded in flexion and in rotation, and the facet joints are the primary resistors against rotational or torsional forces (e.g., normally, the facet joints control approximately 30% of axial rotation), facet joint degeneration significantly alters spinal mobility.

The need to provide minimally invasive therapies that provide pain relief while restoring and preserving the biomechanical function of the physiological facet joints is paramount to overall spinal mobility, and to date, therapies have not adequately satisfied all of these issues, as noted below.

One therapy, facet rhizotomy, involves techniques that sever small nerves that go to the facet joint. The intent of the procedure is to stop the transmission of pain impulses along these nerves. The nerve(s) is identified using a diagnostic injection. Then, the surgeon inserts a large, hollow needle through the tissues in the low back. A radiofrequency probe is inserted through the needle, and a fluoroscope is used to guide the probe toward the nerve. The probe is slowly heated until the nerve is severed. Another technique using pulsed radiofrequency does not actually burn the nerve, rather it is believed to stun the nerve. Yet another technique involves denervation by probe tip freezing, and still another procedure involves carefully controlled injection of botox toxin to treat muscle spasm, a protective reflex that may occur when the facets are inflamed that in turn causes the nearby muscles that parallel the spine to go into spasm. While these procedures may provide pain relief, they do not address ongoing joint degeneration (e.g., wear on articulating surfaces), which leads to kinematic and biomechanical dysfunction that may in turn lead to transition syndrome (i.e., progression of degeneration and pain to other joints) at other levels.

While certain clinicians have advocated prosthetic total joint replacement of damaged facet joints, in practice, it is difficult to implement such a prosthesis for a variety of reasons including the variability of facet joint geometry from facet joint to facet joint, and the high level of interaction between the facet joint and the other components in the spinal column. Moreover, joint replacement is a highly invasive and time-consuming procedure, requiring pre-preparation of joint surfaces and removal of bone, and thus there are associated risks, including blood loss and morbidity, increased anesthesia time, and increased convalescence time.

A related therapeutic treatment of the facet joint entails the provision of an artificial facet joint where the inferior facet segment, the mating superior facet segment, or both, are covered with a cap (i.e., over all, or substantially all, of the facet). One such device and related method of implantation is described in Fitz, U.S. Pat. No. RE 36,758. While potentially viable, the capping of the facet segments has several potential disadvantages. Clinical concerns are believed to result from the disruption of the periosteum and ligamenturn teres femoris, both serving a nutrition delivery role to the femoral head, thereby leading to avascular necrosis of the bony support structure for the cap. Another potential disadvantage of facet capping is that in order to accommodate the wide variability in anatomical morphology of the facets, not only between individuals, but also between levels within the spinal column, a very wide range of cap sizes and shapes is required. Even further, implantation of the caps, such as those described in U.S. Pat. No. RE. 36,758, cannot be performed on a minimally-invasive basis, and entail fairly significant preparatory steps at the implantation site (e.g., removal and/or re-shaping of bone). At least with use of caps over osteoarthritic femoral heads, the capping of articular bone ends has sometimes experienced clinical failure by mechanical loosening.

Another therapeutic treatment of the facet joint is to affix the superior articular process to the inferior articular process using a facet screw. Although the fixation therapy may alleviate symptoms associated with a degenerated facet joint, it also sacrifices some of the ability of the motion segment to move and thus sacrifices some of the ability of the spinal column to move in a natural manner. Central and lateral spinal stenosis (joint narrowing), degenerative spondylolisthesis, and degenerative scoliosis may all result from the abnormal mechanical relationship between the anterior and posterior column structures and induce debilitating pain.

More recently, a percutaneously-implantable, facet joint stabilization device has been developed, and is described in U.S. application Ser. No. 12/238,196 (filed Sep. 25, 2008 and entitled "Method and Apparatus for Facet Joint Stabilization"), the teaching of which are incorporated herein by reference. The facet joint stabilization device generally entails a superior body and an inferior body that, when combined, form an exteriorly threaded device. When inserted into the joint space, the inferior and superior bodies establish an engaged relationship with the corresponding inferior and superior bony faces of the facet joint anatomy, respectively, and are somewhat slidable relative to one another to facilitate near normal facet joint motion ability. While viable, areas for improvement remain, including retention, long-term functioning, and insertion techniques.

In light of the above, a need exists for additional therapies applicable to facet joints to stabilize and augment the facet joint in alleviating problems without initial resort to the more radical therapies of replacing the facet joint with a prosthesis and/or fixation of the facet joint and the inherent loss of natural movement of that motion segment.

SUMMARY

Some aspects in accordance with the present disclosure relate to a system for treating a facet joint of a patient. The facet joint anatomy includes opposing, superior and inferior articular faces. With this in mind, the system includes a superior resurfacing device and an inferior resurfacing device. The superior resurfacing device has a superior resurfacing body that is configured to selectively transition to a shape conforming to a shape of the superior articular face of the facet joint. Similarly, the inferior resurfacing device includes an inferior resurfacing body configured to selectively transition to a shape conforming to a shape of the inferior articular face of the facet joint. In this regard, each of the resurfacing bodies exhibits sufficient flexibility to transition from a relatively flat state to an inserted state in which the resurfacing body substantially matches any multi-planar curvatures and concavities of the corresponding facet joint articular face in the presence of compressive forces associated with a typical, adult human facet joint. With this construction, the system is capable of establishing a new sliding interface within the facet joint via articulating surfaces of the resurfacing bodies, thereby eliminating the pain-causing, bone-on-bone articular interface associated with the natural anatomy. Further, by conforming with the natural shape associated with the native facet joint articular faces, the system of the present disclosure can be inserted on a minimally-invasive basis, and restructuring (e.g., removal) of the natural bony interface is not required. In some embodiments, the resurfacing bodies are identical, each consisting of a disc-like body having a thickness in the range of 0.25-4 mm. In related embodiments, the resurfacing bodies are formed of polyetherketone (PEK)-based material, such as or polyetheretherketone (PEEK). In yet other embodiments, the resurfacing bodies provide an articulating surface and a plurality of teeth projecting in a direction opposite the articulating surface; the plurality of teeth serve to establish engagement with the corresponding facet joint articular face upon insertion.

Yet other aspects in accordance with principles of the present disclosure relate to methods for treating facet joint pain of a patient, and include inserting a superior resurfacing body into the facet joint and into engagement with the superior articular face of the facet joint articular anatomy. In this regard, the superior resurfacing body transitions from a relatively flat state to an insertion state upon insertion to the facet joint, substantially conforming to a shape of the superior facet joint face in response to compressive forces of the facet joint. An inferior resurfacing body is inserted into the facet joint and into engagement with an inferior facet joint articular face. As part of this insertion, the inferior resurfacing body transitions from a relatively flat state to an insertion state that substantially conforms with a shape of the inferior articular face in response to compressive forces of the facet joint. Upon final insertion, an articulating surface of the superior resurfacing body slidably abuts an articulating surface of the inferior resurfacing body, thereby relieving facet joint pain. In some embodiments, the method is characterized by the absence of surgical removal of normal bone of the facet joint, and the resurfacing bodies are inserted simultaneously via a percutaneous technique.

Yet other aspects in accordance with principles of the present disclosure relate to a kit for treating a facet joint of a patient. The kit includes a treatment system as described above (e.g., a superior resurfacing device having a superior resurfacing body, and an inferior resurfacing device having an inferior resurfacing body), along with an insertion tooling set. The insertion tooling set includes a delivery cannula and an elongate pusher tool. The delivery cannula has a distal end and defines an internal passage that is open at the distal end. The pusher tool is sized to be slidably received within the passage. With this construction, the kit is configured to provide an insertion arrangement in which the resurfacing devices and the pusher tool are slidably received within the passage, with the resurfacing devices being stacked against one another adjacent the distal end and a distal region of the pusher tool abutting the resurfacing devices opposite the distal end of the cannula. In some embodiments, the resurfacing devices each form a notch sized to receive a finger formed by the pusher tool to achieve selective engagement therebetween.

BRIEF DESCRIPTION OF THE DRAWINGS

FIG. 3A is a top view of a resurfacing device component of the system of FIG. 2;

FIG. 3B is a cross-sectional view of the resurfacing device of FIG. 3A, taken along the line 3B-3B;

FIG. 3C is an enlarged view of a portion of the device of FIG. 3B, taken along the line 3C;

FIG. 3D is a front view of the resurfacing device of FIG. 3A;

FIG. 9 illustrates accessing a facet joint in preparation for subsequent resurfacing device insertion into the joint in accordance with principles of the present disclosure;

FIGS. 10A-10C illustrate use of optional dilator and sheath instruments in accordance with the present disclosure;

FIGS. 11A-11C illustrate deployment of the facet joint treatment system of FIG. 2 within a facet joint using the tooling set of FIG. 5;

FIG. 12A is a top plan view of another resurfacing device useful with facet joint treatment systems in accordance with principles of the present disclosure;

FIG. 12B is a side view of the resurfacing device of FIG. 12A;

FIG. 12C is a front view of the resurfacing device of FIG. 12A;

FIG. 13A is a top plan view of another resurfacing device useful with facet joint treatment systems in accordance with principles of the present disclosure;

FIG. 13B is a side view of the resurfacing device of FIG. 13A;

FIG. 13C is a front view of the resurfacing device of FIG. 13A;

FIG. 14A is a top plan view of another resurfacing device useful with facet joint treatment systems in accordance with principles of the present disclosure;

FIG. 14B is a side view of the resurfacing device of FIG. 14A;

FIG. 14C is a front view of the resurfacing device of FIG. 14A;

FIG. 15A is a top plan view of another resurfacing device useful with facet joint treatment systems in accordance with principles of the present disclosure;

FIG. 15B is a side view of the resurfacing device of FIG. 15A;

FIG. 15C is a front view of the resurfacing device of FIG. 15A;

FIG. 18A is a top plan view of another resurfacing device useful with facet joint treatment system in accordance with principles of the present disclosure;

FIG. 18B is a side view of the resurfacing device of FIG. 18A;

FIG. 21A is a side view of another facet joint treatment system in accordance with principles of the present disclosure;

FIG. 21B is a front view of the system of FIG. 21A;

FIG. 21C is a top plan view of the system of FIG. 21A;

DETAILED DESCRIPTION

Figure 1:
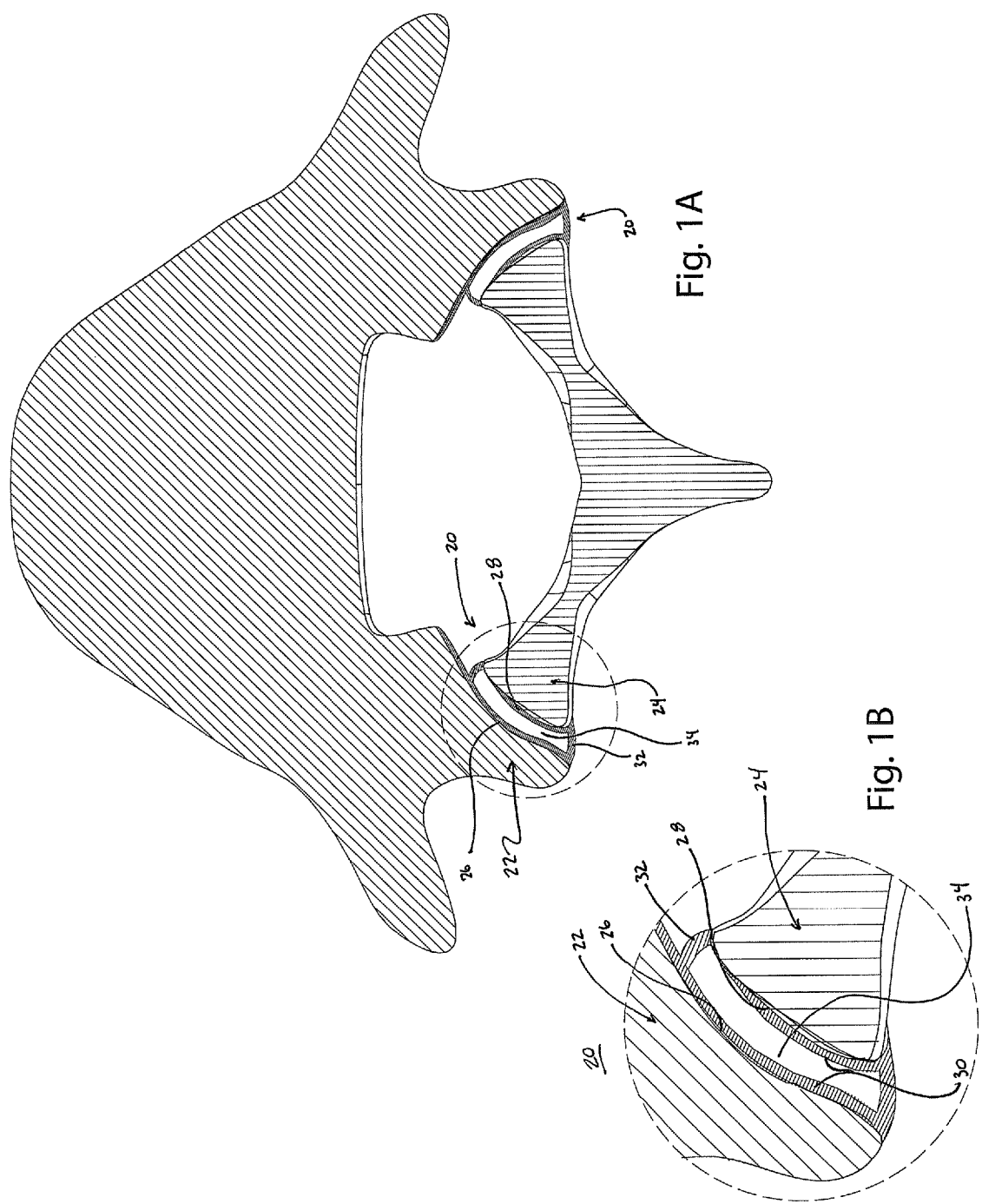
FIG. 1A is a simplified cross-sectional view of a human spinal segment illustrating anatomy of native facet joints with which the systems and methods of the present disclosure are useful in treating.
FIG. 1B is an enlarged view of one facet joint of the segment of FIG. 1A.
Figure 2:
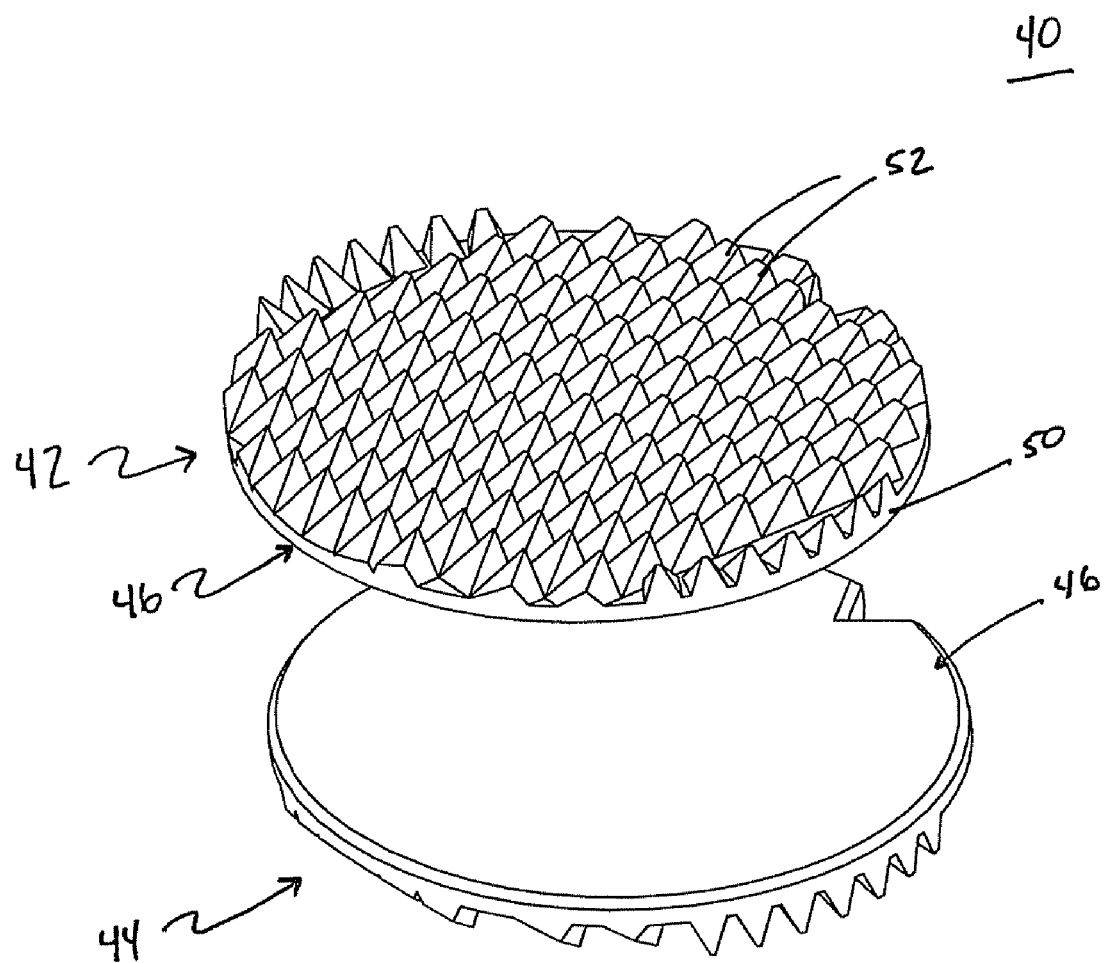
FIG. 2 is a perspective view of a facet joint treatment system in accordance with principles of the present disclosure.

One embodiment of a system 40 in accordance with principles of the present disclosure and useful for treating a facet joint of a patient is shown in FIG. 2. The system 40 includes a superior resurfacing device 42 and an inferior resurfacing device 44. Details on the various components are provided below. In general terms, however, the resurfacing devices 42, 44 can be identical, with the superior resurfacing device 42 serving as a liner for a superior facet joint articular face (e.g., the superior articular face 26 of FIG. 1B), and the inferior resurfacing device 44 serving as a liner for an inferior facet joint articular face (e.g., the inferior articular face 28 of FIG. 1B). The resurfacing devices 42, 44 are capable of substantially conforming to the naturally-occurring shape or curvature of the facet joint anatomy, and replace the existing, bone-on-bone interface of the natural facet joint in a manner achieving normal or near normal mobility.

As indicated above, in some constructions, the resurfacing devices 42, 44 can be identical. Thus, the following description of the superior resurfacing device 42 is equally applicable to the inferior resurfacing device 44. With additional reference to FIGS. 3A and 3B, the resurfacing device 42 consists of a resurfacing body 46. In other embodiments described below, one or more additional components can be attached to, or extend from, the resurfacing body 46. Regardless, the resurfacing body 46 has a disc-like shape, and includes a base web 50 and a plurality of teeth 52 (referenced generally). The base web 50 defines opposing major surfaces 54, 56 (best shown in FIG. 3B), with the first major surface 54 providing or serving as an articulating surface (e.g., articulates relative to a corresponding articulating surface of the inferior resurfacing device 44 (FIG. 2)) as described below. Thus, the first major surface 54 can also be referenced as the "articulating surface" of the resurfacing body 46. The plurality of teeth 52 project from the second major surface 56 in a direction generally opposite the first major surface 54.

With specific reference to FIG. 3A, the base web 50 defines an outer perimeter 58 (referenced generally) of the resurfacing body 46, with the perimeter 58 having an oval-like shape (relative to a top or bottom plan view) in some constructions. More particularly, the perimeter 58, and thus the resurfacing body 46, defines a major diameter MA along a major axis thereof, and a minor diameter MI along a minor axis thereof. An overall size or footprint of the resurfacing body 46 is defined by the perimeter 58 and can vary depending upon a size of the facet joint being treated, but is generally relatively small, especially as compared to conventional facet joint prostheses and/or capping devices. For example, the major diameter MA can be in the range of 5-12 mm, and the minor diameter MI can be in the range of 4-10 mm in some embodiments. Even further, facet joint treatment systems in accordance with the present disclosure can be provided to a treating clinician with two or more different superior resurfacing devices 42 (and two or more different inferior resurfacing devices 44) each having a differently-sized resurfacing body 46 (e.g., 5 mm×4 mm; 8 mm×6 mm; 10 mm×8 mm; 11 mm×9 mm; 12 mm×10 mm, etc.), with the treating clinician selecting the most appropriately sized resurfacing device for implantation based upon an evaluation of the facet joint to be treated. Alternatively, other dimensions are also envisioned by the present disclosure. Further, the perimeter 58 need not necessarily be oval in shape. Instead, other shapes (e.g., circular, square, rectangular, curvilinear, etc.) are also acceptable.

For reasons made clear below, the resurfacing body 46 can incorporate one or more features dictating a preferred insertion orientation and/or direction (i.e., the resurfacing body 46 is more readily inserted into, and subsequently retained within, a facet joint in a particular orientation). Relative to the configuration of FIG. 3A, then, the perimeter 58 can be described as generally defining a leading or distal end 70, a trailing or proximal end 72, and opposing sides 74, 76. The minor diameter MI intersects the leading and trailing ends 70, 72, whereas the opposing sides 74, 76 are aligned along the major diameter MA. During an insertion procedure, the resurfacing body 46 is oriented such that the leading end 70 is initially inserted into the facet joint, followed by the trailing end 72. In addition to the teeth 52 having a structure corresponding with these designations (and thus the intended insertion direction and orientation described below), the trailing end 72 can form or define an engagement feature 80 (referenced generally) that promotes desired interaction with a separately-provided insertion tool (not shown) described below. For example, the engagement feature 80 can be a notch 82 formed in the base web 50 at the trailing end 72. Where provided, the notch 82 can assume various shapes, and in some constructions, is defined as a 90° cut into the base web 50. The notch 82 can have shapes differing from that illustrated, and the engagement feature 80 can assume other formats that may or may not include the notch 82. In yet other embodiments, the engagement feature 80 is omitted.

With specific reference to FIG. 3B, the base web 50 has, in some constructions, a relatively uniform thickness t (e.g., nominal thickness variation of +/−0.05 mm). Regardless, the base web 50 forms the articulating surface 54 to be highly smooth. This smoothness attribute is, at least in part, a function of the material employed for the resurfacing body 46 as described below. In other embodiments, the articulating surface 54 of the base web 50 can be coated with a separate layer that provides enhanced frictional (i.e., lower coefficient of friction) and wear characteristics.

The plurality of teeth 52 project from the second major surface 56 of the base web 50, and can assume a variety of forms. In some embodiments, the teeth 52 are arranged to form or define discrete zones or teeth sets, such as the teeth sets 90, 92, 94 generally identified in FIG. 3A. The first teeth set 90 is centrally located along the base web 50 extending between the leading and trailing ends 70, 72. Individual teeth of the first teeth set 90 are generally identical, with a leading tooth 96a of the first teeth set 90 being shown in greater detail in FIG. 3C. More particularly, the tooth 96a includes a leading face 98 and a trailing face 100 that extend from the second major surface 56 and intersect at a tip 102. The leading face 98 is more proximate the leading end 70 (as compared to the trailing face 100), whereas the trailing face 100 is more proximate the trailing end 72 (FIG. 3B). With these designations in mind, the tooth 96a is constructed to define an insertion direction whereby an angle α formed by the leading face 98 relative to the second major surface 56 is less than an angle β formed by the trailing face 100 relative to the second major surface 56. That is to say, the leading face 98 has a more gradual slope relative to the leading end 70 as compared to a slope of the trailing face 100 relative to the trailing end 72 such that the tooth 96a more overtly engages a separate structure, such as the facet joint superior face (not shown) at and along the trailing face 100 as compared to the leading face 98. In some constructions, the angle α defined by the leading face 98 is in the range of 20°-60°, whereas the angle β defined by the trailing face 100 is approximately 90°. Other angles are also acceptable. Regardless, and returning to FIG. 3A, the remaining teeth of the first teeth set 90 are aligned with one another in two or more rows as shown.

The second teeth set 92 and the third teeth set 94 are formed at or along the opposing sides 74, 76, respectively. In this regard, while the individual teeth of the second and third sets 92, 94 can have the non-symmetrical relationship described above with respect to the tooth 96a (FIG. 3C), an exterior face 104a, 104b and an interior face 105a, 105b associated with each tooth of the second and third teeth sets 92, 94 establish an angle of extension relative to the second major surface 56 that approaches 90° as best shown in FIG. 3D in some embodiments. With this but one acceptable construction, the second and third teeth sets 92, 94 overtly resist side-to-side displacement of the resurfacing body 46 relative to a corresponding facet joint face following insertion (e.g., relative to the orientation of FIG. 3D, the second teeth set 92 resists leftward displacement of the resurfacing body 46, whereas the third teeth set 94 resists rightward displacement).

As illustrated in FIG. 3D, the second set of teeth 92 each have an exterior face 104a that faces the first opposing side 74 and an interior face 105a that faces the second opposing side 76. An angle formed between the interior face 105a and the base web 50 is less than an angle formed between the exterior face 104a and the base web 50. The third set of teeth 94 each have an exterior face 104b that faces the second opposing side 76 and an interior face 105b that faces the first opposing side 74. An angle formed between the interior face 105b and the base web 50 is less than an angle formed between the exterior face 104b and the base web 50.

In some constructions, each tooth of the plurality of teeth 52 can have an identical, or nearly identical, height (or extension from the second major surface 56). In other embodiments, and in particular the embodiment reflected in FIG. 3B, however, the teeth of the first teeth set 90 have an elevated height as compared to teeth of the second and third teeth sets 92, 94 (FIG. 3A), and combine to define a tapering height of the resurfacing body 46 from the leading end 70 to the trailing end 72. Stated otherwise, and relative to the illustrated embodiment in which the first major surface 54 is planar, a height of the leading tooth 96a is greater than a height of a trailing tooth 96b. For example, the tips 102 associated with the teeth of the first teeth set 90 combine to define a hypothetical plane P. The plane P is, in some embodiments, non-perpendicular relative to a plane of the first major surface 54, combining with the first major surface 54 to define an included angle Δ in the range of 1°-5°. Alternatively, other angles are also contemplated; in yet other embodiments, the teeth 52 have identical heights. With the one configuration of FIG. 3B, however, the tallest tooth 96a is provided at the leading end 70 that ultimately is located opposite the point of insertion into the facet joint. As a result, the leading tooth 96a can desirably establish a more rigid engagement with the corresponding facet joint face to thereby overtly resist displacement upon final insertion.

The base web 50 and the teeth 52 combine to define an overall thickness T of the resurfacing body 46 (e.g., lateral distance between the first major surface 54 and the tip 102 of the "tallest" tooth 96a). As described in greater detail below, a desired conformability characteristic of the resurfacing body 46 is influenced by the overall thickness T and the base web thickness t, and thus the overall thickness T is selected, along with other parameters, to effectuate the desired degree of conformability. In some constructions, the overall thickness T of the resurfacing body 46 is in the range of 0.25-4 mm, although other dimensions are also contemplated. As a point of reference, the overall thickness T associated with the resurfacing body 46 selected by the treating clinician for insertion into a particular facet joint may vary as a function of other procedures associated with the insertion. For example, where the resurfacing body 46 is inserted into a facet joint without any overt tissue removal prior to insertion, the overall thickness T can be in the range of 0.5-2.5 mm. If, however, the insertion procedure entails first removing cartilage (or other tissue) from the facet joint, a larger version of the resurfacing body 46 can be inserted, such that the overall thickness T of the resurfacing body 46 is in the range of 0.5-3 mm.

Figure 4A:
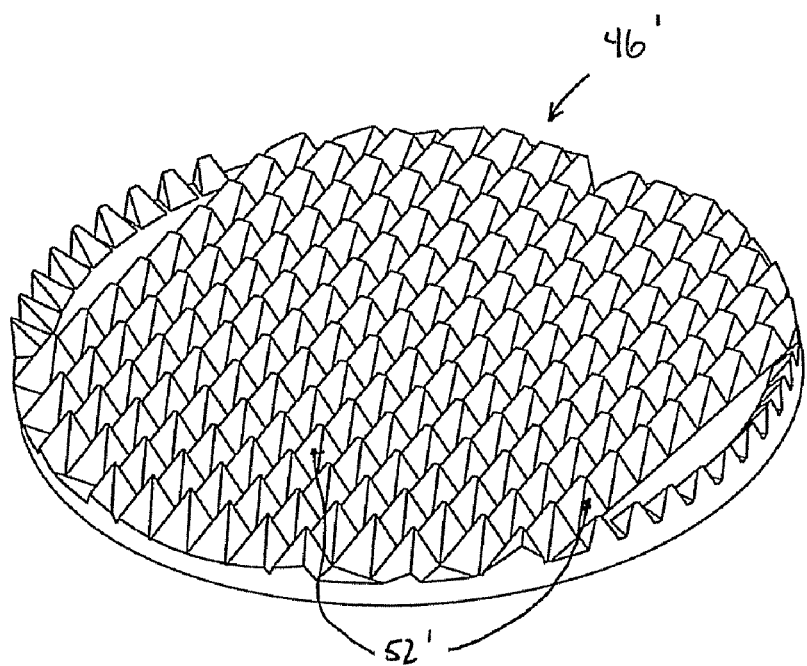
FIG. 4A is a perspective view of an alternative resurfacing device useful with facet joint treatment systems of the present disclosure.
Figure 4B:
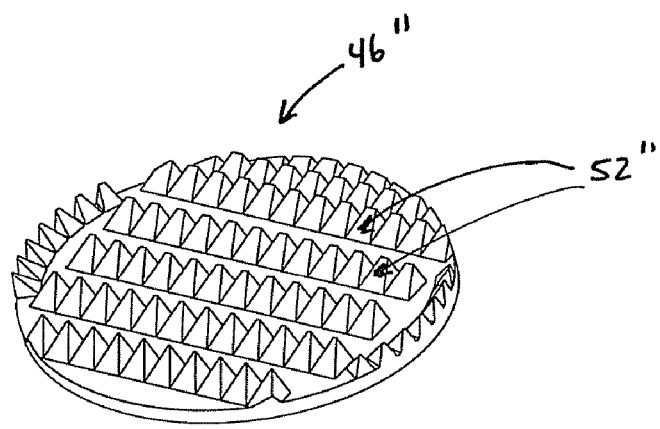
FIG. 4B is a perspective view of another resurfacing device useful with facet joint treatment systems of the present disclosure.

As indicated above, the plurality of teeth 52 can assume a variety of forms differing from those described and illustrated. For example, FIGS. 4A and 4B illustrate alternative resurfacing bodies 46', 46", respectively, in accordance with principles of the present disclosure. As compared to the resurfacing body 46 described above, the resurfacing body 46' of FIG. 4A incorporates an increased number of teeth 52'. With the resurfacing body 46" of FIG. 4B, some of the teeth 52" are arranged in discretely spaced rows. In yet other embodiments, the teeth can be replaced or augmented with other features (e.g., surface textures or coatings) that promote retention in the facet joint, bony in-growth, or both.

Returning to FIG. 2, the resurfacing devices 42, 44, and thus the corresponding resurfacing bodies 46, are each integrally formed of a robust material that achieves desired conformability. The resurfacing body 46 in accordance with the present disclosure maintains its structural integrity (i.e., little or no wear) without adhesive or cohesive damage when subjected to typical articulation of the facet joint with movement of the patient. In some constructions, the resurfacing devices 42, 44 are formed of an implantable-grade plastic, although other materials such as metal are also available. For example, the resurfacing devices 42, 44 can be made from the polyetherketone (PEK) family of plastics, which have strength, wear, flexibility, and biocompatibility properties appropriate for insertion into, and long-term functioning within, the facet joint. Polyetheretherketone (PEEK) has surprisingly been found to provide not only the conformability attributes described below, but also long-term mechanical strength and resistance to wear. Additional material(s) can be incorporated, such as those exhibiting radio-opacity properties. For example, the resurfacing devices 42, 44 can be formed from a radio-opaque mineral (e.g., barium)-loaded PEK composition. Visualization can also be provided via one or more radio-opaque marker bands (e.g., platinum marker band). The marker band(s) can be embedded within the resurfacing device 42, 44 (e.g., a radio-opaque rod inserted into a hole formed in the resurfacing device 42, 44); inserted around a perimeter of the resurfacing device 42, 44; etc.

The selected materials, shapes, and dimensions associated with the resurfacing body 46 of each of the resurfacing devices 42, 44 impart or create a conformability property to the resurfacing body 46 sufficient to allow the resurfacing body 46 to "match" the multi-planar concavity associated with a native facet joint articular face anatomy. As a point of clarification, with the resurfacing device 42, 44 embodiment of FIG. 2, the resurfacing body 46 forms an entirety of the corresponding resurfacing device 42, 44. In other embodiments described below, one or more additional components can be included with the resurfacing body 46, such that the following explanation of conformability is specifically applicable to the resurfacing body 46, but may also apply equally to the resurfacing devices 42, 44 as a whole. In general terms, "conformability" is inversely proportional to bending stiffness of the resurfacing body 46 during insertion, and may be increased as the resurfacing body 46 heats to body temperature and is allowed to creep. From a clinical perspective, "conformability" of the resurfacing body 46 entails the resurfacing body 46 conforming to a radius of curvature of the C-shaped or J-shaped portions of the articular joint (e.g., the concave-shaped superior articular face 26 of FIG. 1B or the convex-shaped inferior articular face 28 of FIG. 1B). As a point of reference, the minimum radius of curvature of the human facet joint in the transverse plane is on the order of 20 mm, with a lower bound ($10^{th}$ percentile) on the order of 7 mm. The radius of curvature will vary with the vertebral level and the patient's specific anatomy and disease state. Preparation of the facet joint prior to insertion of the resurfacing devices 42, 44 may also change the radius of curvature. A range of curvature radii of 7 mm to infinity (i.e., flat facet anatomy) can be accommodated by the resurfacing devices 42, 44 of the present disclosure. There also may be curvature in the sagittal plane; the conformable nature of the resurfacing body 46 of the present disclosure is capable of substantially "matching" any sagittal plane curvature as well.

With the above understandings in mind, the conformability characteristic of the resurfacing body 46 is sufficient such that the resurfacing body 46 readily transition from the relatively flat state illustrated in FIG. 2 to an inserted state (not shown but reflected, for example, in FIG. 11D) in which the resurfacing body 46 substantially matches or mimics the naturally-occurring shape (e.g., radius of curvature of curved portions) of the facet joint face to which the resurfacing body 46 is secured. In this regard, the facet joint 20 (FIG. 1B) is subject to, or experiences, various loads that effectuate compressive forces at the region of interface between the superior and inferior articular faces 26, 28 (FIG. 1B). These physiologic forces across the facet joint 20 will vary with activity, posture, body loads, and muscle forces, and tend to be approximately 7-14% of body load when standing. However, in the prone, slightly flexed position during surgery/implantation, these loads may be as little as zero. The intrinsic forces will be generated as the resurfacing device 42, 44 (and thus the corresponding resurfacing body 46) are inserted and the capsule 32 (FIG. 1B) is tensioned; compression of the underlying cartilage and subchondral bone, slight flexion, or laminar strains may result and would accommodate some thickness of the devices 42, 44, but separation/posterior translation of the superior facets would be required to accommodate a large portion of a collective thickness of the devices 42, 44. Compressive loads normal to and across the articular faces 26, 28 will be generated upon separation/posterior translation of the superior facets due to joint capsule tensioning. The conformable nature of the resurfacing body 46 is such that in the presence of these typical compressive forces, the resurfacing body 46 will transition from the relatively flat state to the inserted state in which the resurfacing body 46 substantially matches the geometry of the facet joint surface to which the resurfacing body 46 is secured (i.e., the resurfacing body 46 will flex to conform with a macroscopic shape/contour of the native articular face to which the resurfacing body 46 is applied, but may not conform to the microscopic variations in the native articular face, for example small deviations due to cartilage defects, bony fissures, or small voids during preparation of the joint (typically 0.05-0.5 mm in width)). This will occur as the compressive forces applied by the ends of the hypothetical concave region of one facet articular surface (e.g., the superior articular surface 26) and the center of the corresponding convex surface on the opposing articular facet (e.g., the inferior articular surface 28) generate a bending moment on the resurfacing body 46 that produces strain to conform the resurfacing body 46 to the native anatomy.

As used through this specification, a resurfacing body that conforms to the minimum radius of curvature of an adult human facet joint under normal physiologic forces (e.g., on the order of 180-450 N/mm per segment assuming a net 1 mm posterior shear translation) without deviations from the articular surface to which the resurfacing body is applied of greater than 1 mm is defined as being "conformable" and "substantially matching" the multi-planar curvatures of a facet joint. Alternatively, a resurfacing body sized for placement within an adult human facet joint and exhibiting a Conformability Factor (described below) of not more than 100 N is also defined as being "conformable" and "substantially matching" the multi-planar curvatures of a facet joint in accordance with the present disclosure. In some embodiments, resurfacing bodies in accordance with the present disclosure exhibit a Conformability Factor of not more than 50 N, and in other embodiments not more than 25 N. It has surprisingly been found that forming the resurfacing body 46 (and thus either of the resurfacing devices 42, 44 of the one embodiment of FIG. 2) of PEEK and with the footprint size and thickness dimensions described above achieves the desired conformability characteristics, long-term resistance to wear, and facet joint stabilization following insertion.

Figure 5:
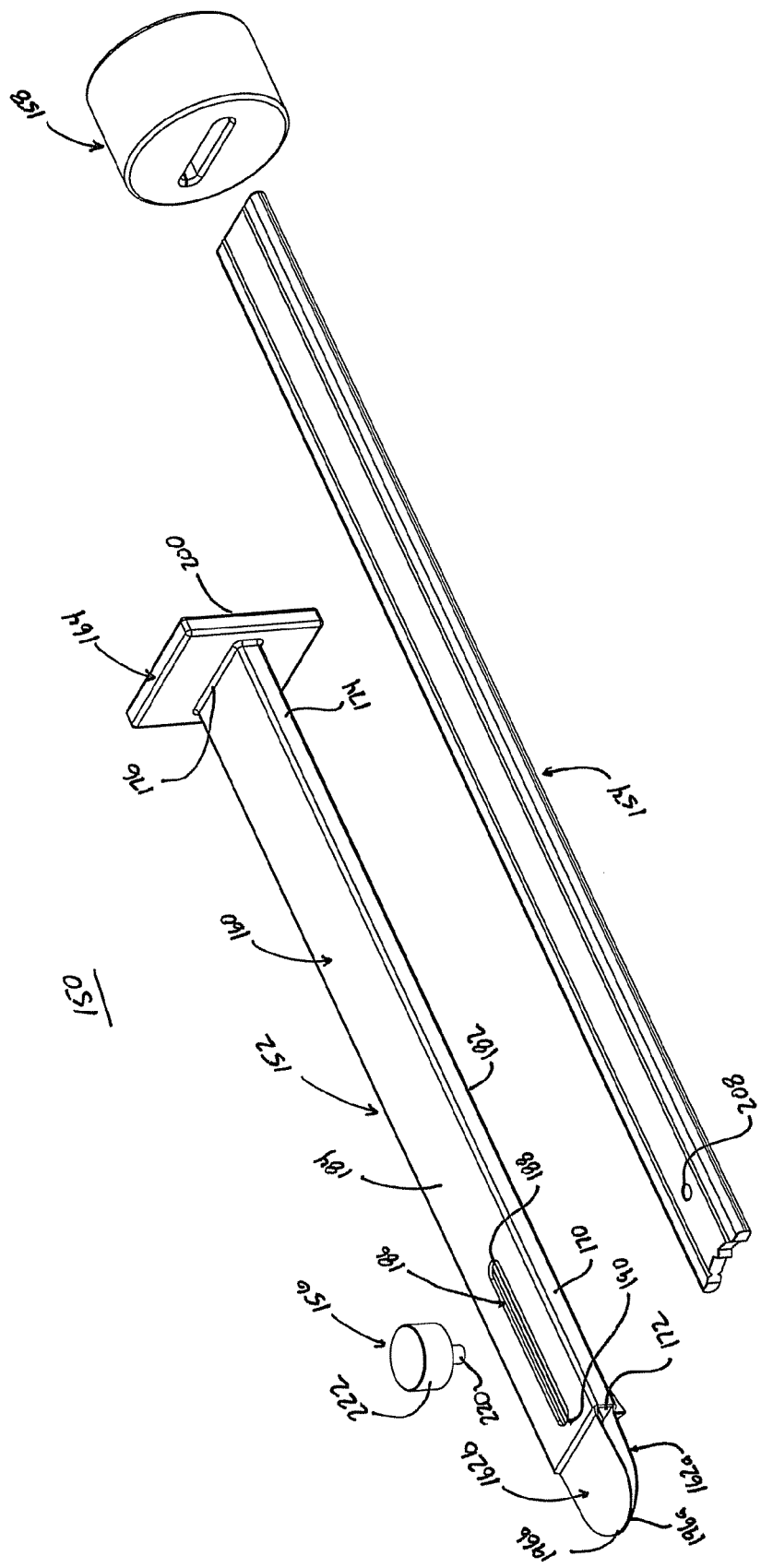
FIG. 5 is a perspective, exploded view of an insertion tooling set useful in inserting the facet joint treatment systems of the present disclosure.

The resurfacing body 46, and thus the system 40, can be delivered to, and inserted within, a facet joint in a variety of manners via various instrumentations sets or systems. Components of one useful insertion tooling set 150 is shown in FIG. 5, and includes a delivery cannula assembly 152 and a pusher tool 154. In general terms, the delivery cannula assembly 152 is sized to slidably receive the pusher tool 154 and the resurfacing devices 42, 44 (FIG. 2), with the cannula assembly 152 and the pusher tool 154 being operable to insert the resurfacing devices 42, 44 into a facet joint. The tooling set 150 can optionally further include a guide pin 156 and a retention cap 158.

The delivery cannula assembly 152 includes, in some constructions, a cannula body 160, guide arms 162a, 162b, and a handle 164. The cannula body 160 forms or defines a distal section 170 terminating at a distal end 172, and a proximal section 174 terminating at a proximal end 176. Finally, the cannula body 160 forms an internal passage 178 (FIGS. 6A and 6B) that extends between, and is open relative to, the distal and proximal ends 172, 176.

Figure 6A:
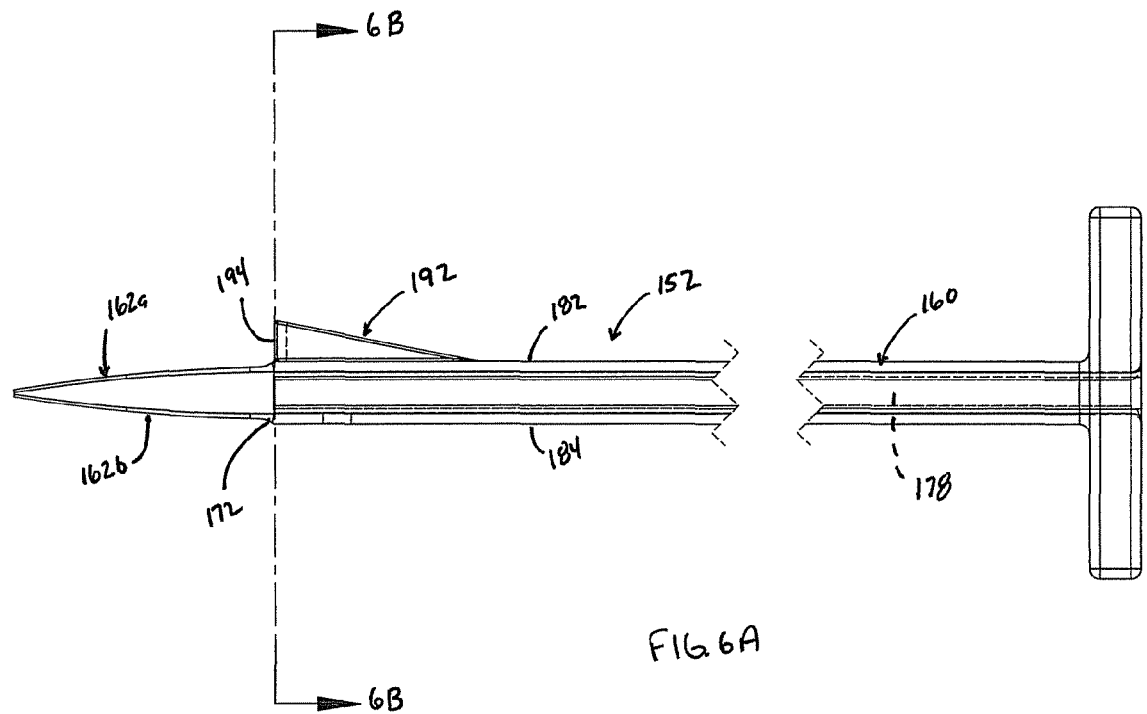
FIG. 6A is a side sectional view of a delivery cannula assembly component of the tooling set of FIG. 5.
Figure 6B:
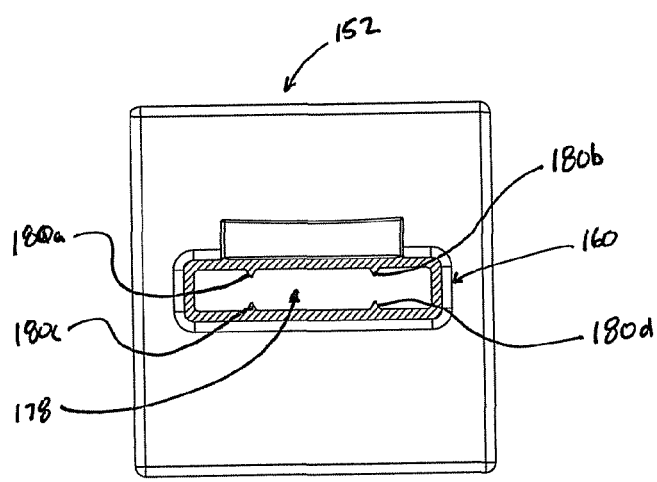
FIG. 6B is a cross-sectional view of the cannula assembly of FIG. 6A, taken along the line 6B-6B.
Figure 6C:
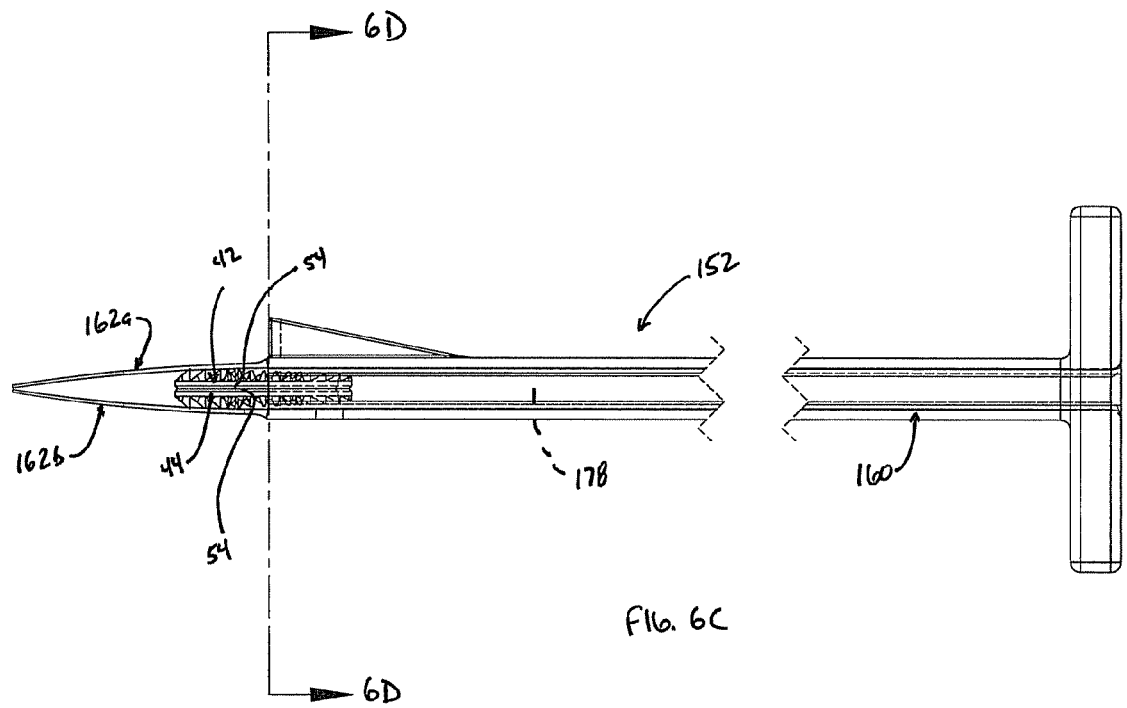
FIG. 6C is a size view of the cannula assembly of FIG. 6A, loaded with the facet joint treatment system of FIG. 2.
Figure 6D:
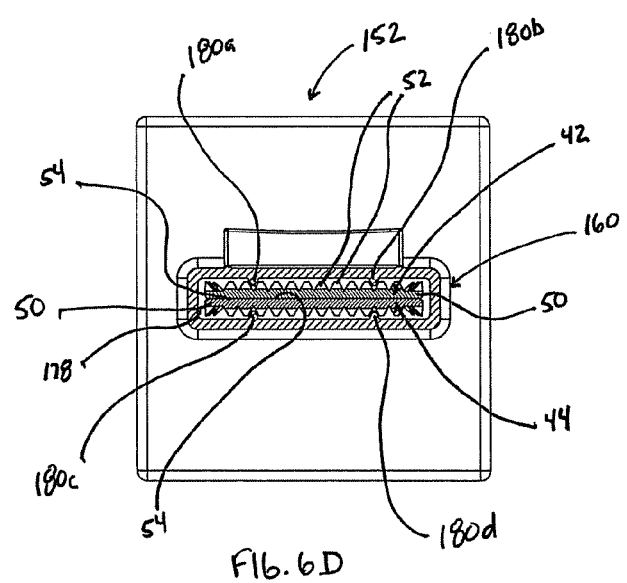
FIG. 6D is a cross-sectional view of the loaded cannula assembly of FIG. 6C, taken along the lines 6D-6D.

With continued reference to FIGS. 6A and 6B, the internal passage 178 is sized and shaped in accordance with a combined size and shape of the resurfacing devices 42, 44 (FIG. 2). More particularly, the internal passage 178 is sized to slidably receive and maintain the resurfacing devices 42, 44 when arranged or stacked against one another in a mirror-like fashion. For example, as shown in FIGS. 6C and 6D, the internal passage 178 is sized and shaped such that the resurfacing devices 42, 44 are maintained therein, with the articulating surface 54 of the superior resurfacing device 42 abutting the articulating surface 54 of the inferior resurfacing device 44. Thus, a height of the internal passage 178 corresponds with, or is slightly greater than, a combined thickness of the resurfacing devices 42, 44. In some constructions, the cannula body 160 forms one or more interior ribs 180 (best shown in FIGS. 6B and 6D) projecting within the internal passage 178. For example, FIG. 6B depicts one embodiment including a pair of spaced-apart upper ribs 180a, 180b and a pair of spaced-apart lower ribs 180c, 180d. Regardless of number and arrangement, the rib(s) 180 extend longitudinally relative to the internal passage 178, and are sized (e.g., in terms of width and distance or length of projection into the internal passage 178) to be slidably received between the teeth 52 of the corresponding resurfacing device 42, 44 (e.g., in some embodiments, various ones of the teeth 52 are aligned with one another to collectively define a channel across the resurfacing device 42, 44 that is sized to slidably receive one of the ribs 180). Thus, and as best shown in FIG. 6D, a horizontal gap between opposing ones of the ribs 180 (e.g., gap between the ribs 180a, 180c) corresponds with, or is slightly greater than, a combined thickness of the base webs 50 of the resurfacing devices 42, 44. With this construction, the ribs 180 serve to guide the resurfacing devices 42, 44 when longitudinally moved through the internal passage 178, thereby preventing undesired rotation thereof.

In addition to the above, the internal passage 178 is defined by a width corresponding with the major diameter MA (FIG. 3A). For example, where the resurfacing devices 42, 44 have a major diameter MA of 11 mm, the internal passage 178 can have a width of approximately 11.7 mm. Other dimensions are also acceptable so long as the resurfacing devices 42, 44 can be slidably retained within the internal passage 178 in the stacked arrangement shown.

Figure 6E:
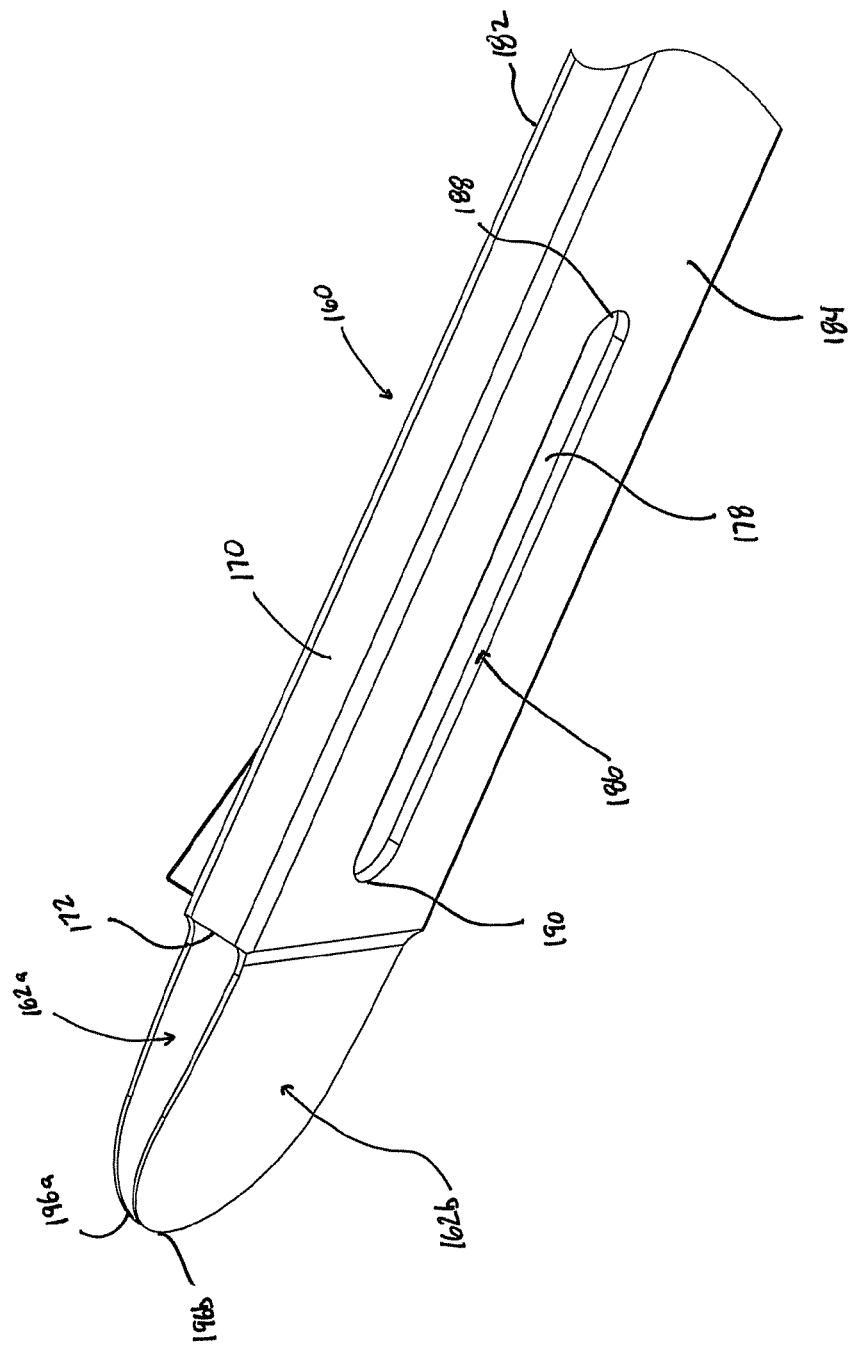
FIG. 6E is an enlarged, top perspective view of a portion of the delivery cannula assembly of FIG. 5.

Returning to FIG. 5, and with additional reference to FIG. 6E, the distal section 170 can include or form one or more features that facilitate desired positioning of the tooling set 150 during use and/or operation thereof. For example, the cannula body 160 can be defined as having a first major surface 182 (also identified in FIG. 6A) and an opposing, second major surface 184. With this in mind, a slot 186 is formed in the distal section 170 along the second major surface 184 in some constructions. The slot 186 is open to the internal passage 178, and extends from, and is open relative to, the distal end 172. The slot 186 extends between and terminates at a proximal side 188 and a distal side 190, and is sized to slidably receive a corresponding component of the pin 156 (FIG. 5) as described below.

In addition to the slot 186, the distal section 170 further provides or forms an optional shoulder 192 along the first major surface 182 as best shown in FIG. 6A. The shoulder 192 can assume a variety of forms differing from those reflected in the drawings, and in more general terms defines an enlarged stop surface 194 at the distal end 172. The stop surface 194 is configured to better ensure desired positioning of the guide arms 162a, 162b relative to a facet joint during an insertion procedure as described below. In other embodiments, the shoulder 192 can be omitted.

Returning to FIG. 6E, the guide arms 162a, 162b are connected to, and extend from, the distal end 172 of the cannula body 160, each terminating at a distal tip 196a, 196b, respectively. The guide arms 162a, 162b are rigid yet flexible (akin to a metal tape), and can deflect away from one another from the natural, pre-insertion arrangement of FIGS. 5 and 6E. With this construction, the guide arms 162a, 162b are readily insertable into a confined space (e.g., a facet joint) with the distal tips 196a, 196b contacting, or nearly contacting, one another at least at the corresponding tips 196a, 196b. Subsequently, as the stacked resurfacing devices 42, 44 (FIG. 6C) are forced between the guide arms 162a, 162b, the distal tips

196a, 196b will splay away from one another, with the guide arms 162a, 162b deflecting at the distal end 172 of the cannula body 160.

The slot 186 can terminate proximal the second guide arm 162b as shown. Alternatively, the second guide arm 162b can form a slot segment that serves as a continuation of the slot 186. An arrangement of the distal side of the slot 186 (e.g., the distal side 190) relative to the distal tips 196a, 196b, as well as a length of the slot 186, are selected to effectuate optimal insertion of the resurfacing devices 42, 44 (FIG. 2) via the cannula assembly 152 and the pusher tool 154 as described below.

Finally, and with specific reference to FIG. 5, the handle 164 extends radially from the proximal end 176 of the cannula body 160. The internal passage 178 (FIG. 6A) extends through, and is open at, a proximal face 200 of the handle 164. As described below, the handle 164 is configured to facilitate not only handling of the tool set 150 by a user, but can also serve to ensure or limit movement of the pusher tool 154 relative to the cannula body 160.

Figure 7A:
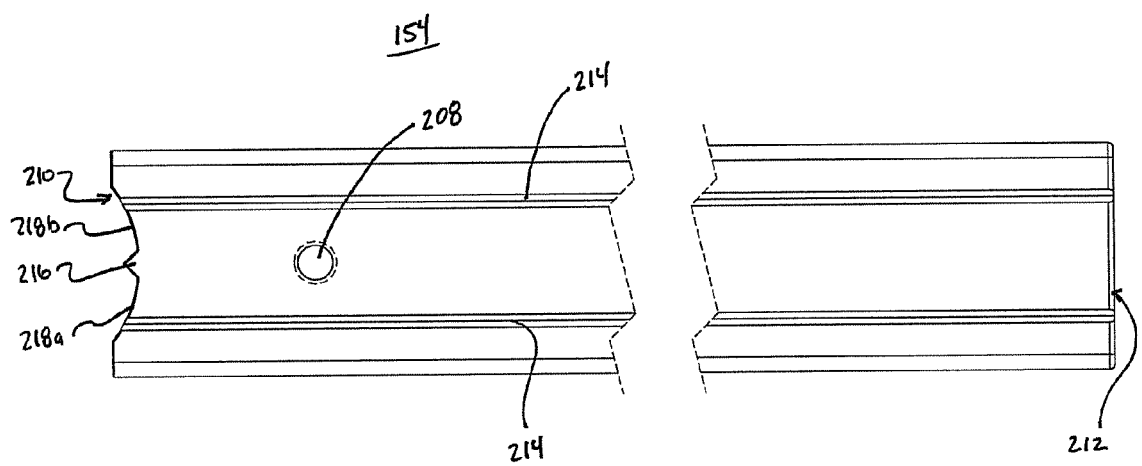
FIG. 7A is a perspective view of a pusher tool component of the tooling set of FIG. 5.

The pusher tool 154 is shown in greater detail in FIG. 7A, and is generally formed as an elongate body forming a hole 208, and defining a distal end 210 and a proximal end 212. The hole 208 is sized to frictionally receive a component of the pin 156 (FIG. 5) as described below, and is formed at a distance from the distal end 210 selected to facilitate deployment of the resurfacing devices 42, 44 (FIG. 2) in a desired fashion. The pusher tool 154 is sized to be slidably received within the internal passage 178 (FIG. 6A) of the cannula body 160 (FIG. 5), and thus has a size and shape corresponding with that of the internal passage 178. With embodiments in which the cannula body 160 forms the interior ribs 180 (FIG. 6B), the pusher tool 154 can form longitudinal channels 214 sized to slidably receive respective ones of the ribs 180.

Figure 7B:
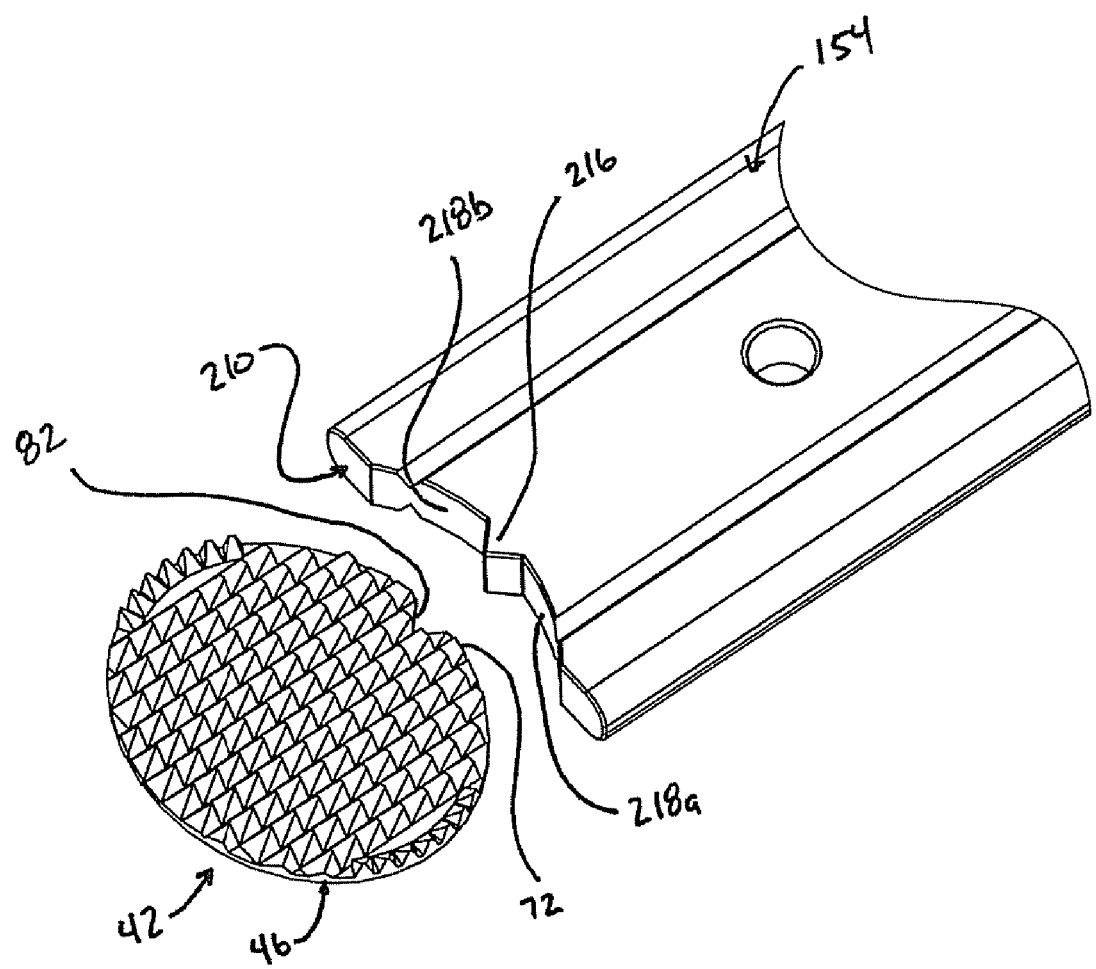
FIG. 7B is an enlarged plan view of a distal portion of the pusher tool of FIG. 7A engaging a resurfacing device in accordance with principles of the present disclosure.

The distal end 210 is configured to interface with the stacked resurfacing devices 42, 44 (FIG. 6D), and in some embodiments can incorporate one or more features that promote a more robust interface with the stacked resurfacing devices 42, 44. For example, the distal end 210 can include or form a central finger 216 defined between opposing grooves 218a, 218b. The finger 216 can assume a variety of shapes and dimensions, and is generally sized in accordance with the notch 82 (FIG. 3A) of the corresponding resurfacing bodies 46. The grooves 218a, 218b, in turn, are generally shaped in accordance with a shape of the trailing end 72 (FIG. 3A) of the resurfacing bodies 46. With this construction, and as shown in FIG. 7B, abutting contact between the distal end 210 and the trailing end 72 of the resurfacing body 46 of the superior resurfacing device 42 (as well as the resurfacing body 46 of the inferior resurfacing device 44 otherwise stacked beneath the superior resurfacing device 42 and thus hidden in FIG. 7B) includes the finger 216 nesting within the notch 82, and the trailing end 72 disposed within the grooves 218a, 218b. With this arrangement, the opportunity for undesired rotation of the resurfacing body 46 relative to the distal end 210 is reduced, yet a sufficient surface area interface between the distal end 210 and the resurfacing body 46 is provided such that the pusher tool 154 can readily be employed to distally move the contacted resurfacing body 46 (and thus the stacked resurfacing devices 42, 44 as a collective unit). In some constructions, the finger 216 is provided with the tool 154 and the notch 82 is formed by the resurfacing bodies 46; alternatively, the resurfacing bodies 46 can include a finger, with the pusher tool 154 forming a corresponding notch. In other embodiments, the finger 216 is configured to provide a more secure (but releasable) attachment between the pusher tool 154 and the resurfacing devices 42, 44 so that the devices 42, 44 can be both pushed and pulled relative to the pusher tool 154 (and thus relative to the facet joint being resurfaced).

Returning to FIG. 5, the optional guide pin 156 includes a shaft 220 and a grip 222. The shaft 220 is sized to be insertable through the slot 186 (e.g., a diameter of the shaft 220 is less than a width of the slot 186), and to be received and frictionally retained at the hole 208 in the pusher tool 154. The grip 222 is dimensioned to be larger than the slot 186 (e.g., the grip 222 cannot pass through the slot 186), with a length of the shaft 220 being greater than a thickness of the cannula body 160 wall at which the slot 186 is formed. With this construction, the shaft 220 can be inserted through the slot 186 (e.g., manually by a user otherwise grasping the pin 156 at the grip 222) and engaged with the pusher tool 154. With sliding of the pusher tool 154 relative to the cannula body 160, then, the shaft 220 slides within the slot 186; upon contacting the distal side 190, the shaft 220 prevents further distal movement of the pusher tool 154. The guide pin 156 can be removed from the pusher tool 154/cannula body 160 by manually retracting the shaft 220 from the hole 208. Alternatively, the shaft 220 can be formed as a permanent projection from the pusher tool 154, and the separate guide pin 156 eliminated.

Figure 8A:
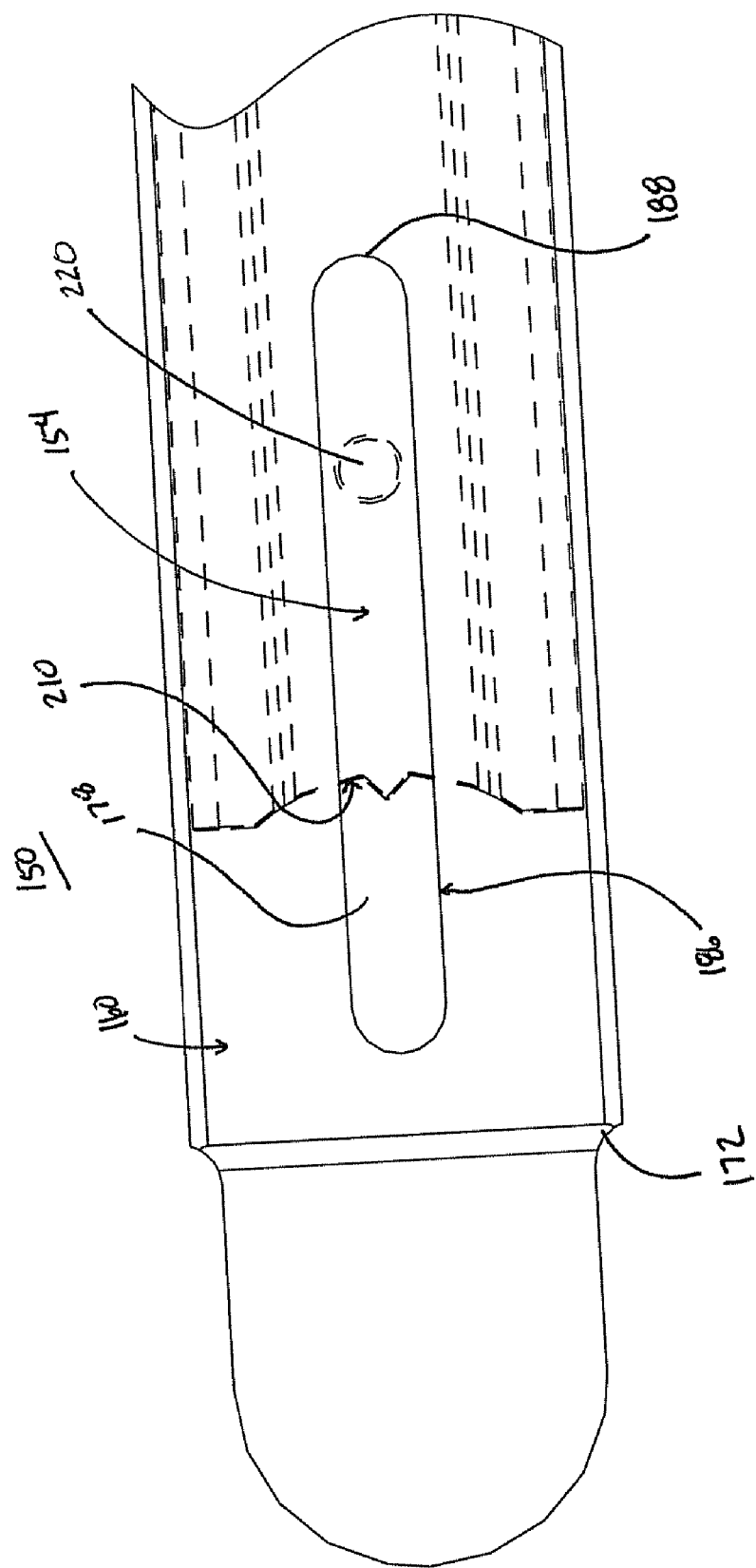
FIGS. 8A-8C illustrate loading and operation of the tooling set of FIG. 5 in deploying the facet joint treatment system of FIG. 2.

Prior to an insertion procedure, the tooling set 150 is loaded with the resurfacing devices 42, 44 (FIG. 2). In particular, the pusher tool 154 is slidably disposed within the internal passage 178 (FIG. 6B) of the cannula body 160, with the shaft 220 being slidably disposed within the slot 186 as shown in FIG. 8A (for purposes of explanation, the grip 222 (FIG. 5) of the pin 156 (FIG. 5) is omitted). For ease of explanation, loading of the pusher tool 154 is described as occurring prior to loading of the resurfacing devices 42, 44. In some embodiments, however, the resurfacing devices 42, 44 are initially placed into the internal passage 178, followed by the pusher tool 154. The proximal end 212 (FIG. 5) of the pusher tool 154 projects outwardly (proximally) beyond the proximal face 200 (FIG. 5) of the handle 164 (FIG. 5). Further, the pusher tool 154 is arranged relative to the cannula body 160 such that the shaft 220 is located adjacent the proximal side 188 of the slot 186. The distal end 210 of the pusher tool 154 is thus spaced from the distal end 172 of the cannula body 160. Once located within the delivery cannula assembly 152, the pusher tool 154 can be captured relative thereto via the cap 158 (FIG. 5) or other structure mounted to the proximal end 212. The cap 158 provides an enlarged surface for grasping by a user for subsequent manipulation of the pusher tool 154 relative to the cannula body 160. Where the pin 156 is retractable from the pusher tool 154 and the cannula body 160, the stacked resurfacing devices 42, 44 and the pusher tool 154 can be inserted into the cannula body 160 proximally via the distal end 172, or distally via the proximal end 176 (FIG. 5).

Figure 8B:
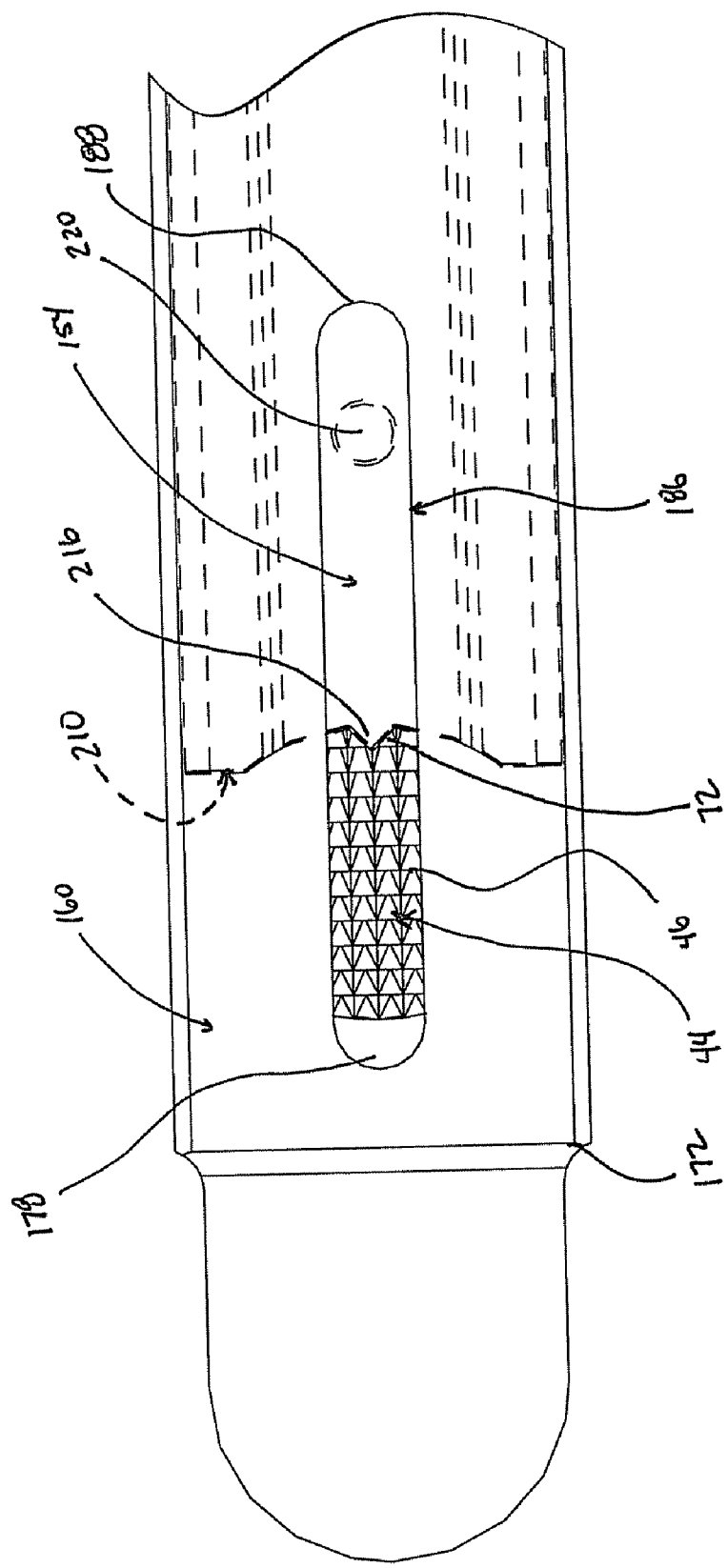

The stacked resurfacing devices 42, 44 are inserted into the internal passage 178 of the cannula body 160 as shown in FIG. 8B (as well as FIGS. 6C and 6D). In this regard, the stacked resurfacing devices 42, 44 (one of which is partially visible in FIG. 8B through the slot 186) can be inserted through the distal end 172, and slid proximally toward the distal end 210 of the pusher tool 154. The distal end 210 engages the trailing end 72 of the corresponding resurfacing bodies 46 as described above, with the resurfacing devices 42, 44 thus being located or disposed completely within the cannula body 160. More particularly, in some embodiments, a distance between the proximal side 188 of the slot 186 and the distal end 172 of the cannula body 160 is less than, or approximates, a combination of a length of the stacked resurfacing devices 42, 44 and a distance between the distal end 210 of the pusher tool 154 and the shaft 220. Thus, with the pusher tool 154 located such that the shaft 220 is at the proximal side 188 of the slot 186, abutment of the resurfacing bodies 46 with the distal end 210 of the pusher tool 154 ensures that the resurfacing devices 42, 44 are fully retained within the cannula body 160.

Figure 8C:
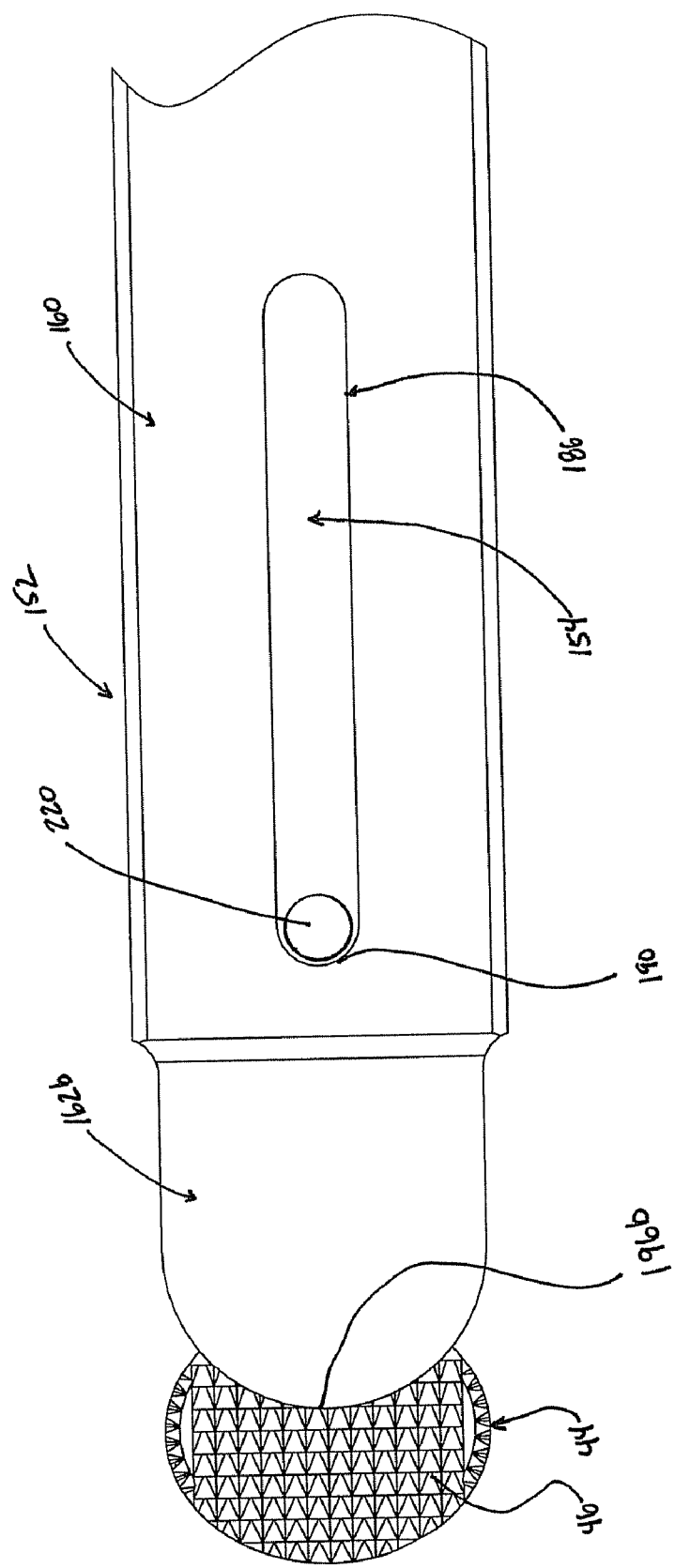

During an insertion procedure, the pusher tool 154 is moved distally relative to the delivery cannula assembly 152, with the shaft 220 is sliding within the slot 186. As shown in FIG. 8C, distal-most movement of the pusher tool 154 relative to the delivery cannula assembly 152 is achieved with the shaft 220 abutting the distal side 190 of the slot 186. In this regard, a distance between the distal tips 196a, 196b of the guide arms 162a, 162b (it being understood that only the lower guide arm 162b and the corresponding tip 196b are visible in the view of FIG. 8C) and the distal side 190 of the slot 186 corresponds with a distance between the finger 216 (hidden in FIG. 8C, but visible in FIG. 7B) and the shaft 220 such that with the shaft 220 at the distal side 190, at least a majority of the resurfacing bodies 46 (one of which is visible in FIG. 8C) are forced distally beyond the distal tips 196a, 196b. Thus, in the deployed position of FIG. 8C, the resurfacing bodies 46 are essentially (but not completely) deployed from the tooling set 150. Engagement of the shaft 220 with the distal side 190 of the slot 186 prevents further distal movement of the pusher tool 154 relative to the cannula body 160. Thus, over-deployment of the resurfacing bodies 46 distally beyond the tooling set 150 (and perhaps beyond the facet joint 20) is prevented.

The tooling set 150 described above is but one possible configuration envisioned by the present disclosure and otherwise useful in deploying the resurfacing devices 42, 44 within a facet joint. Other tooling sets and/or components can be employed as part of an insertion procedure. In fact, the assemblies, tools, and methods described in this disclosure are not limited to a specific method of access to the posterior of a motion segment facet joint. For example, as compared with therapies provided to lumbar facets, cervical facets may require a different operative approach (for example, posterior approach versus a posterior lateral approach) as well as modified access and preparation tool and resurfacing body dimensions, because of coronal angulation. In addition, it will be understood that while for convenience the exemplary tools as described in this disclosure are generally linear and rigid, it is in fact anticipated that to facilitate certain joint therapies and operative approaches, some or all of the instrumentation systems may be configured in whole or in part as needed and appropriate to be either or both curvilinear or flexible.

In accordance with certain facet joint treatment methodology of the present disclosure, precautions are indicated in access and preparation of surgical sites, including use of an imaging system, e.g., bi-planar fluoroscopy, to help maintain interior/posterior and lateral alignment and facilitate surgery, and use of instrumentation with marking indicia in increments in millimeter as appropriate numbers to facilitate accuracy, and in particular with respect to the accurate placement and alignment of the resurfacing bodies 46 within the facet joint.

In some exemplary methods of the present disclosure, the patient is placed in the prone position and x-ray imaging equipment is set-up to provide views in both the antero-posterior (AP) plane and the lateral plane so that the procedure can be performed under fluoroscopic guidance. With reference to FIG. 9, using fluoroscopy or image guidance, access to the facet joint 20 capsule and inter-articular space is achieved by advancing a guide wire or needle 250 through the soft tissue and docking a tip 252 of the guide wire 250 into the facet space 20 at a point corresponding with an end of the joint's principal articulating access. Contrast material may be injected to confirm the location of the guide wire 250, especially at first, but with experience, confirmation of appropriate guide wire placement can be made by feel and by viewing antero-posterior and lateral projections. Relative to the patient, it is typical for the clinician to work from cephalad to caudal in the lumbar spine and caudal to cephalad in the cervical spine. The joint access tract formed between the point of skin entry and docking at an end of the facet joint 20 is typically at the facet joint 20 to be resurfaced, but can alternatively initiate one to two motion segment levels apart from the point of entry into the facet joint 20 of the planned resurfacing to allow for optimal insertion trajectory and placement. In patients with more advanced degenerative changes, osteophytes on the posterior facets may be removed to provide better visualization, to help define the anatomy of the facets, and to provide a suitable surface to allow for therapies as set forth in this disclosure.

Access to and preparation of a posterior target site on the spine, such as the posterior of the L5-S1 segment facet joints, and subsequent deployment therapy, e.g., the deployed resurfacing devices described above, may be performed following percutaneous entry, e.g., by means of a stab incision (the location of the incision may vary, dependent on individual patient anatomy), and by means of subsequent insertion of instrumentation systems including guide wire, dilators, cannulas, insertion tooling sets, as described herein.

In the context of the present disclosure, the term "percutaneous" means through the skin from an access point on the patient and to the posterior target point, as in transcutaneous or transdermal, without implying any particular procedure from other medical arts. However, percutaneous is distinct from an open surgical access, and the percutaneous opening in the skin is preferably minimized so that it is less than 4 cm across, preferably less than 2 cm. The percutaneous pathway is generally aligned with the bore extending from the posterior target point through and into the facet joint 20 and into the articular space, as visualized by radiographic or fluoroscopic equipment.

Figure 10A:
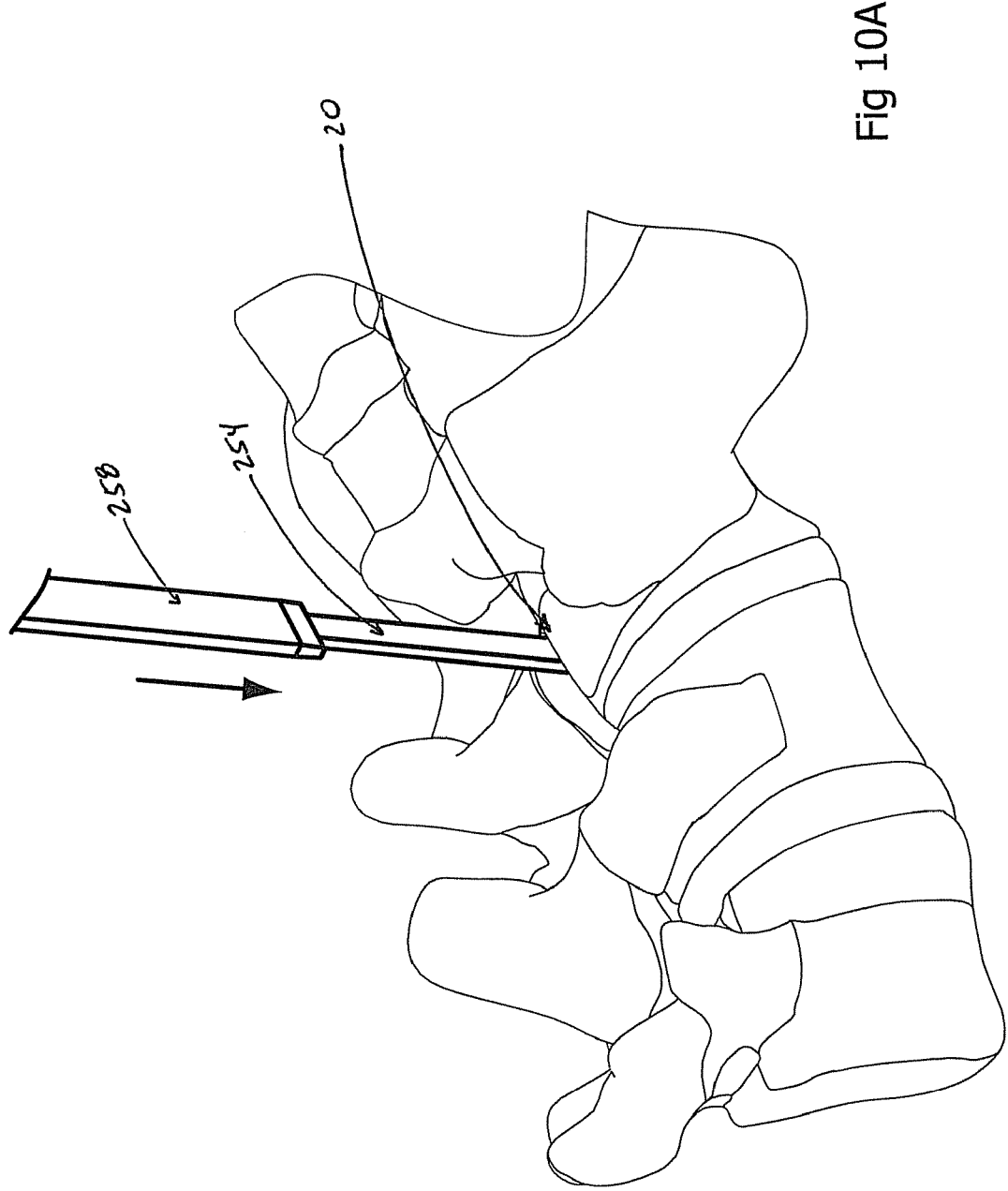
Figure 10B:
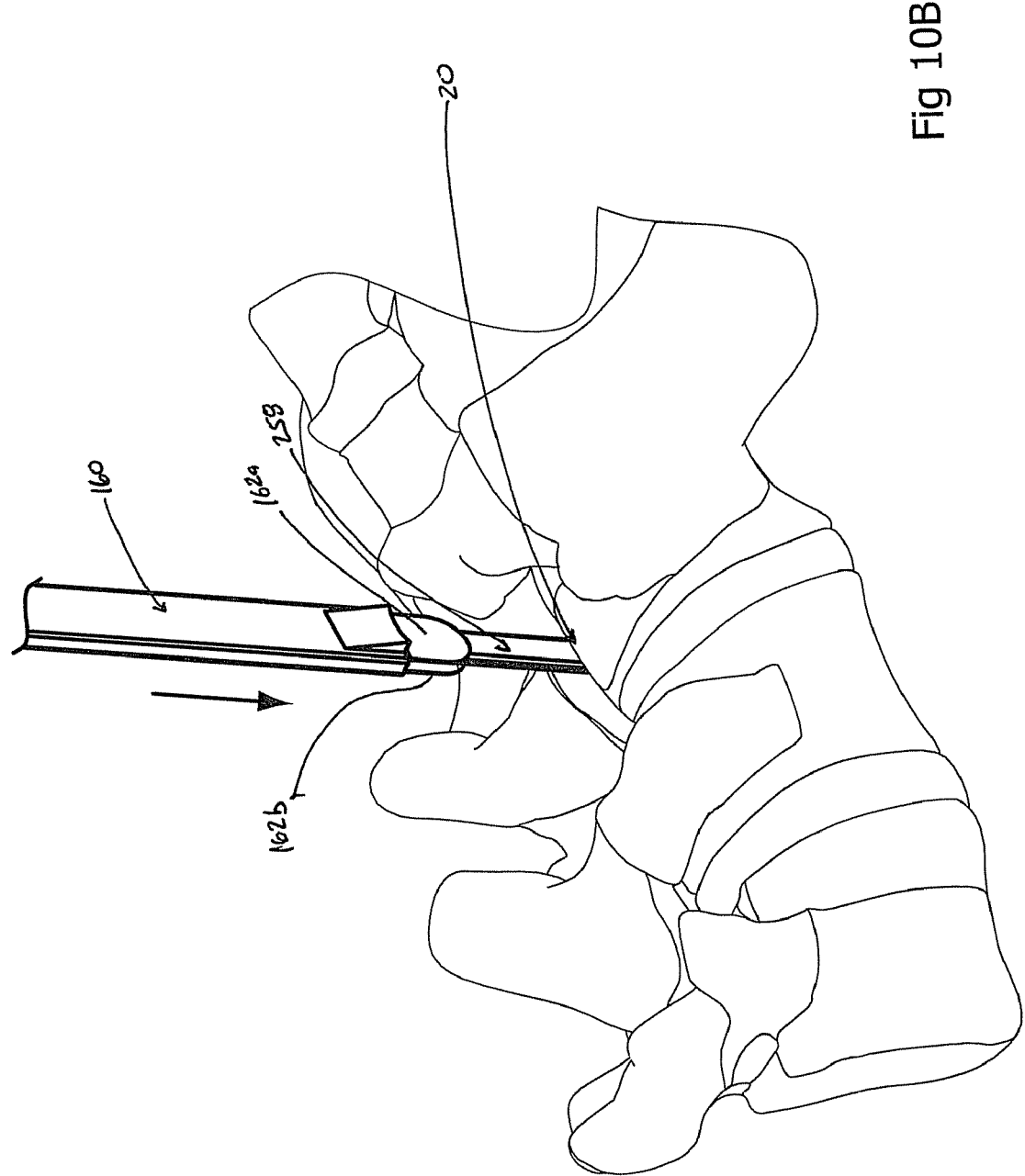

Once the facet joint 20 is located, adjustments are made to achieve optimal trajectory through the joint capsule and into the articular space, which is again verified in both AP and lateral planes using the fluoroscope. A cannulated dilator 254 having a conical, tapered distal end 256 is advanced over the guide wire 250 into the point of entry in the facet joint 20 to create subcutaneous space for the working channel. A hammer or mallet can be used to dock the cannulated dilator 254 into the facet joint 20. It will be understood, for example as needed for other anatomically located joint therapies, this process may be sequentially repeated as needed, i.e., by subsequently inserting a larger diameter cannulated dilator to successively enlarge the access tract. An enlarged guide cannula 258 can optionally be inserted over the cannulated dilator 254 and into the facet joint 20 as shown in FIG. 10A. Upon un-docking and removal of the cannulated dilator 254 from within the guide cannula 258 and back over the guide wire 250 (FIG. 9) and out of the patient, the guide cannula 258 is temporarily left in place to serve as a working cannula that provides a protective portal through the soft tissue access tract to the operative site and about which subsequent instruments can be delivered through the intravenous soft tissue to the target facet joint 20. For example, in FIG. 10B, the cannula body 160 can be inserted over the guide cannula 258, distally directing the guide arms 162a, 162b into the facet joint 20. Distal movement continues until the shoulder 192 contacts a vertebral structure as shown in FIG. 10C. The guide cannula 258 (FIG. 10B) is retracted from the cannula body 160, and the treatment system 40 (FIG. 2) and the pusher tool 154

(FIG. 5) loaded into the cannula body 160 as described below. In other embodiments, an outer guide cannula within which the cannula body 160 is inserted can be utilized in place of the guide cannula 258.

In some embodiments, a channel into and across the facet joint 20 can be formed by removing cartilage or other tissue via a drill, burr, or hand tool (not shown) deployed over the guide wire 250 (FIG. 5). In other embodiments, however, removal of tissue from the facet joint 20 is not performed or required as part of the resurfacing system insertion procedure. That is, as compared to facet joint prosthesis implantation and/or capping procedures, methods of the present disclosure are significantly less time consuming and traumatic in that tissue (e.g., bone) removal and/or facet joint articular face restructuring (e.g., the superior and/or inferior articular faces 26, 28 of FIG. 1B) is not necessary. Furthermore, by not overtly disrupting the articular faces 26, 28, the likelihood of undesired fusion between the faces 26, 28 is greatly reduced.

Figure 11A:
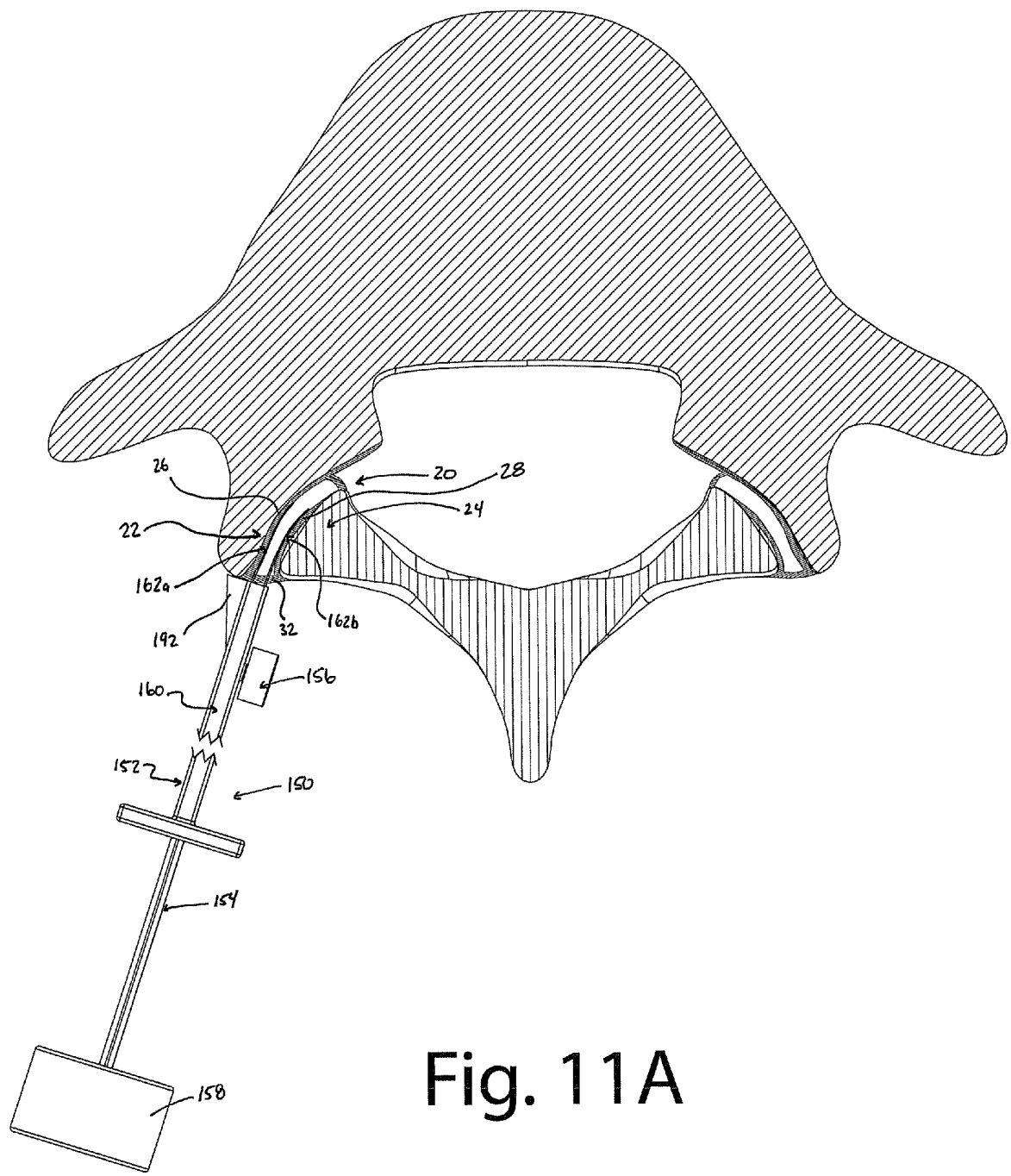

Regardless of whether tissue removal steps are performed, with the cannula body 160 in place, the guide cannula 258 is removed. As shown in FIG. 11A, the cannula body 160 has been directed to the facet joint 20, with the guide arms 162a, 162b sliding along and between the superior and inferior articular faces 26, 28 of the facet joint 20 (and conforming to the curvatures thereof). Distal deployment of the tooling set 150 continues until the shoulder 192 contacts the joint capsule 32 (and/or bone surrounding the joint capsule 32). Thus, the shoulder 192 serves to prevent overt movement or placement of the guide arms 162a, 162b outside of or beyond the facet joint 20 (opposite the point of entry). The resurfacing devices 42, 44 (hidden in FIG. 11A) are loaded into the cannula body 160, along with the pusher tool 154. The pusher tool 154 is captured relative to the cannula body 160 via the pin 156 and the cap 158 as described above.

Figure 11B:
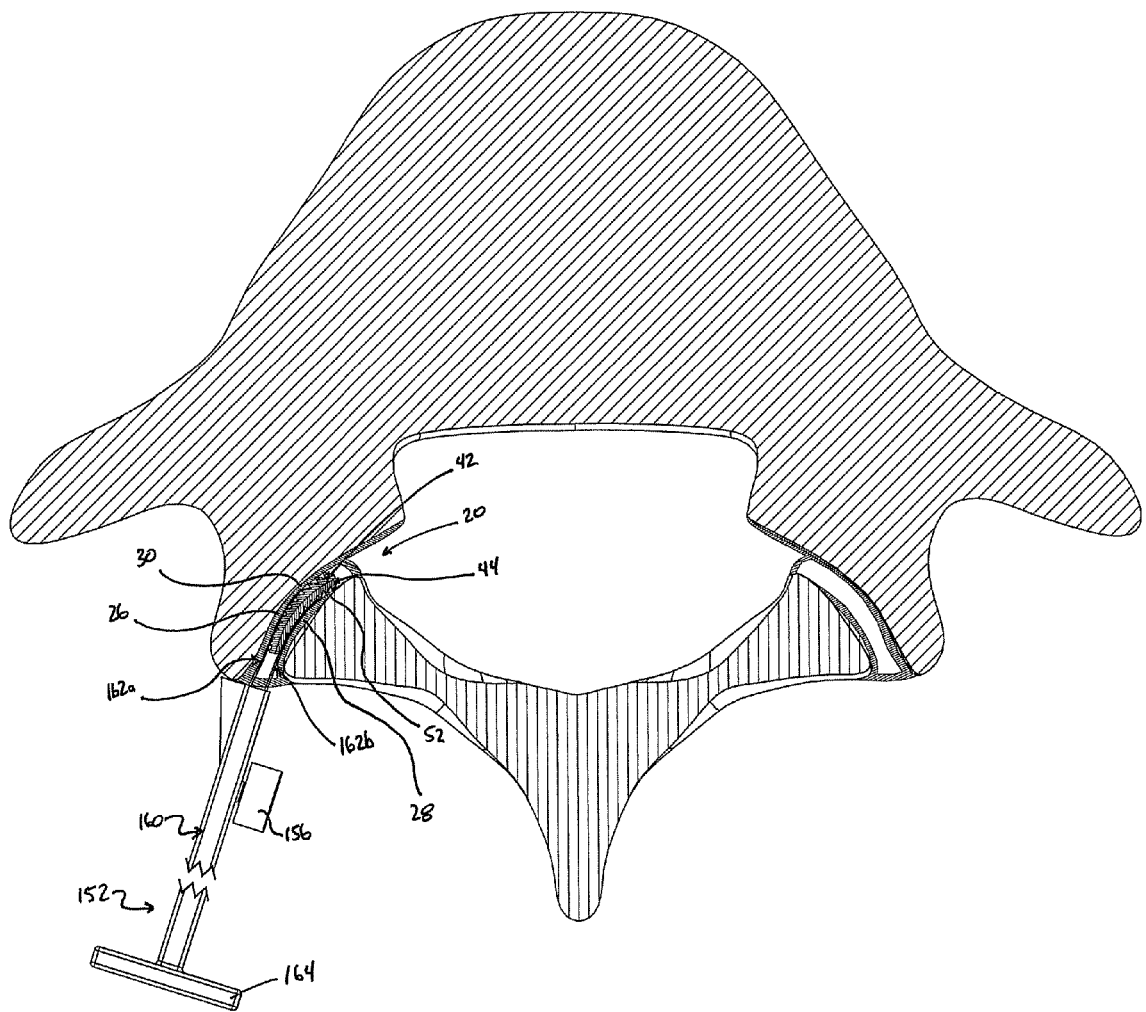

The pusher tool 154 is then driven distally relative to the delivery cannula assembly 152, thereby deploying the resurfacing devices 42, 44 from the cannula body 160, along the guide arms 162a, 162b, and into the facet joint 20 as shown in FIG. 11B (for ease of illustration, the pusher tool 154 is omitted from the view of FIG. 11B). The insertion orientation of the teeth 52 as described above is such that the teeth 52 do not overtly impede insertion of the corresponding resurfacing body 46 in the direction shown (i.e., the angled orientation of the teeth 52 corresponds with the direction of insertion such that the teeth 52 slide along the corresponding articular surface 26, 28). As described above with reference to FIG. 8B, distal movement of the pusher tool 154 is constrained by the pin 156 contacting the distal side 190 of the slot 186 and/or by the cap 158 (FIG. 5) contacting the handle 164. At the end of the distal movement of the pusher tool 154, a portion of the resurfacing bodies 46 are distally beyond the distal ends 196a, 196b of the guide arms 162a, 162b. The so-exposed teeth 52 embed with the corresponding articular surfaces 26, 28 (e.g., the cartilage 30 covering the surfaces 26, 28) in a direction opposite the direction of insertion, such that as the tooling set 150 (and in particular the cannula body 160) is subsequently withdrawn (e.g., the guide arms 162a, 162b refracted from the facet joint 20), the guide arms 162a, 162b slide over the corresponding resurfacing device 42, 44, and the resurfacing devices 42, 44 remain in place within the facet joint 20 as shown in FIG. 11C.

Figure 11D:
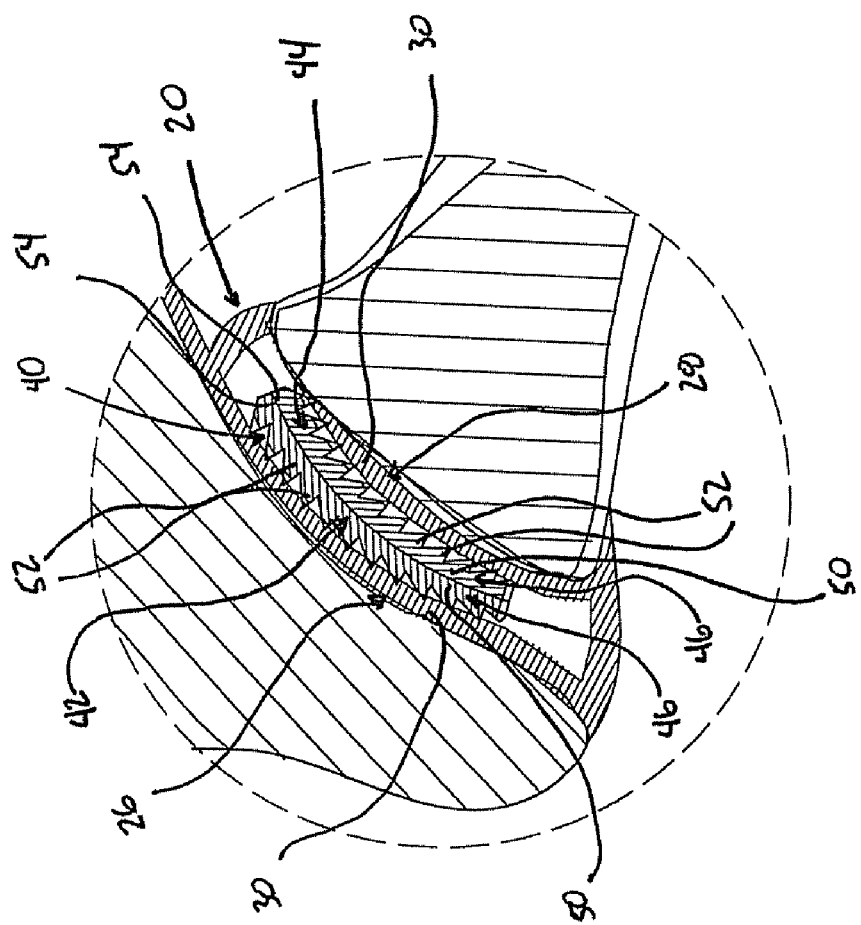
FIG. 11D is an enlarged, cross-sectional view of a facet joint within which the treatment system of FIG. 2 has been inserted.

Final placement of the facet joint treatment system 40 within the facet joint 20 is reflected in FIG. 11D. The teeth 52 of the superior resurfacing device 42 frictionally engage the superior articular face 26 of the facet joint 20 (e.g., the cartilage 30 covering the superior articular face 26), whereas the teeth 52 of the inferior resurfacing device 44 frictionally engage the inferior articular face 28 (e.g., the cartilage 30 covering the inferior articular face 28). Further, each of the corresponding resurfacing bodies 46 transitions from the pre-insertion, relatively flat state to the inserted state shown in which the resurfacing bodies 46 substantially match or conform with the macroscopic geometry or contour (e.g., multi-planar curvature(s)) of the corresponding articular surfaces 26, 28. Stated otherwise, in response to the normal compressive force associated with the facet joint 20, the resurfacing body 46 of the superior resurfacing device 42 conforms with or substantially matches the complex shape of the superior articular face 26; the resurfacing body 46 of the inferior resurfacing device 44 similarly conforms with or substantially matches the shape of the inferior articular face 28. Also, a sliding interface is established between the articulating surfaces 54 of the resurfacing bodies 46, thereby providing normal or near-normal facet joint motion while eliminating painful, bone-on-bone interaction. More particularly, the articulating surface 54 of the superior resurfacing device 42 bears against, and is slidable relative to, the articulating surface 54 of the inferior resurfacing device 44. A combined thickness of the base webs 50 re-establishes a near normal articular spacing of the facet joint 20, enhancing overall stability of the facet joint 20. Where desired, additional facet joint treatment systems 40 can be inserted into other facet joints of the patient.

Facet joint treatment benefits of the present disclosure can be achieved with facet joint treatment systems differing from those described above. For example, FIGS. 12A-12C illustrate another embodiment resurfacing device 300 in accordance with principles of the present disclosure. As a point of reference, a second resurfacing device (not shown) that can be identical to the resurfacing device 300 is also provided in forming a facet joint treatment system as described above. With this in mind, the resurfacing device 300 is similar to the resurfacing devices 42, 44 (FIG. 2) previously described, and is comprised of a resurfacing body 302 having a base web 304 and a plurality of teeth 306. The base web 304 defines a first major surface 308 that serves as an articulating surface upon final insertion. The plurality of teeth 306 project from an opposing, second major surface 310 of the base web 304, and have the pattern and orientations shown. Following insertion of the resurfacing body 302, the teeth 306 frictionally and/or mechanically engage a native facet joint articular surface, thereby securing the resurfacing device 300 within the facet joint.

Yet another embodiment resurfacing device 330 useful as part of a facet joint treatment system in accordance with principles of the present disclosure is shown in FIGS. 13A-13C. The resurfacing device 330 is akin to the resurfacing devices 42, 44 (FIG. 2) previously described, and consists of a resurfacing body 332 having a base web 334 and a plurality of teeth 336. Once again, the base web 334 forms or defines a first major surface 338 that serves as an articulating surface upon final insertion to the facet joint. The plurality of teeth 336 project from a second major surface 340 of the base web 334, and have the pattern and orientation shown. As with previous embodiments, upon insertion, the teeth 336 frictionally and/or mechanically engage a native facet joint articular surface, thereby securing the resurfacing device 330 to the facet joint.

Yet another embodiment resurfacing device 350 useful as part of a facet joint treatment system in accordance with principles of the present disclosure is shown in FIGS. 14A-14C. The resurfacing device 350 is akin to the resurfacing devices 42, 44 (FIG. 2) previously described, and consists of a resurfacing body 352 having a base web 354 and a plurality of teeth 356. The base web 354 forms a first major surface 358 that serves as an articulating surface upon final insertion to the facet joint. The teeth 356 project from a second major surface 360 of the base web 354. With the configuration of FIGS. 14A-14C, the second major surface 360 forms a series of ridges 362. The teeth 356 project beyond the ridges 362, and serve to establish a robust, aggressive interface with a native facet joint articular face. Further, the ridges 362 provide additional resistance to "back out" or retropulsion of the resurfacing body 352 upon insertion to the facet joint.

A related embodiment resurfacing device 380 useful as part of a facet joint treatment system in accordance with the present disclosure is shown in FIGS. 15A-15C. The resurfacing device 380 consists of a resurfacing body 382 having a base web 384 forming a first major surface 386 that serves as an articulating surface upon final insertion to a facet joint. With the embodiment of FIGS. 15A-15C, the articulating surface 386 is convex. An opposing, second major surface 388 of the base web 384 forms a series of ridges 390 having the orientation shown. More particularly, the ridges 390 have an angular orientation that facilitates easy insertion of the resurfacing body 382 along a native facet joint articular surface, but overtly resist "back out" of the resurfacing body 382 following insertion. Finally, the base web 384 can form one or more holes 392 that provide attachment to a separation insertion instrument (not shown).

Figure 16A:
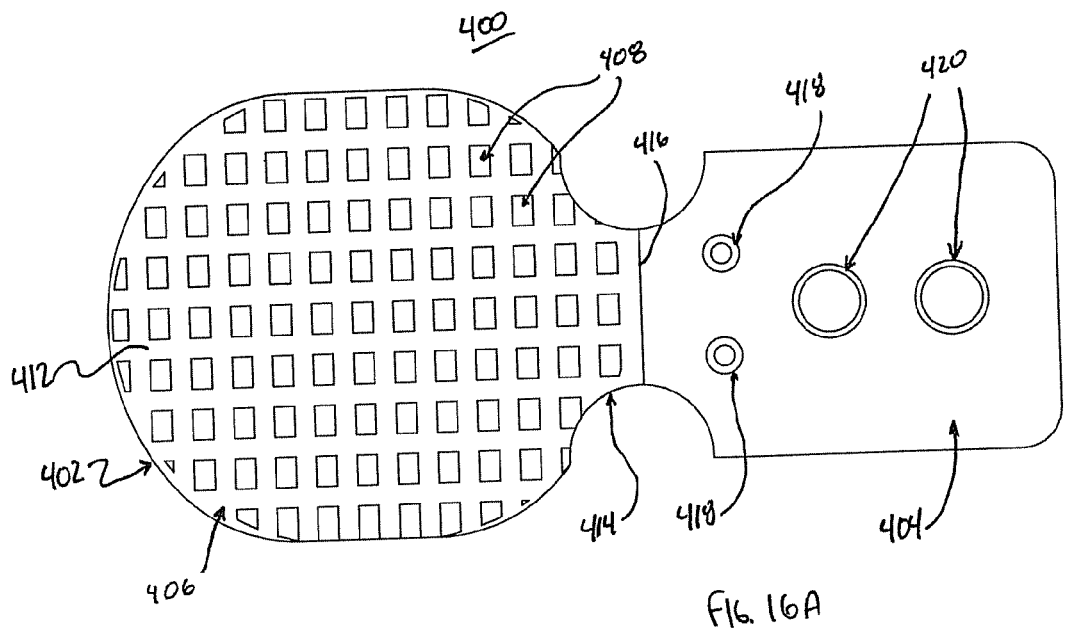
FIG. 16A is a top plan view of another resurfacing device useful with facet joint treatment systems in accordance with principles of the present disclosure.
Figure 16B:
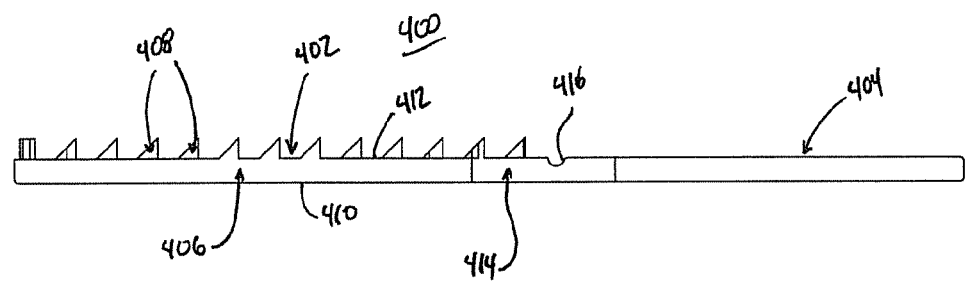
FIG. 16B is a side view of the resurfacing device of FIG. 16A.

While the resurfacing bodies described above have relied upon teeth and/or ridges to effectuate securement to a native facet joint articular surface, in other constructions, additional attachment features can be provided. For example, FIGS. 16A and 16B illustrate another embodiment resurfacing device 400 useful as part of a facet joint treatment system in accordance with the present disclosure. The resurfacing device 400 includes a resurfacing body 402 and a tab 404. The resurfacing body 402 is akin to any of the resurfacing bodies described above, and thus is sized and shaped for insertion within a facet joint. The tab 404 extends from the resurfacing body 402, and is configured to facilitate additional fixation of the resurfacing device 400 to a facet joint. With this in mind, the resurfacing body 402 includes a base web 406 and a plurality of teeth 408. The base web 406 forms or defines a first major surface 410 that serves as an articulating surface upon final insertion. The teeth 408 project from a second major surface 412 of the base web 406, and can have the pattern and orientation as shown, or any other configuration described above.

The tab 404 can be integrally formed with the resurfacing body 402, for example as a continuation of the base web 406. In some embodiments, a neck region 414 is defined at a transition between the resurfacing body 402 and the tab 404 that allows closure of soft tissues around the resurfacing device 400. Further, a trough 416 can be defined that allows for bending of the tab 404 relative to the resurfacing body 402 and/or serves as a guide for cutting under circumstances in which the tab 404 is not desired. Regardless, the tab 404 optionally forms suture holes 418 and/or screw holes 420. The suture holes 418 are sized and positioned to allow securement of the tab 404, and thus of the resurfacing device 400, to the facet joint capsule or other surrounding tissue with one or more sutures (not shown). The screw holes 420 are each sized to receive a respective bone screw (not shown) that otherwise affix the tab 404, and thus the resurfacing device 400, into a bony structure at or adjacent the facet joint being treated.

Insertion of the resurfacing device 400 to a facet joint can be performed as described above, and typically entails simultaneous insertion of a stacked arrangement of two of the resurfacing devices 400. Once the resurfacing body 402 is positioned as desired within the facet joint (e.g., the teeth 408 contacting a native facet joint articular surface, and the resurfacing body 402 otherwise conforming with the native facet joint geometry), the tab 404 is mechanically affixed relative to the facet joint being treated via sutures (not shown) threaded through the suture holes 418 and into the joint capsule or other surrounding tissue and/or bone screws placed through the screw holes 420 and into bone. Alternatively, where the additional fixation provided by the tab 404 is not necessary, the tab 404 can simply be removed (e.g., cut) from the resurfacing body 402 as described above.

Figure 17A:
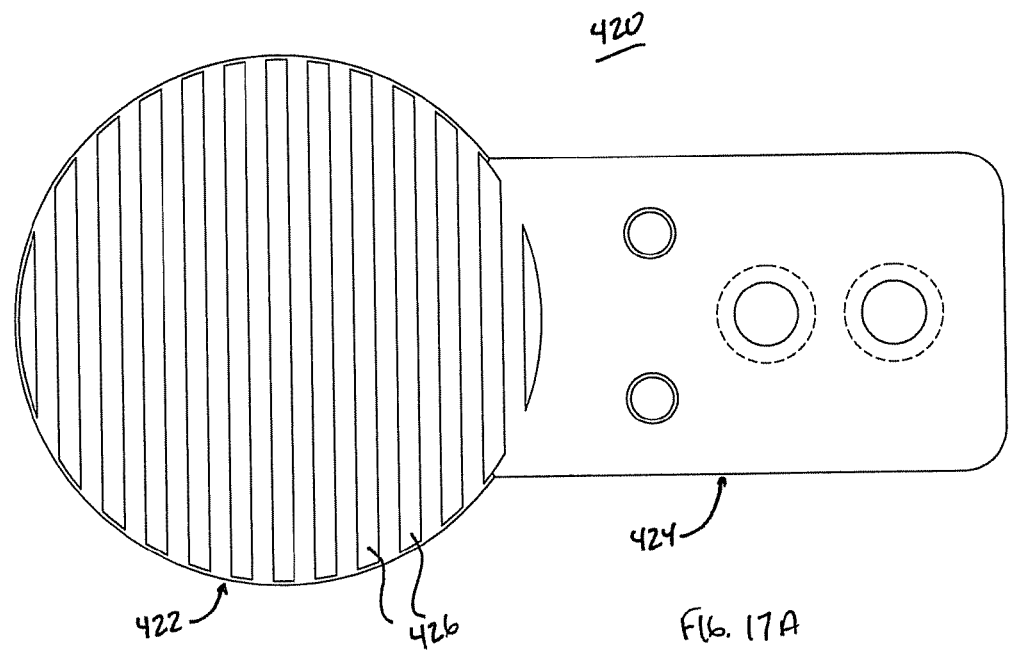
FIG. 17A is a top plan view of another resurfacing device useful with facet joint treatment systems in accordance with principles of the present disclosure.
Figure 17B:
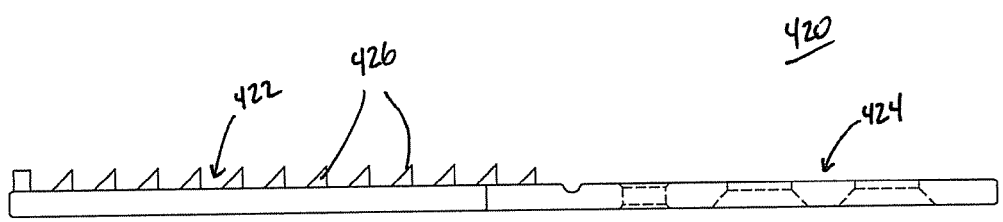
FIG. 17B is a side view of the resurfacing device of FIG. 17A.
Figure 19A:
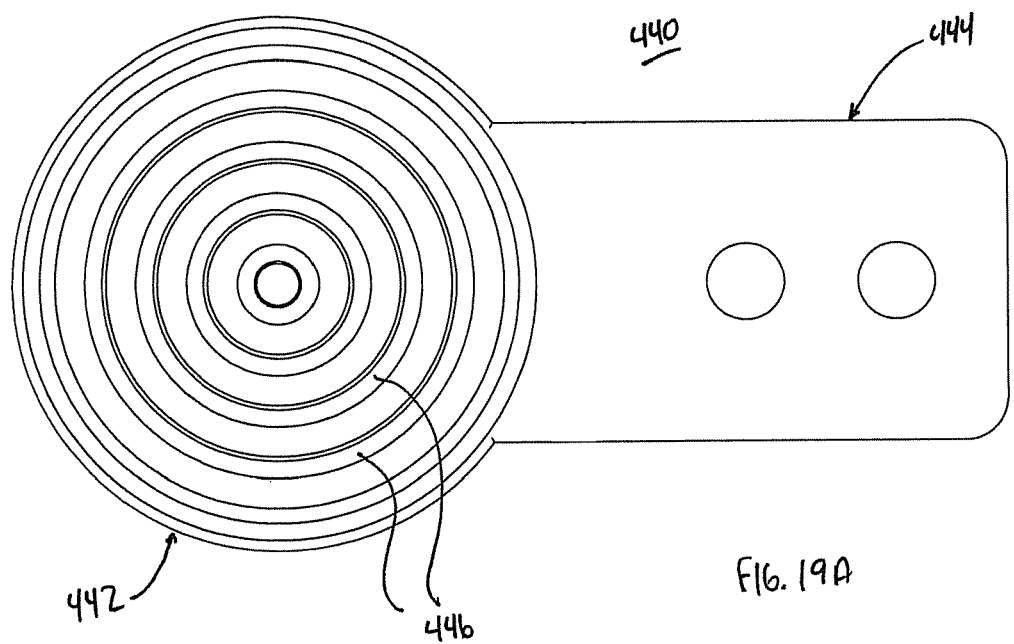
FIG. 19A is a top plan view of another resurfacing device useful with facet joint treatment systems in accordance with principles of the present disclosure.
Figure 19B:
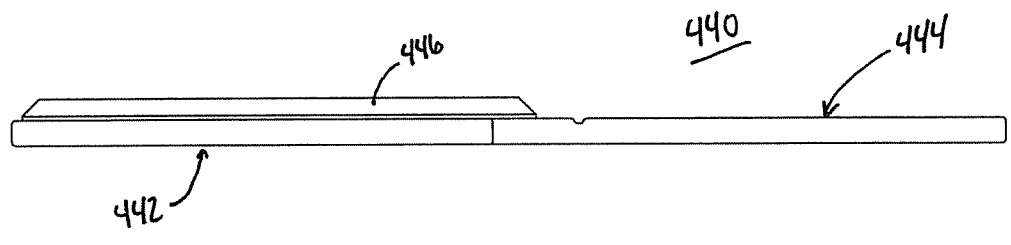
FIG. 19B is a side view of the resurfacing device of FIG. 19A.

The resurfacing body 402 can assume any of the forms described elsewhere in this disclosure (e.g., the resurfacing body 46 of FIG. 2), with the resurfacing device 400 more generally described as providing the optional attachment tab 404. That is to say, the tab 404 (or any other tab component described elsewhere) can be incorporated with any other resurfacing body configuration set forth in this disclosure, and vice-versa. Another example of a resurfacing device 420 akin to the resurfacing device 400 (i.e., including a resurfacing body and additional component(s) that can assist in affixing the device to a facet joint) and useful as part of a facet joint treatment system in accordance with the present disclosure is shown in FIGS. 17A and 17B. The resurfacing device 420 includes a resurfacing body 422 and a tab 424, with the resurfacing body 422 forming or providing ridges 426 as shown. A related embodiment resurfacing device 430 is shown in FIGS. 18A and 18B, and also includes a resurfacing body 432 and a tab 434, with the resurfacing body 432 forming or providing a keel structure 436 having deep fins 438 that create a screw-like surface. Finally, a resurfacing device 440 is shown in FIGS. 19A and 19B, and includes a resurfacing body 442 and a tab 444, with the resurfacing body 442 forming or providing a circular fixation grid 446 that prevents migration in all directions.

Figure 20A:
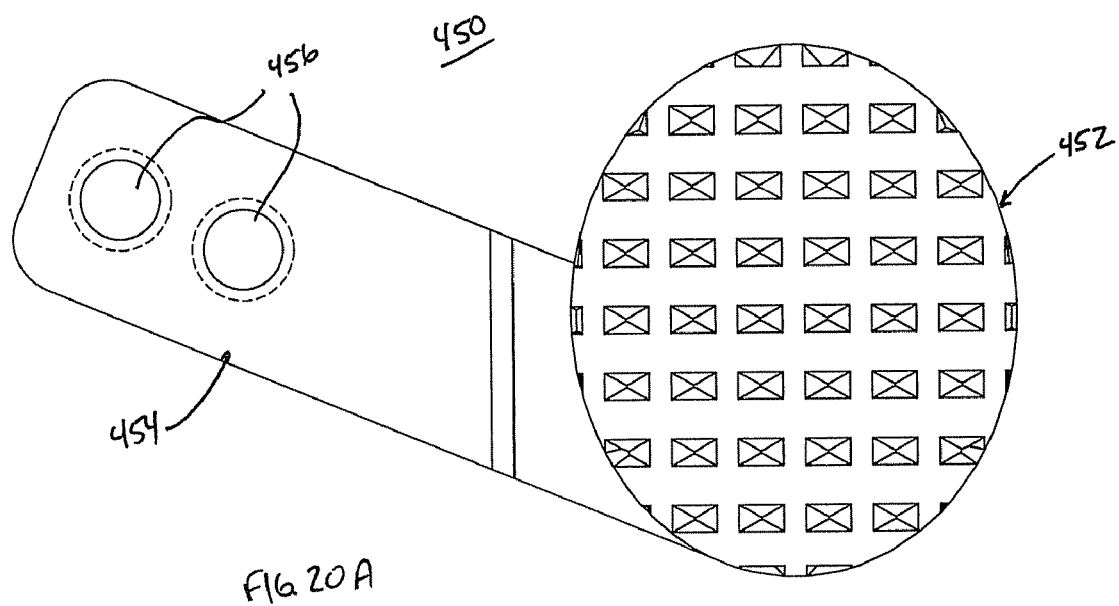
FIG. 20A is a top plan view of another resurfacing device useful with facet joint treatment systems in accordance with principles of the present disclosure.
Figure 20B:
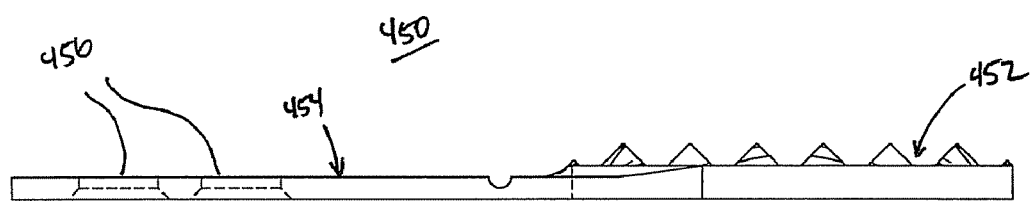
FIG. 20B is a side view of the resurfacing device of FIG. 20A.

Yet another embodiment resurfacing device 450 akin to the resurfacing device 400 (FIGS. 16A and 16B) described above and useful as part of a facet joint treatment system in accordance with the present disclosure is illustrated in FIGS. 20A and 20B. The resurfacing device 450 includes a resurfacing body 452 and a tab 454. The resurfacing body 452 can have any of the forms previously described, with the tab 454 projecting therefrom and forming various features (e.g., screw holes 456) that facilitate fixation of the resurfacing device 450 relative to a facet joint. With the construction of FIGS. 20A and 20B, the tab 454 extends at an angle relative to an axis of the resurfacing body 452. The angled tab construction may facilitate easier insertion of the resurfacing body 452 within a facet joint, as well as capturing of the resurfacing device 450 to the facet joint capsule.

Yet another facet joint treatment system 500 in accordance with the present disclosure is shown in FIGS. 21A-21C, and includes a superior resurfacing device 502 and an inferior resurfacing device 504. The resurfacing devices 502, 504 are substantially identical, and each consists of a resurfacing body 506, 508, respectively, having a base web 510, 512 and an engagement structure 514, 516. A first major surface 518 of the superior resurfacing body 506 is configured to slidably interface (e.g., articulate) with a corresponding major surface 520 of the inferior resurfacing body 508, with the respective base webs 510, 512 exhibiting sufficient conformability to substantially match a contour or geometry of the facet joint articular face to which the resurfacing body 506, 508 is inserted as described above. The engagement structure 514, 516 includes a series of projecting fins 522 having the shape and arrangement as shown. With the facet joint treatment system 500 of FIGS. 21A-21C, the insertion technique can include pre-drilling of the facet joint to form a channel sized to receive the engagement structures 514, 516 of the stacked resurfacing devices 502, 504.

Figure 22A:
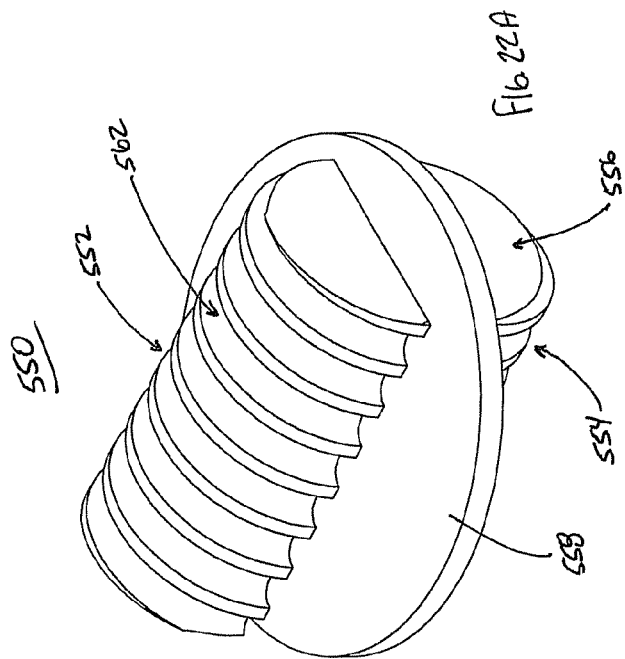
FIG. 22A is a front perspective view of another facet joint treatment system in accordance with principles of the present disclosure.
Figure 22B:
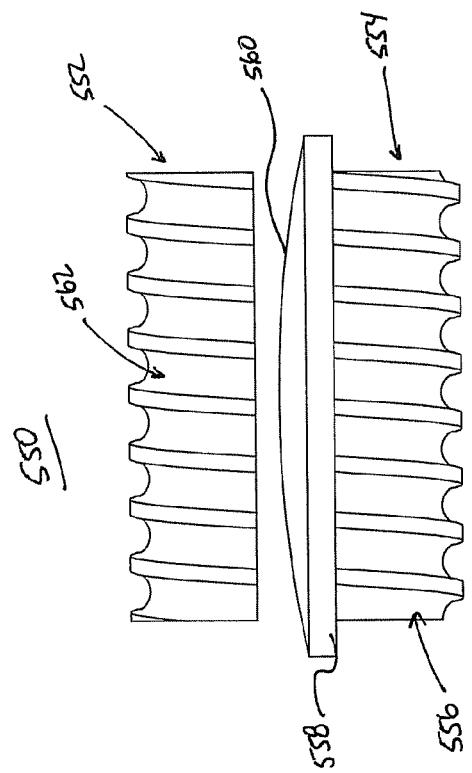
FIG. 22B is a side, exploded view of the system of FIG. 22A.

A related embodiment facet joint treatment system 550 is shown in FIGS. 22A and 22B, and includes superior and inferior resurfacing devices 552, 554. As shown, a resurfacing body 556 of the inferior resurfacing device 554 forms an enlarged flange 558 having a convex surface 560. A resurfacing body 562 of the superior resurfacing device 552 has a corresponding concave surface (hidden in the views) that slidably interfaces or articulates relative to the convex surface 560 upon final insertion into the facet joint.

Figure 23:
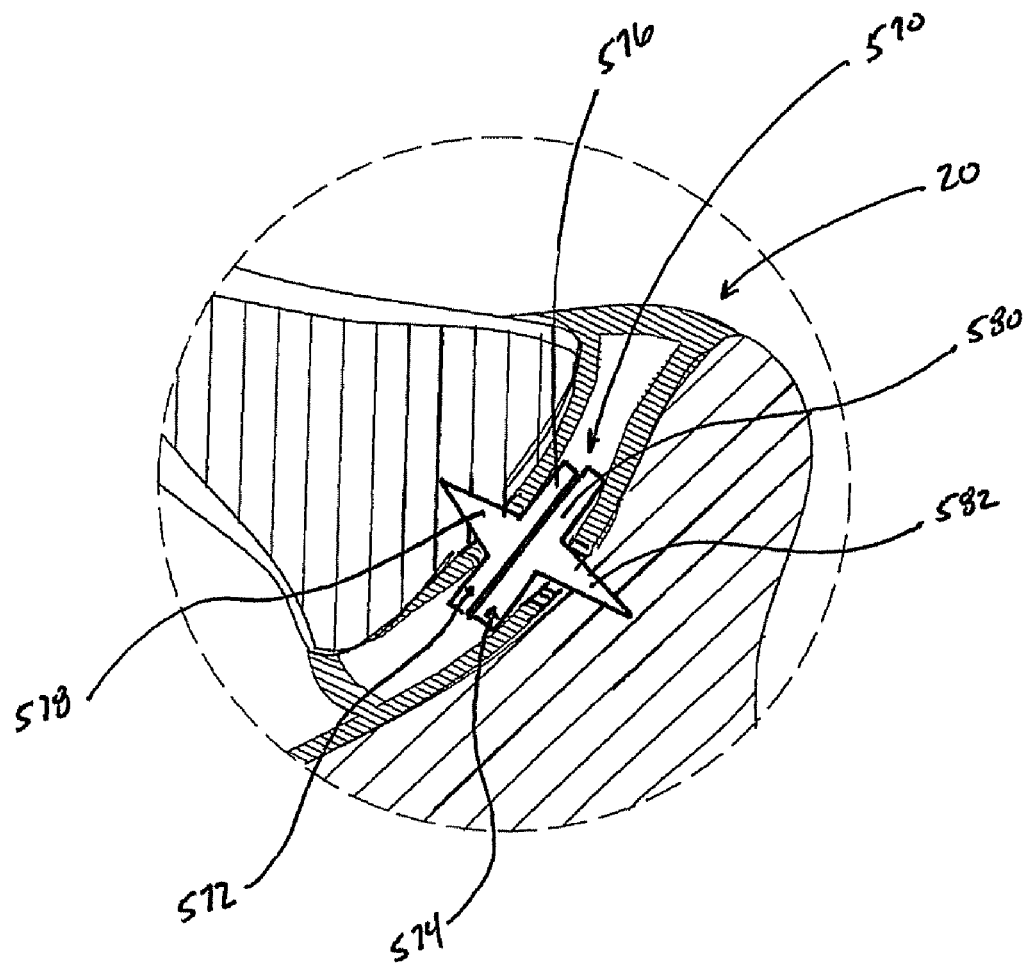
FIG. 23 is a sectional view of a facet joint to which another facet joint treatment system of the present disclosure is implanted.

Another embodiment facet joint treatment system 570 is shown in FIG. 23, and includes superior and inferior resurfacing devices 572, 574. The resurfacing devices 572, 574 are, in some constructions, identical, and are akin to thumbtacks. Thus, the superior resurfacing device 572 includes a resurfacing body 576 and a stem 578; similarly, the inferior resurfacing device 574 includes a resurfacing body 582 and a stem 584. The resurfacing bodies 576, 580 can be omnidirectional, and provide opposing articulating surfaces. The resurfacing devices 572, 574 are secure within the facet joint 20 via embedding of the stems 578, 582 into corresponding articular facet bone.

Figure 24A:
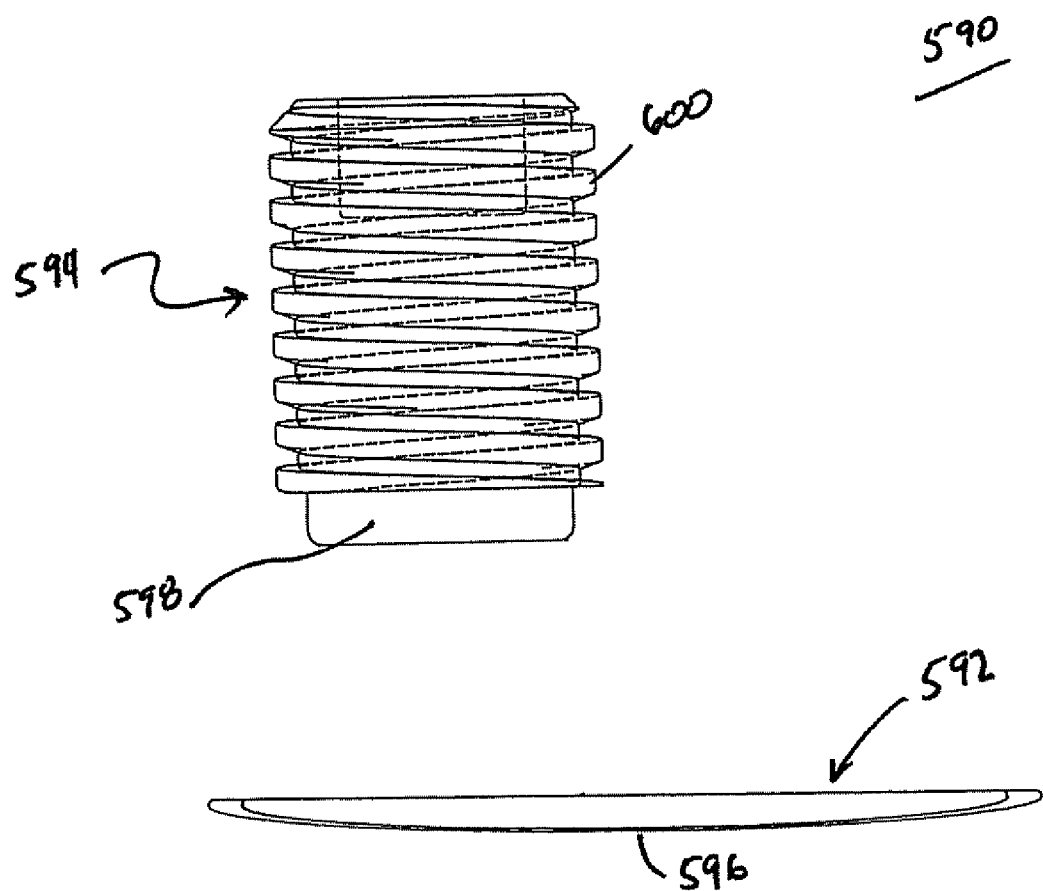
FIG. 24A is a side, exploded view of another facet joint treatment system of the present disclosure.

Yet another embodiment facet joint treatment system 590 is shown in FIG. 24A, and includes a resurfacing device 592 and a retainer 594. The facet joint treatment system 590 is adapted for anteroposterior insertion, with the resurfacing device 592 providing a bearing surface 596. The retention device 594 is selectively assembled to the resurfacing device 592 via insertion of a leading end 598 thereof into a corresponding slot (not shown) formed in the resurfacing device 592. Further, the retention device 594 is adapted for robust affixment with boney structures, and includes or forms exterior threads 600.

Figure 24B:
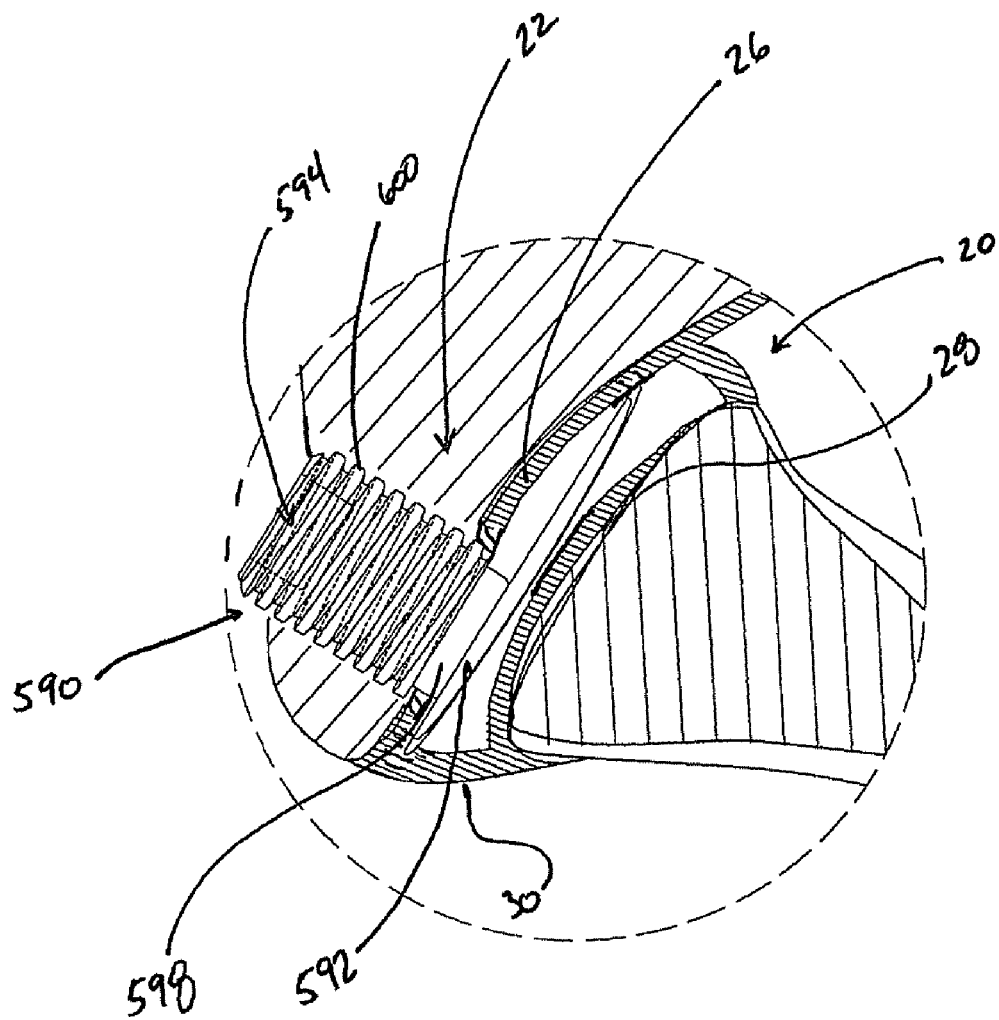
FIG. 24B is a sectional view of the system of FIG. 24A implanted to a facet joint.

As shown in FIG. 24B, insertion of the treatment system 590 to the facet joint 20 entails initial insertion of the resurfacing device 592 into the joint capsule 32, between the articular faces 26, 28. The retention device 594 is directed through the superior articular facet 22 as shown, with the threads 600 embedding into the boney mass of the superior articular facet 22. Forced threading of the retention device 594 continues until the leading end 598 engages the resurfacing device 592, establishing positive fixation of the resurfacing device 592 relative to the facet joint 20.

Figure 25A:
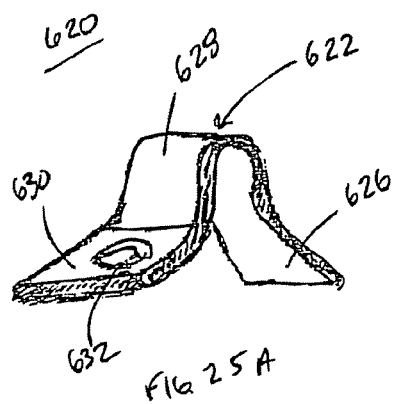
FIG. 25A is a perspective view of a portion of another facet joint treatment system of the present disclosure.
Figure 25B:
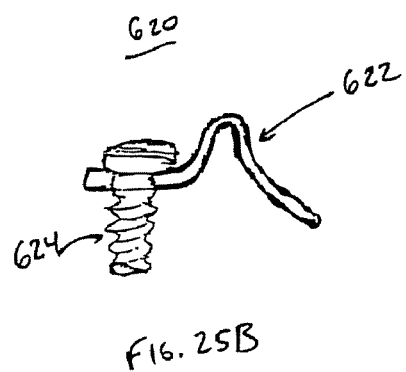
FIG. 25B is a side view of the system of FIG. 25A.

Yet another embodiment facet joint treatment system 620 is shown in FIGS. 25A and 25B, and includes a resurfacing device 622 and a retention device 624 (shown in FIG. 25B). The resurfacing device 622 serves as a joint spacer as described below, and can be formed of various materials. In some embodiments, the resurfacing device 622 is conformable, having a shape generally akin to that illustrated in FIG. 25A. In some constructions, the resurfacing device 622 is a homogenous body defined by a leading segment 626, a central segment 628, and a trailing segment 630. The leading and central segments 626, 628 are generally shaped in accordance with the expected contours of a facet joint. The trailing segment 630 projects from the central segment 628 and provides one or more features that interface with the retention device 624. For example, with embodiments in which the retention device 624 is a bone screw or similar component, the trailing segment 630 can form a hole 632 through which the retention device 624 is received.

Figure 25C:
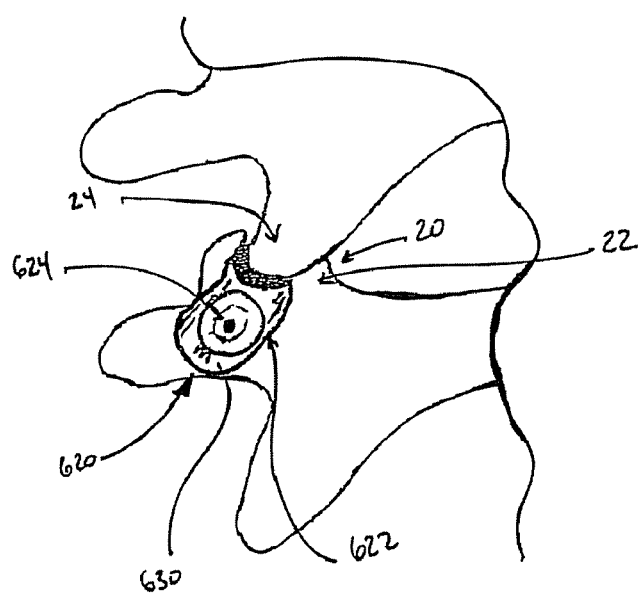
FIG. 25C is a simplified perspective view of the system of FIG. 25B implanted to a facet joint.

As shown in FIG. 25C, insertion of the resurfacing systems 620 to the facet joint 20 includes inserting a portion of the resurfacing device 622 (e.g., the leading and central segments 626, 628) between the articular facets 22, 24. The trailing segment 630 projects from the facet joint 20, and is affixed to vertebral bone via the retention device 624. The resurfacing device 622 thus serves to cover one (or both) of the native articular surfaces, and assists in establishing near-normal joint spacing. Though not shown, a second resurfacing device 622 can also be inserted to the facet joint 20 in a similar manner, with the two resurfacing devices 622 articulating against one another with motion of the facet joint 20.

The following examples and comparative examples further describe the resurfacing bodies of the present disclosure and the tests performed to determine the various characteristics of the resurfacing bodies. The examples are provided for exemplary purposes to facilitate an understanding of the present disclosure, and should not be construed to limit the present disclosure to the examples.

EXAMPLES AND COMPARATIVE EXAMPLES

Conformability Factor Test

A resurfacing device can have a range of thicknesses or forms, and so a structural property, as opposed to a material property (e.g., modulus), is sought as a measure of conformability. However, basic engineering measures of structural rigidity, such as flexural rigidity, are insufficient because a combination of deformation processes may be involved in conforming to the anatomical shape (e.g., elastic deformation, plastic deformation, creep, articulation, etc.). With this background in mind, a Conformability Test has been established in which a sample is deflected and compressed between a convex probe and a concave trough, and from which the Conformability Factor of the sample can be determined. In particular, the concave trough is formed in a polished stainless steel material block, and has a radius of 7.1 mm and a chord length of 9 mm. As a point of reference, studies by the inventors have found that a minimum radius of curvature of a typical adult human facet joint is 7 mm, and that an appropriate resurfacing body has a minimum length (e.g., major diameter) of 9 mm. Thus, the concave trough associated with the Conformability Test reflects a "worst case" implantation environment. The resurfacing body to be evaluated is placed onto the material block, over the concave trough. A convex-ended impounder probe formed of a hard material (e.g., Delrin®) having a radius of curvature of 5.5 mm is assembled to an axial loading machine (e.g., 858 Mini Bionix® Test System from MTS Systems Corp. of Eden Prairie, Minn.) and arranged over the resurfacing body/concave trough. The axial loading machine is then operated to cause the convex impounder to apply an incrementally increasing load onto the resurfacing body (e.g., at a rate of 0.05 mm/s), in turn causing the resurfacing body to deflect into the concave trough via compression loading. The applied load and axial displacement of the probe are periodically recorded, with the test continuing until full displacement of the resurfacing body into the concave trough is ensured, and/or a maximum load (e.g., 500 N) is achieved.

From the recorded data, the Conformability Factor is determined as the applied load at which the resurfacing body first fully conforms to the concave trough curvature. In this regard, displacement of the resurfacing body throughout the test establishes a load-displacement curve that is characterized by two distinct phases: 1) a bending region, dominated by bending of the resurfacing body into the concave trough, and 2) a compression region, dominated by compression of the resurfacing body between the trough and the impounder. Although not necessarily completely linear, a linear curve can be fit to each of these regions. The "inflection point" between (or point of intersection of) these two curves represents the point at which the resurfacing body transitions from bending to compression, and thus approximates initial, full conformance to the concave surface. The applied load corresponding to the so-determined "inflection point" is designated as the Conformability Factor for the resurfacing device under consideration.

EXAMPLES

Sets of three sample resurfacing body blanks (i.e., smooth discs) were prepared from PEEK material, each having a major diameter of 9 mm. Each of the three samples of a first set was formed to a thickness of 0.25 mm ("Example A"). Each of the three samples of a second set was formed to a thickness of 0.38 mm ("Example B"). Each of the three samples of a third set was formed to a thickness of 0.51 mm ("Example C").

Comparative Example

A set of three sample resurfacing body blanks (i.e., smooth discs) was prepared from PEEK material, each having a major diameter of 9 mm and a thickness of 1.02 mm ("Comparative Example").

Each of the Examples and Comparative Example samples were subjected to the Conformability Test described above and the Conformability Factor determined by the inflection point methodology. The results are provided in the Table below:

| Sample | Bending Stiffness (N/mm) | Compression Stiffness (N/mm) | Conformability Factor (N) |
|---|---|---|---|
| A-1 | 1.9 | 8175 | 3.3 |
| A-2 | 1.2 | 7948 | 2.4 |
| A-3 | 1.5 | 8268 | 2.7 |
| B-1 | 5.9 | 9658 | 7.7 |
| B-2 | 6.6 | 8730 | 9.7 |
| B-3 | 4.7 | 8857 | 5.7 |
| C-1 | 15.6 | 6656 | 20.2 |
| C-2 | 14.5 | 9794 | 19.9 |
| C-3 | 14.6 | 7960 | 20.3 |
| Comp Ex-1 | 109.5 | 4571 | 155 |
| Comp Ex-2 | 113.7 | 6878 | 163 |
| Comp Ex-3 | 98.0 | 4067 | 149 |

From the above test results, the Examples were found to be conformable in accordance with the present disclosure, each exhibiting a Conformability Factor of not more than 100 N (e.g., Example A had a median Conformability Factor of 2.7 N; Example B had a median Conformability Factor of 7.7 N; and Example C had a median Conformability Factor of 20.2 N). The Comparative Example had a median Conformability Factor of 154.5 N, and thus was deemed to not be "conformable" in accordance with present disclosure.

Although the present disclosure has been described with reference to preferred embodiments, workers skilled in the art will recognize that changes can be made in form and detail without departing from the spirit and scope of the present disclosure.

What is claimed is:

1. A system for treating a facet joint of a patient, the facet joint anatomy including opposing, superior and inferior articular faces, the system comprising:

a superior resurfacing device including a superior resurfacing body configured to selectively transition to a shape conforming to a shape of a superior articular face of a facet joint; and an inferior resurfacing device apart from the superior resurfacing device and including an inferior resurfacing body configured to selectively transition to a shape conforming to a shape of an inferior articular face of a facet joint;

wherein each of the resurfacing bodies exhibits sufficient flexibility to transition from a relatively flat state to an inserted state in which the resurfacing body substantially matches any multi-planar curvatures of the corresponding facet joint articular face in the presence of compressive forces of a typical human adult facet joint;

wherein each of the resurfacing bodies includes:
a base web forming opposing, first and second major surfaces; and
a plurality of teeth projecting from the second major surface;

wherein each of the resurfacing bodies has a leading end, a trailing end, a first opposing side that extends between the leading end and the trailing end and a second opposing side that extends between the leading end and the trailing end opposite the first opposing side; and wherein the plurality of teeth include:
a first set of teeth formed at and between the leading end and the trailing end;
a second set of teeth formed at the first opposing side, wherein the second set of teeth is oriented differently than the first set of teeth, wherein the second set of teeth each have an exterior face that faces the first opposing side and an interior face that faces the second opposing side and wherein an angle formed between the interior face and the base web is less than an angle formed between the exterior face and the base web; and
a third set of teeth formed at the second opposing side, wherein the third set of teeth is oriented differently than the first set of teeth and the second set of teeth, wherein the third set of teeth each have an exterior face that faces the second opposing side and an interior face that faces the first opposing side and wherein an angle formed between the interior face and the base web is less than an angle formed between the exterior face and the base web.

2. The system of claim 1, wherein each of the resurfacing bodies is configured to transition from the relatively flat state to the inserted state in response to normal forces applied by a human adult body weight, musculature and capsular ligaments to a major surface of the respective resurfacing body.

3. The system of claim 1, wherein each of the resurfacing bodies is configured to conform to a radius of curvature of at least 20 mm in the inserted state.

4. The system of claim 1, wherein each of the resurfacing bodies defines an anchoring surface and an articulating surface, the system configured such that upon insertion to a facet joint, the articulating surfaces abut one another in a sliding interface.

5. The system of claim 1, wherein each of the resurfacing bodies defines a disc-like shape defined by a major diameter in the range of 5-13 mm and a minor diameter in the range of 4-11 mm.

6. The system of claim 5, wherein at least one of the resurfacing devices further includes a tab extending from the corresponding resurfacing body for attachment to bone outside of a zone of interface between the superior and inferior articular faces of the facet joint.

7. The system of claim 1, wherein the resurfacing bodies are identical.

8. The system of claim 1, wherein each of the resurfacing bodies has an overall thickness in the range of 0.25-4 mm.

9. The system of claim 8, wherein each of the resurfacing bodies exhibits a Conformability Factor of not more than 100 N.

10. The system of claim 1, wherein each of the resurfacing bodies is formed of plastic.

11. The system of claim 10, wherein the plastic is a polyetherketone-based plastic.

12. The system of claim 1, wherein at least one of the teeth is defined by a leading face and a trailing face, an angle defined by the leading face and a plane of the first major surface being less than an angle defined by the trailing face and the plane of the first major surface such that the at least one tooth more overtly resists movement of the corresponding resurfacing body relative to a corresponding facet joint articular face in a first direction as compared to a second, opposite direction.

13. The system of claim 1, wherein each tooth of the first teeth set includes a leading face more proximate the leading end and a trailing face more proximate the trailing end, the leading and trailing faces intersecting at a tip opposite the first major surface, and further wherein a length of the leading face is greater than a length of the trailing face such that the corresponding tooth defines a direction of insertion of the corresponding resurfacing body from the leading end to the trailing end.

14. The system of claim 1, wherein the base web defines a substantially uniform thickness and the plurality of teeth include a first tooth proximate the leading end and a second tooth proximate the trailing end, a height of the first tooth being greater than a height of the second tooth.

15. The system of claim 1, wherein the base web forms a notch along the trailing end.

16. A kit for treating a facet joint of a patient, the facet joint anatomy including opposing, superior and inferior articular faces, the kit comprising:
 a superior resurfacing device including a superior resurfacing body configured to selectively transition to a shape conforming to a shape of a superior articular face of a facet joint;
 an inferior resurfacing device apart from the superior resurfacing device and including an inferior resurfacing body configured to selectively transition to a shape conforming to a shape of an inferior articular face of a facet joint;
 wherein each of the resurfacing bodies exhibits sufficient flexibility to transition from a relatively flat state to an inserted state in which the resurfacing body substantially matches any multi-planar curvatures of the corresponding facet joint articular face in the presence of compressive forces of a typical human adult facet joint;
 wherein each of the resurfacing bodies includes:
  a base web forming opposing, first and second major surfaces; and
  a plurality of teeth projecting from the second major surface;
 wherein each of the resurfacing bodies has a leading end, a trailing end, a first opposing side that extends between the leading end and the trailing end and a second opposing side that extends between the leading end and the trailing end opposite the first opposing side; and
 wherein the plurality of teeth include:
  a first set of teeth formed at and between the leading end and the trailing end;
  a second set of teeth formed at the first opposing side, wherein the second set of teeth is oriented differently than the first set of teeth, wherein the second set of teeth each have an exterior face that faces the first opposing side and an interior face that faces the second opposing side and wherein an angle formed between the interior face and the base web is less than an angle formed between the exterior face and the base web; and
  a third set of teeth formed at the second opposing side, wherein the third set of teeth is oriented differently than the first set of teeth and the second set of teeth, wherein the third set of teeth each have an exterior face that faces the second opposing side and an interior face that faces the first opposing side and wherein an angle formed between the interior face and the base web is less than an angle formed between the exterior face and the base web; and
 an insertion tooling set including:
  a guide wire
  a delivery cannula having a distal end and defining an internal passage open at the distal end,
  an elongate pusher tool sized to be slidably received within the passage;
  wherein the kit is configured to provide an insertion arrangement in which the resurfacing devices and the pusher tool are slidably received within the passage, the resurfacing devices being stacked against one another adjacent the distal end and a distal region of the pusher tool abutting the resurfacing devices opposite the distal end.

17. The kit of claim 16, wherein the resurfacing bodies are identical, each having a disc-like shape defined by a major diameter in the range of 5-13 mm, a minor diameter in the range of 4-11 mm, and a thickness in the range of 0.25-4 mm.

18. The kit of claim 16, wherein each of the resurfacing devices is formed of a polyetherketone-based material.

* * * * *